(12) United States Patent
Thayumanavan

(10) Patent No.: US 10,358,531 B2
(45) Date of Patent: Jul. 23, 2019

(54) CROSSLINKED POLYMER NANO-ASSEMBLIES AND USES THEREOF

(71) Applicant: University of Massachusetts, Boston, MA (US)

(72) Inventor: Sankaran Thayumanavan, Amherst, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 15/427,017

(22) Filed: Feb. 7, 2017

(65) Prior Publication Data
US 2017/0216450 A1    Aug. 3, 2017

Related U.S. Application Data

(62) Division of application No. 14/118,224, filed as application No. PCT/US2012/038972 on May 22, 2012, now Pat. No. 9,592,302.
(Continued)

(51) Int. Cl.
*A61K 9/51*    (2006.01)
*C08J 3/075*   (2006.01)
(Continued)

(52) U.S. Cl.
CPC ............... *C08J 3/075* (2013.01); *A61K 9/06* (2013.01); *A61K 9/5138* (2013.01);
(Continued)

(58) Field of Classification Search
None
See application file for complete search history.

(56) References Cited

U.S. PATENT DOCUMENTS 9,592,302 B2 *  3/2017  Thayumanavan .... C08F 220/20
9,999,599 B2 *  6/2018  Thayumanavan ... A61K 9/1075
(Continued)

OTHER PUBLICATIONS

J-H Ryu, RT Chacko, S Jiwpanich, S Bickerton, RP Babu, S Thayumanavan. "Self-Cross-Linked Polymer Nanogels: A Versatile Nanoscopic Drug Delivery Platform." Journal of the American Chemical Society, vol. 132, 2010, pp. 17227-17235. Available online Nov. 15, 2010. (Year: 2010).*
(Continued)

*Primary Examiner* — Isaac Shomer
(74) *Attorney, Agent, or Firm* — Milstein Zhang & Wu LLC

(57) ABSTRACT

The invention provides a novel system of nano-assemblies and related method for delivery of therapeutic, diagnostic or imaging agent to biological sites. The compositions and methods of the invention enable the syntheses of novel polymeric nano-assemblies (nanoparticles) under non-emulsion conditions with the incorporation of hydrophobic guest molecules. The versatilities and advantages of the polymer nanoparticles of the invention include: (i) the guest molecules (e.g., drug molecules) can be readily incorporated non-covalently within the nanoparticles; (ii) the surface of the nanoparticles are functionalizable; (iii) the non-covalently encapsulated guest molecule (payload) can be released in response to a biologically relevant stimulus at the target site; (iv) the payload is held by the polymeric nanoparticle before being internalized in cells and can be released within the cellular interiors; (v) encapsulating lipophilic small molecules within its crosslinked interiors and binding proteins on its surface through electrostatic interactions; (vi) facile synthetic methods for ligand functionalization that can be utilized to decorate nanogels with cell targeting ligands that facilitate receptor-dependent cellular uptake, and (vii) the payload release kinetics is tunable and controllable.

8 Claims, 36 Drawing Sheets

Related U.S. Application Data

(60) Provisional application No. 61/489,201, filed on May 23, 2011.

(51) Int. Cl.

| | | |
|---|---|---|
| *C08F 220/20* | (2006.01) | |
| *C08F 220/34* | (2006.01) | |
| *C08F 226/02* | (2006.01) | |
| *A61K 31/436* | (2006.01) | |
| *A61K 31/4745* | (2006.01) | |
| *C08F 8/00* | (2006.01) | |
| *A61K 9/06* | (2006.01) | |
| *A61K 31/704* | (2006.01) | |
| *C08F 220/38* | (2006.01) | |
| *C08J 3/24* | (2006.01) | |

(52) U.S. Cl.
CPC ........ *A61K 31/436* (2013.01); *A61K 31/4745* (2013.01); *A61K 31/704* (2013.01); *C08F 8/00* (2013.01); *C08F 220/20* (2013.01); *C08F 220/34* (2013.01); *C08F 220/38* (2013.01); *C08F 226/02* (2013.01); *C08J 3/24* (2013.01); *C08F 2220/387* (2013.01); *C08F 2810/20* (2013.01); *C08J 2333/14* (2013.01); *Y10S 977/773* (2013.01); *Y10S 977/906* (2013.01)

(56) References Cited

U.S. PATENT DOCUMENTS 10,131,745 B2 * 11/2018 Thayumanavan ..... C08G 69/48
2006/0240092 A1 * 10/2006 Breitenkamp ....... A61K 9/1075
424/450

OTHER PUBLICATIONS

L Zhang, W Liu, L Lin, D Chen, MH Stenzel. "Degradable Disulfide Core-Cross-Linked Micelles as a Drug Delivery System Prepared from Vinyl Functionalized Nucleosides via the RAFT Process." Biomacromolecules, vol. 9, 2008, pp. 3321-3331. (Year: 2008).*

RM Molnar, M Bodnar, JF Hartmann, J Borbely. "Preparation and characterization of poly(acrylic acid)-based nanoparticles." Colloid Polymer Science, vol. 287, 2009, pp. 739-744. (Year: 2009).*

Y Kakizawa, A Harada, K Kataoka. "Environment-Sensitive Stabilization of Core-Shell Structured Polyion Complex Micelle by Reversible Cross-Linking of the Core through Disulfide Bond." Journal of the American Chemical Society, vol. 121, 1999, pp. 11247-11248. (Year: 1999).*

* cited by examiner

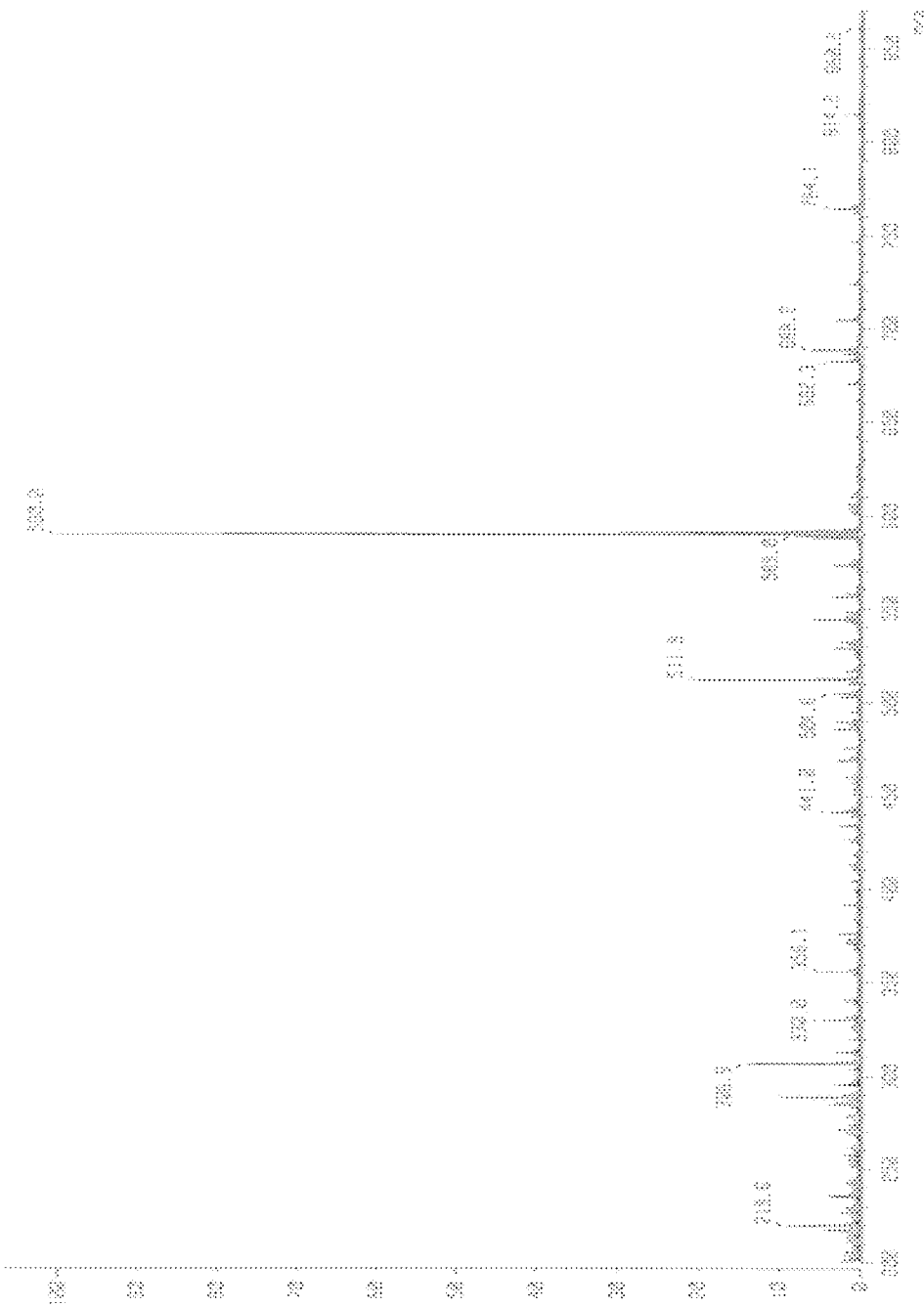
FIG. 48 CON'D

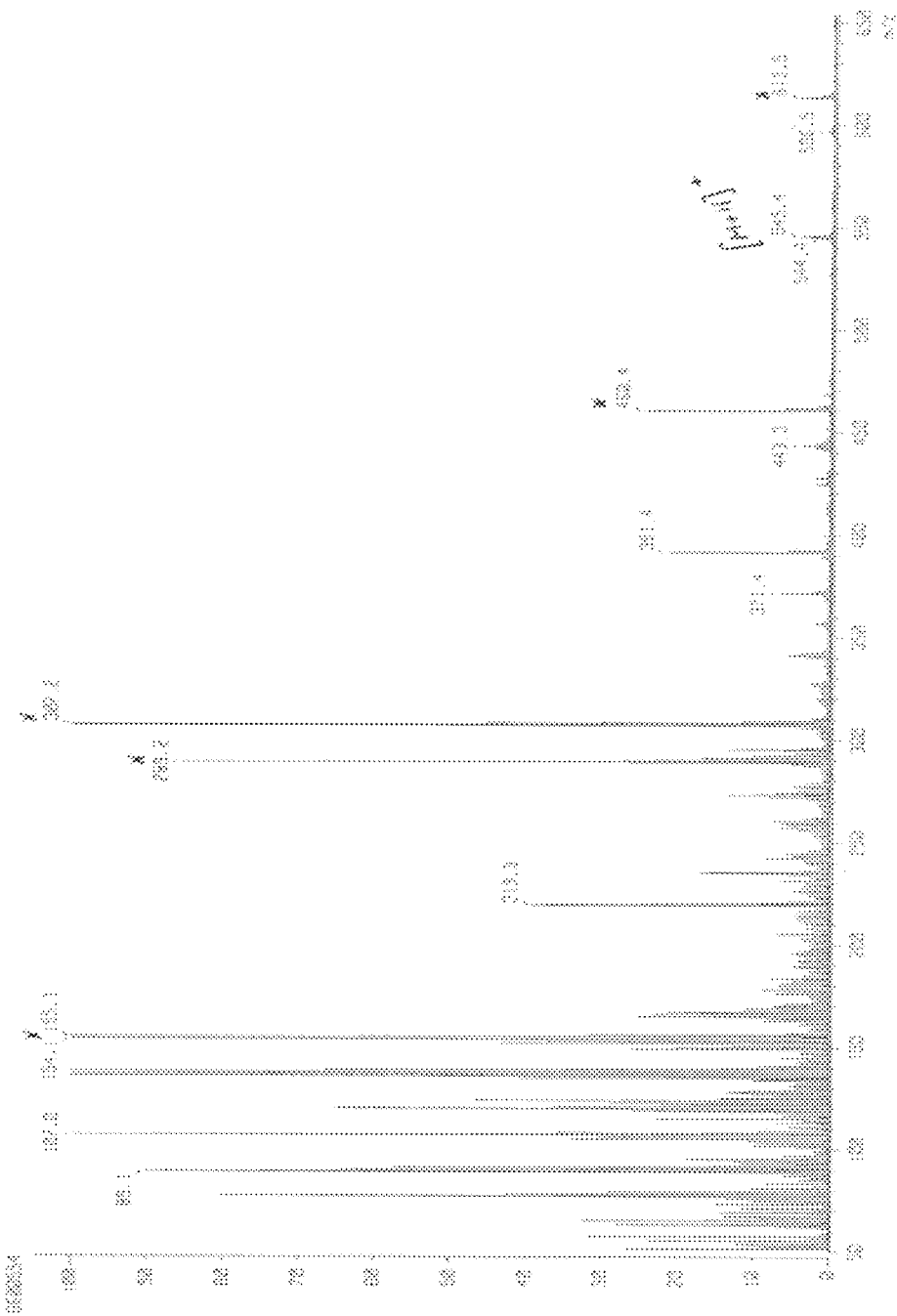
FIG. 49 CON'D

CROSSLINKED POLYMER NANO-ASSEMBLIES AND USES THEREOF

PRIORITY CLAIMS AND CROSS REFERENCE TO RELATED APPLICATIONS

This application is a divisional application of and claims the benefit of priority from U.S. patent application Ser. No. 14/118,224, filed Jan. 9, 2014, which is the U.S. National Phase of PCT/US12/38972, filed May 22, 2012, which claims the benefit of priority from U.S. Provisional Application Ser. No. 61/489,201, filed on May 23, 2011, the entire content of each of which is incorporated herein by reference in its entirety.

GOVERNMENT RIGHTS

The United States Government has certain rights to the invention pursuant to Grant No. W911NF-07-1-0462 from DARPA, Grant No. DMR-0820506 from the National Science Foundation (MRSEC), and Grant No. CMMI-0531171 from the National Science Foundation (NSEC) to the University of Massachusetts.

TECHNICAL FIELDS OF THE INVENTION

The invention generally relates to polymer nano-structures and drug delivery. More particularly, the invention relates to novel, functionalized polymer nano-assemblies that are useful as drug delivery vehicles and related methods for making the nano-assemblies and for controlled and targeted delivery of therapeutic or diagnostic agents.

BACKGROUND OF THE INVENTION

Major challenges remain in controlled administration of insoluble and toxic hydrophobic drugs to target sites. Although tremendous progress has been made in the field of delivery vehicle design, the critical issues of encapsulation stability and versatility of the delivery vehicles continue to present major difficulties. (Goldberg, et al. 2007 *J. Biomater. Sci.-Polym. E.* 18, 241-268; Allen, et al. 2004 *Science* 303, 1818-1822; Savic, et al. 2006 *J. Drug. Target* 14, 343-355.) A goal that continues to elude researchers is a functional system wherein a water-soluble container non-covalently binds hydrophobic guest molecules and releases them in a controlled manner in response to a specific trigger. (Peer, et al. 2007 *Nat. Nanotechnol.* 2, 751-760; Haag 2004 *Angew. Chem. Int. Ed.* 43, 278-282; Ganta, et al. 2008 *J. Control. Release* 126, 187-204; Allen, et al. 2004 *Science* 303, 1818-1822.) When such a container is based on a nanosized host, there is an even greater interest because of the potential in passive targeting of tumor tissue through the so-called enhanced permeability and retention (EPR) effect. (Maeda, et al. 2000 *J. Control. Release* 65, 271-284.)

Nano-scale supramolecular micellar assemblies are promising candidates because they are capable of non-covalently sequestering hydrophobic guest molecules in aqueous solution. (Duncan 2003 *Nat. Rev. Drug Discovery* 2, 347-360; Liu, et al. 2009 Macromolecules 42, 3-13; Davis, et al. 2008 *Nat. Rev. Drug Discovery* 7, 771-782; Kataoka, et al. 2001 *Adv. Drug Deliv. Rev.* 47, 113-131; Savid, et al. 2003 *Science* 300, 615-618.) However, micellar assemblies formed from small molecule surfactants have inherent stability issues.

Water-soluble cross-linked polymer nanoparticles or nanogels that can sequester lipophilic guest molecules within their interiors is of great interest in various applications ranging from delivery vehicles for therapeutics, to diagnostics to theranostics, among others. (Farokhzad, et al. 2004 *Science* 303, 1818.) However, the classical preparative methods including microemulsion or inverse microemulsion ones do not conveniently allow the nanogels to be water-soluble and encapsulate lipophilic guest molecules simultaneously. (Bachelder, et al. 2008 *J. Am. Chem. Soc.* 130, 10494; Oh, et al. 2007 *J. Am. Chem. Soc.* 129, 5939.)

Assemblies formed from amphiphilic polymers tend to exhibit enhanced stabilities, although they face significant complications because of a requisite concentration for assembly formation, which drastically limits the practicality of in vivo micelle utilization. Large dilution of injected micelles into the body can destabilize the self-assembling systems and cause uncontrolled and undesirable release of the encapsulated drug payload before arrival at the target site. (Bae, et al. 2008 *J. Control. Release* 131, 2-4.) Moreover, the interaction between micelles and biological components, such as cellular membranes and blood components, can lead to premature release of the payload from the micelle core. (Chen, et al. 2008 *Proc. Natl. Acad. Sci. U.S.A.* 105, 6596-6601; Chen, et al. 2008 *Langmuir* 24, 5213-5217.) Therefore, alternate strategies are desired to overcome such premature release.

Due to their cross-linked nature, polymer nanogels potentially provide both high encapsulation stability and potential for triggered release. (Byrne, et al. 2002 *Adv. Drug Deliv. Rev.* 54, 149-161; Kabanov, et al. 2009 *Angew. Chem. Int. Ed.* 48, 5418-5429; Kopecek 2002 *Nature* 417, 388-391; Hamidi, et al. 2008 *Adv. Drug Deliv. Rev.* 60, 1638-1649.) Current synthetic methods for nanogel preparation are based on water-in-oil emulsion, in which inverse micelles, formed from surfactants in non polar solvent, provide an aqueous interior as a reaction template for polymerization. (Bachelder, et al. 2008 *J. Am. Chem. Soc.* 130, 10494-10495; Sission, et al. 2009 *Angew. Chem. Int. Ed.* 48, 7540-7545; Kriwet, et al. 1998 *J. Controlled Release* 56, 149-158; Oh, et al. 2008 *Prog. Polym. Sci.* 33, 448-477.)

The reported nanoparticles or nanogels, however, suffer from significant limitations as they are prepared by microemulsion or inverse microemulsion methods. (Sisson, et al. 2009 *Angew. Chem. Int. Ed.* 48, 7540-7545; Bachelder, et al. 2008 *J. Am. Chem. Soc.* 130, 10494-10495; Oh, et al. 2007 *J. Am. Chem. Soc.* 129, 5939-5945.) These methods are complex and require multiple purification steps to remove unreacted monomers and surfactant materials that were used to stabilize the emulsion. When a water-soluble polymer nanoparticle is targeted, inverse microemulsion-based synthesis is a preferred method. The continuous phase in the inverse microemulsion (water-in-oil emulsion) method is based on a lipophilic solvent and, therefore, cannot be used to encapsulate hydrophobic guest molecules during nanoparticle formation. An attractive alternate to forming polymer nanoparticles is to collapse a limited number of polymer chains to achieve the desired nanoparticles. The reported methods required ultrahigh dilution conditions or inverse addition conditions, which significantly limit the capabilities in guest molecule incorporation. (Kadlubowski, et al. 2003 *Macromolecules* 36, 2484-2492; Jiang, et al. 2005 *Macromolecules* 38, 5886-5891; Mackay, et al. 2003 *Nat. Mater.* 2, 762-766; Cherian, et al. 2007 *J. Am. Chem. Soc.* 129, 11350-11351; Harth, et al. 2002 *J. Am. Chem. Soc.* 124, 8653-8660.)

Furthermore, nanoscale vehicles are desired that can concurrently sequester and deliver two different molecules. (Kelkar, et al. 2011 *Bioconjug. Chem.* 22, 1879-1903; Kelkar, et al. 2011 *Acc. Chem. Res.* 44, Issue #10; Jain 2001

*Nature Med.* 7, 987-989; Sengupta, et al. 2005 *Nature,* 436, 568-572.) It is difficult and complicated when a combination of a water-soluble hydrophilic molecule and a water-insoluble lipophilic molecule are to be co-encapsulated and delivered, partly due to the tendency of proteins to irreversibly denature under non-native conditions. (Kim, et al. 2009 *Langmuir* 25, 14086-14092; Kim, et al. 2011 *Mol. Pharmaceutics* 8, 1955-1961; Wiradharma, et al. 2009 *Biomaterials* 30, 3100-3109.)

Targeting ligands, such as folic acid, have been studied as components of active targeting systems in drug delivery. (Nasongkla, et al. 2004 *Angew. Chem. Int. Ed.* 43, 6323-6327; Lee, et al. 2008 *Angew. Chem. Int. Ed.,* 47, 2418-2421; Aluri, et al. 2009 *Adv. Drug Delivery Rev.,* 61, 940-952; Sudimack, et al. 2000 *Adv. Drug Delivery. Rev.* 41, 147-161.) Ligands are attached to the hydrophilic ends of assembly-forming amphiphilic molecules. (Sutton, et al. 2007 *Pharm. Res.* 24, 1029-1046; Yoo, et al. 2004 *J. Controlled Release* 96, 273-283; Xu, et al. 2007 *Angew. Chem. Int. Ed.* 46, 4999-5002.) However, the installation of such ligands onto these molecules requires complicated synthetic steps, limiting the versatility of ligand functionalization to tailor carriers for targeting specific cell types.

Thus, novel and improved polymer nano-assemblies and methods of preparation are required to overcome the limitations and shortcomings of the existing methods, in particular, those that can transport diverse payloads and with versatile and effective targeting capabilities are strongly desired.

SUMMARY OF THE INVENTION

The invention is based, in part, on the unexpected discovery of novel polymeric nano-assemblies (nanoparticles or nanogels) and novel methods that allow for their syntheses under non-emulsion conditions with the incorporation of hydrophobic guest molecules. The polymer nanoparticles of the invention offer versatilities and advantages over the existing systems. The guest molecules (payload) can be readily incorporated non-covalently within the nanoparticles and can be released in a controlled manner in response to a biologically relevant stimulus at the desired biological site. The payload is held by the polymeric nanoparticle before being internalized in cells and can be released within the cellular interiors The surface of the nanoparticles are readily functionalizable. The payload release kinetics is tunable and controllable allowing for diverse applications.

The invention also provides facile methods to achieve polymeric nanogels using simple reactions between the lipophilic activated esters and diamines. This strategy offers the advantage that the syntheses of nanogels are not limited to disulfide crosslinked systems or self-crosslinking reactions. The intermolecular nature of the crosslinking reaction allows for incorporation of a broader variety of stimuli-sensitive features in the diamine crosslinkers and thus in the nanogels.

Additionally, the invention provides nanogels that are capable of encapsulating lipophilic small molecules within its crosslinked interiors and are capable of binding proteins on its surface through electrostatic interactions. The nanogels can be efficiently functionalized with cell penetrating peptides. The nanogels bind oppositely charged proteins. The charge density on the nanogel surface affects the efficiency of binding of the complementarily charged proteins. Complexation of the protein with the nanogel does not alter the activity of the protein, and the complex exhibits efficient uptake by cells. Both the lipophilic small molecule and the protein are concurrently taken up by the cells. And the enzyme retains its activity even upon cellular entry.

Furthermore, the invention provides a facile synthetic method for ligand functionalization that can be utilized to decorate nanogels with cell targeting ligands. The ligand-decorated nanogels exhibit facilitated receptor-dependent cellular uptake. The selective internalization capability can be used to deliver chemotherapeutic drugs to specific receptor-rich cells. The versatile one-pot synthetic method for synthesizing the ligand-decorated nanogels, combined with the intrinsic encapsulation stability and targeting capabilities of the formed nanogels, open up new avenues in targeted and controlled drug delivery.

In one aspect, the invention generally relates to a nano-assembly for controlled delivery of a therapeutic, diagnostic or imaging agent to a biological site. The nano-assembly includes: a water-soluble polymer host comprising a network of crosslinked polymer molecules; and a guest molecule that comprises a therapeutic, diagnostic or imaging agent non-covalently associated with the polymer host. The therapeutic, diagnostic or imaging agent is releasable upon partial or complete de-crosslinking of the crosslinked network of polymer molecules at or near the biological site.

In another aspect, the invention generally relates to a nano-assembly for controlled and concurrent delivery of a small molecule agent and a non-small molecule therapeutic or diagnostic agent to a biological site. The nano-assembly includes: a water-soluble polymer host comprising a crosslinked network of polymer molecules; a guest small molecule therapeutic, diagnostic or imaging agent non-covalently associated within the crosslinked network of polymer molecules, wherein the guest small molecule therapeutic, diagnostic or imaging agent is releasable upon partial or complete de-crosslinking of the crosslinked network of polymer molecules at or near the biological site; and a guest non-small molecule therapeutic, diagnostic or imaging agent covalently linked to or non-covalently associated with the polymer host, wherein the guest non-small molecule therapeutic, diagnostic or imaging agent is releasable at or near the biological site.

In yet another aspect, the invention generally relates to a method for delivering a therapeutic, diagnostic or imaging agent to a biological site. The method includes: (1) providing a nano-assembly that includes a water-soluble polymer host comprising a crosslinked network of polymer molecules; and a guest molecule comprising a therapeutic, diagnostic or imaging agent non-covalently associated with the polymer host, wherein the therapeutic, diagnostic or imaging agent is releasable upon partial or complete de-crosslinking of the crosslinked network of polymer molecules at or near the biological site; (2) transporting the nano-assembly to the biological site; and (3) causing de-crosslinking of the crosslinked network of polymer molecules, thereby releasing the therapeutic, diagnostic or imaging agent at or near the biological site.

In certain preferred embodiments, the polymer host comprises a network of a co-polymer (block or random) having the structural formula:

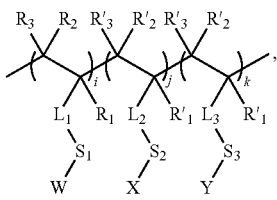

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a hydrophilic group;
X is a group comprising a crosslinking moiety;
Y is a non-crosslinking group; and
each of i and j is independently a positive number, k may be zero or a positive number.

In yet another aspect, the invention relates to a nano-vehicle useful for controlled delivery of an agent (e.g., therapeutic, diagnostic or imaging) to a biological site. The nano-vehicle includes: a water-soluble, crosslinked polymer host network; and a therapeutic, diagnostic or imaging payload non-covalently and releasably associated with the polymer host network. The therapeutic, diagnostic or imaging payload is released upon partial or complete de-cross-linking of the crosslinked polymer host network at or near the biological site.

DEFINITIONS

Figure 1:
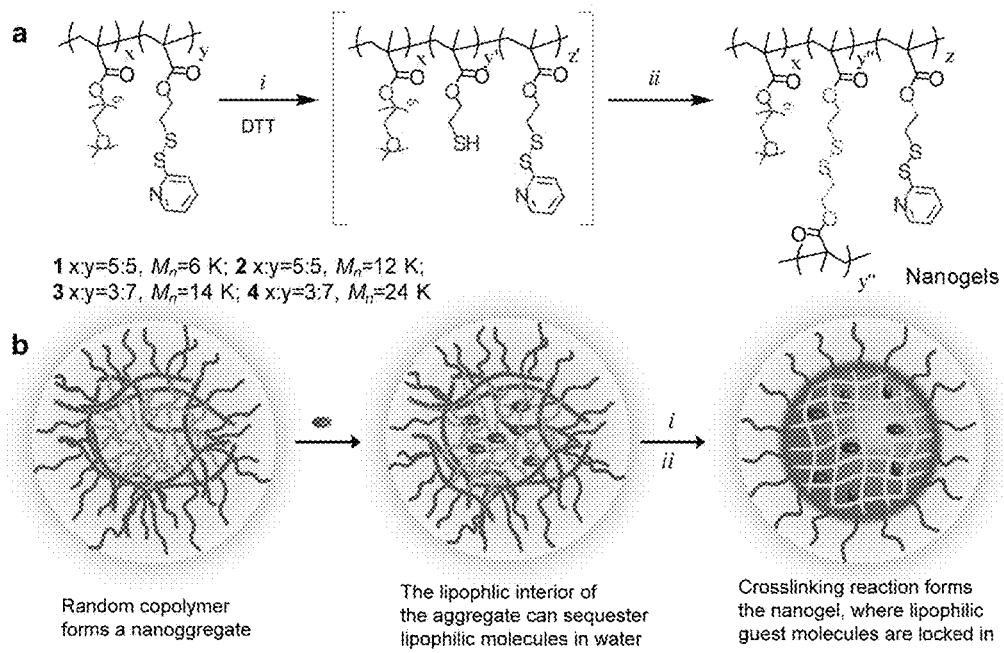
FIG. 1 shows: (a) Exemplary structures of the polymer precursors and nanogels. (i). Cleavage of specific amount of PDS group by DTT, (ii). nanogel formation by inter/intra-chain crosslinking; (b) Schematic representation of the preparation of the biodegradable nanogels.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999. It will be appreciated that the compounds, as described herein, may be substituted with any number of substituents or functional moieties.

As used herein, ($C_x$-$C_y$) refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. ($C_1$-$C_{20}$) and the likes similarly encompass the various combinations between 1 and 20 (inclusive) carbon atoms, such as ($C_1$-$C_6$), ($C_1$-$C_{12}$) and ($C_3$-$C_{12}$).

As used herein, the term "($C_x$-$C_y$)alkyl" refers to a saturated linear or branched free radical consisting essentially of x to y carbon atoms, wherein x is an integer from 1 to about 10 and y is an integer from about 2 to about 20. Exemplary $(C_x-C_y)$alkyl groups include "$(C_1-C_{20})$alkyl," which refers to a saturated linear or branched free radical consisting essentially of 1 to 20 carbon atoms and a corresponding number of hydrogen atoms. Exemplary $(C_1-C_{20})$alkyl groups include methyl, ethyl, n-propyl, isopropyl, n-butyl, isobutyl, dodecanyl, etc.

As used herein, the term, "$(C_x-C_y)$alkoxy" refers to a straight or branched chain alkyl group consisting essentially of from x to y carbon atoms that is attached to the main structure via an oxygen atom, wherein x is an integer from 1 to about 10 and y is an integer from about 2 to about 20. For example, "$(C_1-C_{20})$alkoxy" refers to a straight or branched chain alkyl group having 1-20 carbon atoms that is attached to the main structure via an oxygen atom, thus having the general formula alkyl-O—, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

As used herein, the term "halogen" refers to fluorine, chlorine, bromine, or iodine.

DETAILED DESCRIPTION OF THE INVENTION

The invention generally provides nano-scale assemblies as drug delivery vehicles that encapsulate drug molecules as payloads and release them in response to a pre-selected and specific trigger. Delivery systems of the invention are of great interest in therapeutic applications, especially for cancer, arthritis and related diseases with inflamed organs, tissues, or cells.

Micellar systems, due to their capacity to bind hydrophobic guest molecules non-covalently, are potentially good delivery vehicles to overcome the bottlenecks of traditional chemotherapies. However, the drug encapsulation stability of self-assembled systems during blood circulation continues to be a major obstacle. Thus, deliberate molecular design is required for stable encapsulation, targeting and triggered release.

Crosslinked polymer nanogels are promising systems for non-covalently encapsulating and delivering active drug molecules. However, significant hurdles remain because the classical preparative methods for polymer nanogels do not facilitate the nanogels to be both water-soluble and encapsulate lipophilic guest molecules simultaneously. These two are essential elements of a nanoscopic delivery vehicle.

The invention provides novel polymeric nano-assemblies (nanoparticles or nanogels) and novel methods of syntheses under non-emulsion conditions with the incorporation of hydrophobic guest molecules. The guest molecules (payload) can be readily incorporated non-covalently within the nanoparticles. The payload is held by the polymeric nanoparticle before being internalized and released within the cellular interiors in a controlled manner in response to a biologically relevant stimulus at the desired biological site. The payload release kinetics is tunable and controllable allowing for diverse applications. The surface of the nanoparticles is readily functionalizable.

The invention also provides facile methods to achieve polymeric nanogels using simple reactions between the lipophilic activated PFP ester and diamines. The syntheses of nanogels are not limited to disulfide crosslinked systems or self-crosslinking reactions. The intermolecular nature of the crosslinking reaction allows for incorporating a broader variety of stimuli-sensitive features in the diamine crosslinkers and thus in the nanogel. A key feature is that a lipophilic functional group that is reactive to a specific functional group is utilized to obtain the nano-assembly, which can then be locked into a nanogel by triggering a reaction.

In addition, the invention provides nanogels that is capable of encapsulating lipophilic small molecules within its crosslinked interiors and binding proteins on its surface through electrostatic interactions. The nanogels can be functionalized with cell penetrating peptides efficiently. The nanogels bind oppositely charged proteins and that the charge density on the nanogel surface affects the efficiency of binding of the complementarily charged proteins. Complexation of the protein with the nanogel does not alter the activity of the protein, and both the lipophilic small molecule and the protein are concurrently taken up by cells. The enzymatic activity remains intact even upon cellular entry. Such design strategy outlined herein can have been applied in a variety of areas including therapeutics, diagnostics, and a combination of the two by way of nanotheranostics.

Furthermore, ligand functionalization can be facilely achieved that can be utilized to decorate nanogels with cell targeting ligands. The ligand-decorated nanogels exhibit facilitated receptor-dependent cellular uptake. The selective internalization capability can be used to delivering chemotherapeutic drugs to a specific receptor-rich cells. The versatile one-pot synthetic method for synthesizing the ligand-decorated nanogels, combined with the intrinsic encapsulation stability and targeting capabilities of the formed T-NGs, open up new avenues in targeted drug delivery for crosslinked polymer nanogels.

In one aspect, the invention generally relates to a nano-assembly for controlled delivery of a therapeutic, diagnostic or imaging agent to a biological site. The nano-assembly includes: a water-soluble polymer host comprising a network of crosslinked polymer molecules; and a guest molecule that comprises a therapeutic, diagnostic or imaging agent non-covalently associated with the polymer host. The therapeutic, diagnostic or imaging agent is releasable upon partial or complete de-crosslinking of the crosslinked network of polymer molecules at or near the biological site.

In another aspect, the invention generally relates to a nano-assembly for controlled concurrent delivery of a small molecule and non-small molecule therapeutic, diagnostic or imaging agents to a biological site. The nano-assembly includes: a water-soluble polymer host comprising a crosslinked network of polymer molecules; a guest small molecule therapeutic, diagnostic or imaging agent non-covalently associated within the crosslinked network of polymer molecules, wherein guest small molecule therapeutic, diagnostic or imaging agent is releasable upon partial or complete de-crosslinking of the crosslinked network of polymer molecules at or near the biological site; and a guest non-small molecule therapeutic, diagnostic or imaging agent covalently linked to or non-covalently associated with the polymer host, wherein the guest non-small molecule therapeutic, diagnostic or imaging agent is releasable at or near the biological site.

In yet another aspect, the invention generally relates to a method for delivering a therapeutic, diagnostic or imaging agent to a biological site. The method includes: (1) providing a nano-assembly that includes a water-soluble polymer host comprising a crosslinked network of polymer molecules; and a guest molecule comprising a therapeutic, diagnostic or imaging agent non-covalently associated with the polymer host, wherein the therapeutic, diagnostic or imaging agent is releasable upon partial or complete de-crosslinking of the crosslinked network of polymer molecules at or near the biological site; (2) transporting the nano-assembly to the biological site; and (3) causing de-crosslinking of the crosslinked network of polymer molecules, thereby releasing the therapeutic, diagnostic or imaging agent at the biological site.

In some embodiments, the nano-assembly further comprises targeting moieties covalently linked to or non-covalently associated with the polymer host. For example, the targeting moiety may be an antibody, an aptamer, a peptide, or a small molecule ligand.

Depending on the desired targeting approach of the nano-assembly, one consideration is that the advantage of the nano-assemblies of the invention over small molecules is targeting by EPR effect based on size of the particles. The size of the nano-assembly may be designed according to the particular applications, for example, from about 3 nm to about 300 nm (e.g., from about 3 nm to about 200 nm, from about 3 nm to about 150 nm, from about 3 nm to about 100 nm, from about 5 nm to about 300 nm, from about 10 nm to about 300 nm, from about 15 nm to about 250 nm, from about 20 nm to about 250 nm, from about 30 nm to about 250 nm, from about 50 nm to about 250 nm, from about 100 nm to about 250 nm).

In certain preferred embodiments, the guest molecule is hydrophobic.

In certain preferred embodiments, the nano-assembly is capable of penetrating cellular membrane.

In some embodiments, the polymer host comprises a network of co-polymer molecules, for example, random co-polymers.

In some embodiments, the co-polymer molecules comprise pendant hydrophilic side chains. In certain preferred embodiments, the polymer host is covalently attached to a

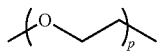

(or oligoethylene-glycol "OEG") group, wherein p is an integer from about 5 to about 200 (e.g., from about 5 to about 150, from about 5 to about 100, from about 5 to about 50, from about 10 to about 200, from about 20 to about 200, from about 50 to about 200, from about 100 to about 200, from about 10 to about 30, from about 10 to about 50).

In certain preferred embodiments, the polymer host comprises a network of a co-polymer (e.g., block or random) having the structural formula:

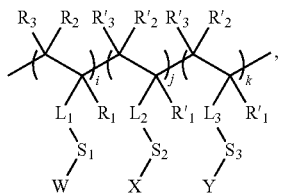

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;

W is a hydrophilic group;
X is a group comprising a crosslinking moiety;
Y is a non-crosslinking group; and
each of i and j is independently a positive number, k may be zero or a positive number.

In certain preferred embodiments, each of $R_2$, $R'_2$, $R''_2$, $R_3$, $R'_3$ and $R''_3$ is a hydrogen, and each of $R_1$, $R'_1$ and $R''_1$ is a methyl group. In some embodiments, at least one of $R_1$, $R'_1$ and $R''_1$ is a not methyl group.

In some embodiments, each of $L_1$, $L_2$ and $L_3$ is independently a group of

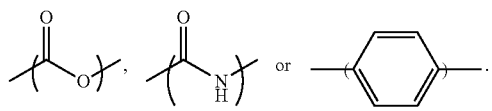

In certain preferred embodiments, W is

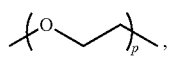

wherein p is an integer from about 1 to about 20 (e.g., from about 1 to about 3, from about 1 to about 6, from about 1 to about 9, from about 1 to about 12).

W may be a charged group, for example, an anionic or cationic group such as —$CO_2^-$, —$HPO_3^-$, —$SO_3^-$, —$NR_2$, —$NR_3^+$, wherein R is hydrogen or a $C_1$-$C_{20}$ alkyl group (e.g., a methyl, an ethyl, a $C_1$-$C_3$ alkyl, a $C_1$-$C_6$ alkyl, a $C_1$-$C_9$ alkyl group, a $C_1$-$C_{12}$ alkyl group).

W is a zwitterionic group, for example:

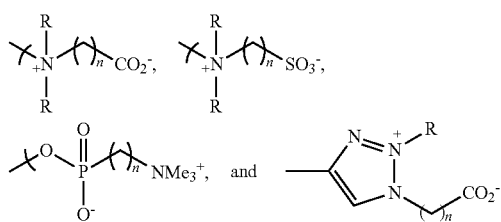

wherein each R is hydrogen or a $C_1$-$C_{20}$ alkyl group (e.g., a methyl, a ethyl, a $C_1$-$C_3$ alkyl, a $C_1$-$C_6$ alkyl, a $C_1$-$C_9$ alkyl group, a $C_1$-$C_{12}$ alkyl group; n is independently an integer from about 1 to about 12 (e.g., 1, 2, 3, 4, 5, 6, 7, 8, 9, 10, 11, 12).

W may also be a charge-neutral group, for instance:

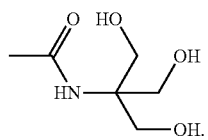

In certain preferred embodiments, the polymer host comprises a network of a co-polymer (e.g., block or random) having the structural formula:

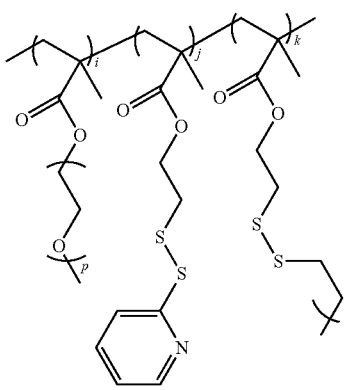

wherein p is an integer from about 1 to about 20 (e.g., from about 1 to about 3, from about 1 to about 6, from about 1 to about 9, from about 1 to about 12).

In certain preferred embodiments, X includes a disulfide group. An example of stimulus-responsive functional groups is a disulfide bond, which is susceptible to the biochemical reductants such as glutathione, thioredoxin, and peroxiredoxin. (Bernkop-Schnürch, et al. 2005 *Adv. Drug Deliv. Rev.* 57, 1569-1582; Yang, et al. 2006 *Proc. Natl. Acad. Sci. U.S.A.* 103, 13872-13877; Bauhuber, et al. 2009 *Adv. Mater.* 21, 3286-3306.)

In some embodiments, X includes a

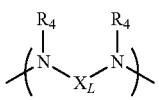

group, wherein each of $R_4$ and $R'_4$ is independently a hydrogen or $C_1$-$C_{12}$ alkyl (e.g., methyl, ethyl, a $C_3$-$C_6$ alkyl) group and $X_L$ is a spacer group. In certain preferred embodiments, each of $R_4$ and $R'_4$ is hydrogen.

$X_L$ may be a pH-sensitive functional group, for example:

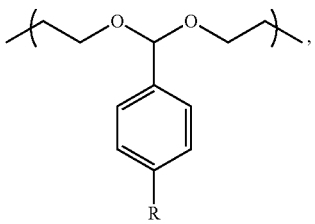

wherein R is hydrogen, a $C_1$-$C_{20}$ alkyl group, or a

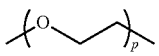

group, wherein p is from about 1 to about 100 (e.g., from about 1 to about 10, from about 1 to about 20, from about 1 to about 30, from about 1 to about 40, from about 1 to about 50).

In some embodiments, $X_L$ is a peptide having from about 1 to about 20 amino acid units (e.g., from about 1 to about 6, from about 1 to about 9, from about 1 to about 12) that are cleavable by an enzyme.

Y may be a linear or branched $C_1$-$C_{20}$ alkyl chain containing an aromatic moiety. This moiety may also be derived from an amino acid phenyl alanine or histidine, for example.

In some embodiments, Y includes a folic acid moiety, such as:

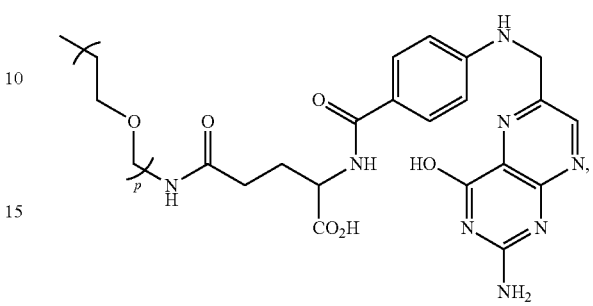

wherein q is an integer from about 1 to about 20 (e.g., from about 1 to about 3, from about 1 to about 6, from about 1 to about 9, from about 1 to about 12).

In some embodiments, Y comprises an imidazole moiety such as:

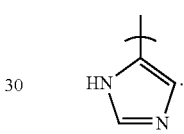

Syntheses of the nano-assemblies of the invention can be readily achieved in aqueous phase from a water-soluble precursor polymer. Incorporation of surface functionalities and noncovalent encapsulation of hydrophobic guest molecules can be achieved under mild conditions. In some embodiments, the co-polymer has a molecular weight from about 1,000 to about 100,000 (e.g., from about 2,000 to about 100,000, from about 5,000 to about 100,000, from about 10,000 to about 100,000, from about 20,000 to about 100,000, from about 50,000 to about 100,000, from about 1,000 to about 10,000, from about 1,000 to about 10,000, from about 1,000 to about 20,000, from about 1,000 to about 50,000).

In some embodiments, the ratio of i:j is in the range from about 2:8 to about 8:2 (e.g., from about 3:7 to about 7:3, from about 4:6 to about 6:4, about 1:1).

In some embodiments, where from about 1% to about 95% of j is substituted by k, for example, from about 2% to about 95%, from about 5% to about 95%, from about 10% to about 95%, from about 20% to about 95%, from about 30% to about 95%, from about 40% to about 95%, from about 1% to about 90%, from about 1% to about 85%, from about 1% to about 80%, from about 1% to about 75%, from about 1% to about 70%, from about 1% to about 60%.

The hydrophilic-lipophilic balance (HLB) has a significant impact on the aqueous phase solubility as well as the encapsulation (loading and stability) and release of a lipophilic drug from the nano-assemblies. For some applications, one may simply vary the HLB of the nano-particles by increasing OEG-based monothiol or an alkanethiol to increase the hydrophilicity or the lipophilicity of the gel respectively. This approach also provides an added advantage: By converting any residual PDS groups to vary the HLB, one mitigates toxicity and concurrently optimizes drug loading capacity, encapsulation stability, and release.

The crosslinked network of polymer molecules may be crosslinked inter-molecularly, intra-molecularly, or both. In certain preferred embodiments, the crosslinked polymer molecules are crosslinked via disulfide bonds.

The crosslinked network of polymer molecules may have a crosslinking density from about 2% to about 80%, relative to the total number of structural units in the polymer. For example, the crosslinked network of polymer molecules may have a crosslinking density from about 2% to about 70%, from about 2% to about 60%, from about 2% to about 50%, from about 2% to about 40%, from about 2% to about 30%, from about 2% to about 20%, from about 2% to about 10%, from about 5% to about 80%, from about 10% to about 80%, from about 20% to about 80%, from about 30% to about 80%, from about 40% to about 80%, relative to the total number of structural units in the polymer.

In certain preferred embodiments, the therapeutic agent is an anti-tumor agent, for example, an anti-tumor agent is selected from doxorubicin, paclitaxel, camptothecin, rapamycin, and related chemotherapeutic drugs.

The loading weight percentage of the guest molecule may be from about 0.5% to about 70% (e.g., from about 0.5% to about 60%, from about 0.5% to about 50%, from about 0.5% to about 40%, from about 0.5% to about 30%, from about 1% to about 70%, from about 2% to about 70%, from about 5% to about 70%, from about 10% to about 70%, from about 20% to about 70%, from about 30% to about 70%).

In certain preferred embodiments, the de-crosslinking of the crosslinked network of polymer molecules is caused by a biological or chemical stimulus at the biological site. For example, the stimulus is a pH value at the biological site or an external force such as light.

The biological site may be present on the surface of or within an organ or tissue, such as lungs or tumor tissue, of a subject.

The biological site may be on the surface of or inside a cell, such as the interstitial spaces or the interiors of a tumor cell of a subject.

In yet another aspect, the invention relates to a nano-vehicle useful for controlled delivery of an agent (e.g., therapeutic, diagnostic or imaging) to a biological site. The nano-vehicle includes: a water-soluble, crosslinked polymer host network; and a therapeutic, diagnostic or imaging payload non-covalently and releasably associated with the polymer host network. The therapeutic, diagnostic or imaging payload is released upon partial or complete de-crosslinking of the crosslinked polymer host network at or near the biological site.

In yet another aspect, the invention generally relates to a method for making a polymeric nano-assembly comprising a crosslinked polymeric host network while incorporating a hydrophobic payload under non-emulsion conditions.

In certain preferred embodiments, the crosslinked polymer host network is capable of crossing cellular membrane.

In certain preferred embodiments, the nano-vehicle further includes a guiding (e.g., targeting) moiety that is capable of bringing or transporting the nano-vehicle to the vicinity of or inside the biological site, wherein the guiding moiety is covalently bound to the polymer host network.

In certain preferred embodiments, the guiding moiety is an antibody or an antibody fragment.

In certain preferred embodiments, the payload is an anti-tumor agent such as doxorubicin, paclitaxel, camptothecin, rapamycin, and related chemotherapeutic drugs.

Polymeric nano-assemblies disclosed herein are highly stable, the surface of which can be functionalized using a simple intra/inter-chain crosslinking reaction. The non-covalently encapsulated guest molecules can be released in response to a certain trigger, such as a redox trigger, glutathione. Tunability in the release kinetics of the guest molecules has been demonstrated through in vitro fluorescence resonance energy transfer (FRET) experiments.

Any suitable therapeutic, diagnostic or imaging agents may be employed according to the compositions, systems and methods disclosed herein.

The kinetics of drug release can be controlled, for example, by the degree of crosslinking and by tuning the HLB. Since both nanogel formation and surface modification are accomplished by simple thiol-disulfide exchange or thiol reshuffling reactions, the reaction conditions are simple, mild, and do not require the use of organic solvents, metal containing catalysts, or additional reagents.

The invention provides a simple, emulsion-free method for the preparation of biocompatible nano-assemblies was developed that provides the ability to encapsulate hydrophobic guest molecules using intra/intermolecular disulfide formation of PDS containing polymers. Since disulfide bonds are degradable in a reducing environment, these nanoparticles hold great potential as intracelluar drug delivery vehicles. The release of guest molecules can be induced by external stimuli (e.g. Redox and pH) and in vitro release rate is tunable to crosslinking density. Additionally, it is demonstrated that these nanoparticles can be efficiently surface-functionalized under mild conditions. The nanogels also exhibit significant stability, allowing for tunable controlled release after cellular penetration; these vehicles also do not seem to suffer from guest loss prior to cellular entry. Taken together, the reversible nanogel formation using self-crosslinking polymers and corresponding method of surface modification open a new avenue for enhanced cytosolic drug delivery and establish a novel approach to creating polymer nanogels for a range of biomedical applications from drug delivery to biosensing.

EXAMPLES

Design, Syntheses, & the Size-control of the Nanogels

Illustrative examples of structures of the nanogel precursors, polymer nanogels and synthetic approach are shown in FIG. 1. The polymer nanogel precursor is based on a random copolymer that contains oligoethyleneglycol (OEG) units and pyridyldisulfide (PDS) groups as side chain functionalities. Polymers (1-4) were prepared by reversible addition fragmentation chain transfer (RAFT) polymerization. The OEG unit is used to introduce a charge-neutral hydrophilic functional group, which is known to endow biocompatibility. PDS's lipophilic functionality provides a supramolecular amphiphilic nano-assembly in the aqueous phase, which helps avoid the use of any additional surfactant molecules to generate the nanogel. The amphiphilic nature of the nano-assembly and lipophilic environment afforded by the PDS functionality also provides the opportunity for lipophilic guest molecules to be sequestered within these nano-assemblies prior to crosslinking. The PDS functionality is reactive, but specific, to thiols and provides a mild method for disulfide crosslinking to form the nanogel. Furthermore, since the nanogels are based on disulfide crosslinkers that can be cleaved by thiol-disulfide exchange reactions, these nanogels also have a pathway to release the stably encapsulated guest molecules.

Four polymers were prepared that have different molecular weights and different ratios of the OEG units to the PDS groups. Polymers 1 ($M_n$: 6,000, PDI: 1.2) and 2 ($M_n$: 12,000, PDI: 1.2) have 50% of the OEG methacrylate and 50% of the PDS-derived methacrylate. Polymers 3 ($M_n$: 14,000, PDI: 1.3) and 4 ($M_n$: 24,000, PDI: 1.6) have 30% of the OEG methacrylate and 70% of the PDS-derived methacrylate. The aggregate sizes of the polymers in the aqueous phase were investigated by dynamic light scattering (DLS). Polymers 1, 2, 3, and 4 (1 wt %) showed assemblies of 5, 8, 12, and 120 nm diameter respectively in water (FIG. 2a).

Figure 2:
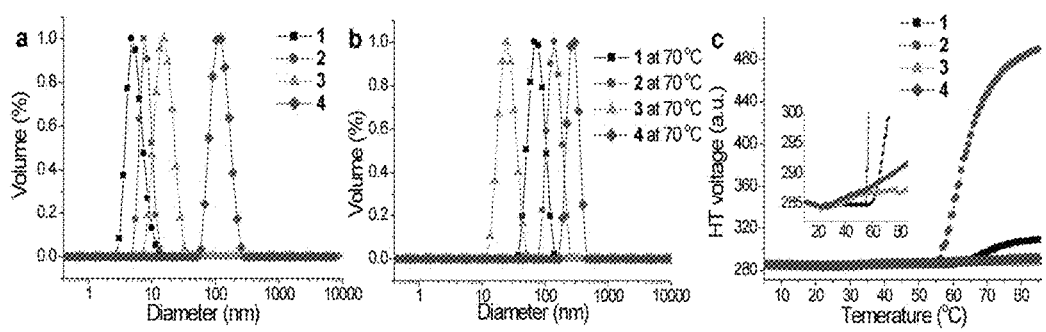
FIG. 2 shows: Exemplary size distribution of the polymer aggregates at (a) 25° C. and (b) 70° C. in water. (c) Turbidity experiment showing the change in high tension voltage with temperature of the polymer (Inset: magnification shows subtle changes in high tension voltage in polymers 3 and 4).

The polymers showed larger aggregates at high temperature, presumably because of the lower critical solution temperature (LCST) behavior of the OEG units (FIG. 2b). (Saeki, et al. 1976 *Polymer* 17, 685-689; Lutz, et al. 2006 *J. Am. Chem. Soc.* 128, 13046-13047; Lutz, et al. 2007 *Macromolecules* 40, 2503-2508; Aathimanikandan, et al. 2005 *J. Am. Chem. Soc.* 127, 14922-14929.) The degree of hydration of multiple OEG side chains reduces with increasing temperature resulting in a compact coil conformation and the polymer becomes more hydrophobic. This leads to intermolecular associations between the polymers, resulting in the formation of larger aggregates. (Vo, et al. 2002 *Colloid. Polym. Sci.* 280, 400-409.)

The LCST behavior of the polymers was investigated by temperature-dependent turbidity measurements using circular dichroism. The polymer (10 mg/mL) solutions were prepared and the changes in the high tension voltage were monitored at 600 nm by varying the temperature by 2° C./min. (Klaikherd, et al. 2009 *J. Am. Chem. Soc.* 131, 4830-4838.) As shown in FIG. 2c, polymers 1 and 2 showed large turbidity change above 60° C. and 55° C., while polymers 3 and 4 showed a small change above 30° C. and 25° C., respectively. This observation is attributed to the fact that the hydrophobicity in the polymer affects the LCST behavior. (Wang, et al. 2009 *Macromolecules* 42, 3026-3032.) At the same co-monomer composition, the turbidity change and the size are larger with increasing molecular weight due to the cooperative effect of the larger amount of OEG units. The polymer aggregates formed using these LCST behaviors are summarized in Table 1.

The next step involves the conversion of these polymeric aggregates into chemically crosslinked nanogels. Addition of a deficient amount of dithiothreitol (DTT) causes the cleavage of a well-defined percentage of the PDS groups to the corresponding thiol functionalities. These thiol functionalities then react within the polymeric aggregates with unreacted PDS functionalities. This reaction results in disulfide crosslinks within the polymeric aggregates causing the formation of the nanogels, as shown in FIG. 1.

Figure 3:
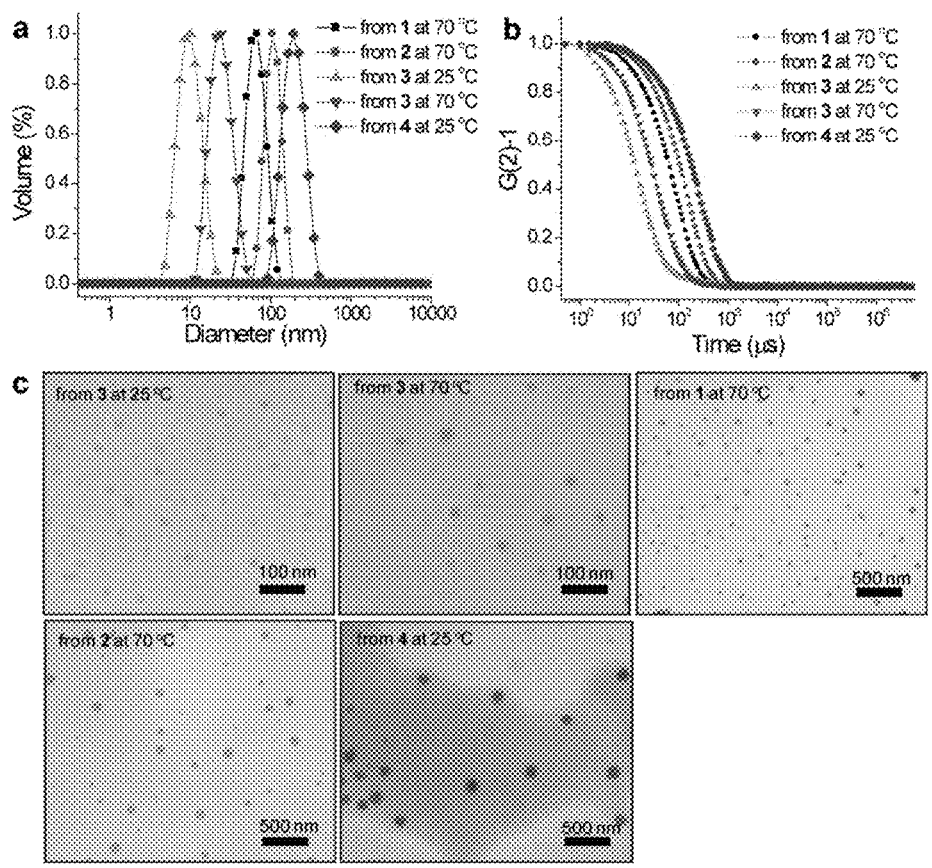
FIG. 3 shows: (a) Exemplary size distribution of the nanogels prepared by DTT addition into the polymer aggregates at 25° C. or 70° C. in water and (b) the corresponding autocorrelation functions. (c) TEM images of the nanogels.
Figure 11:
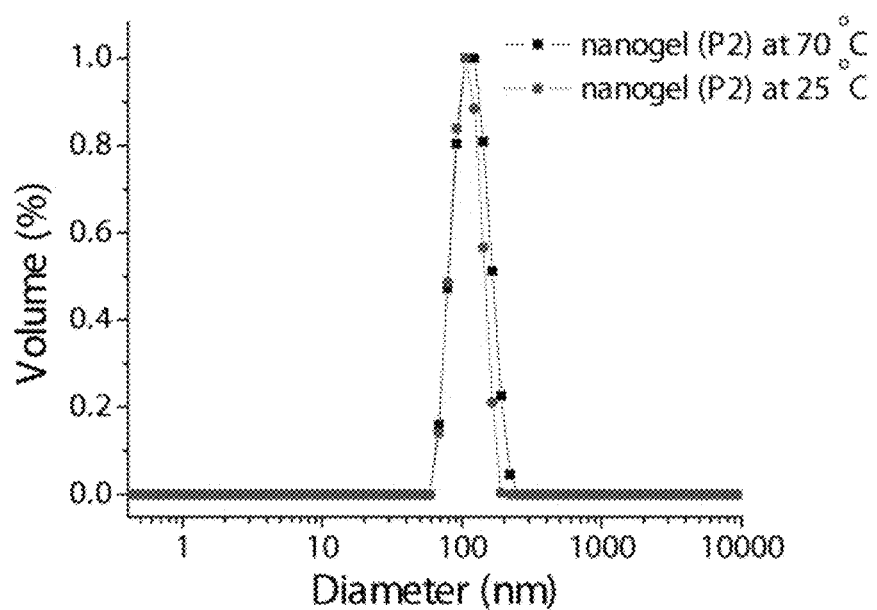
FIG. 11 shows exemplary DLS of the nanogel (from polymer 2) at 25° C. and 70° C.

By the addition of a deficient amount of DTT into these polymer assembly solutions, precise control of the size of the crosslinked nanoparticles from ~10 nm to ~200 nm in diameter was achieved. To crosslink the polymer aggregates at different temperatures, 20 mol % of DTT against total PDS groups in each polymer was added. The structures obtained from these reactions were characterized by transmission electron microscopy (TEM) and DLS. From polymers 1 and 2 70 nm and 100 nm nanogels were prepared at 70° C., respectively. While the size of the polymer aggregate is reversibly sensitive to temperature, the size of the nanogel formed after the DTT-reaction retains the size observed under reaction conditions when it was cooled down to room temperature (FIG. 11). This result suggests that stable crosslinked nanogels were formed, not polymer aggregates. Using polymer 3 10 nm and 26 nm nanogels were prepared at 25° C. and 70° C., respectively, while the aggregates of polymer 4 were converted to nanogels of 190 nm size at 25° C. As shown in FIGS. 3a and 3b, the hydrodynamic diameter and the autocorrelation function in DLS reveal that fine control over the size of the nanogels can be achieved by controlling the size of the preformed polymer aggregates in water by varying molecular weight, comonomer composition, and temperature. The evidence for the precise size control was further provided by TEM experiments (FIG. 3c). TEM images of all nanogels revealed well-defined spherical structures with sizes that correlate very well with the DLS results. These results show that the nanogel size can be systematically tuned by controlling the structure of the precursor polymer and by exploiting temperature-dependent aggregation though the LCST behavior of the polymers.

TABLE 1

Properties of polymers and the sizes of the polymer aggregates and nanogels

| Polymer | $M_n$ (PDI)[a] | Comonomer composition (OEG:PDS)[b] | Aggregate size (nm)[c] 25° C. | Aggregate size (nm)[c] 70° C. | Nanogel Size (nm) (PDI) |
|---|---|---|---|---|---|
| 1 | 6900 (1.2) | 47:53 | 5 | 74 | 68(0.07)[d] |
| 2 | 13100 (1.2) | 50:50 | 8 | 142 | 106(0.03)[d] |
| 3 | 14400 (1.6) | 33:67 | 12 | 24 | 26(0.24),[d] 10(0.33)[e] |
| 4 | 24700 (1.6) | 31:69 | 120 | 255 | 190(0.24)[e] |

[a]Estimated by GPC (THF) using PMMA standard.
[b]Determined by NMR.
[c]Determined by DLS.
[d]Prepared at 70° C.
[e]Prepared at 25° C.

Guest Encapsulation and Triggered/Controlled Release

Figure 4:
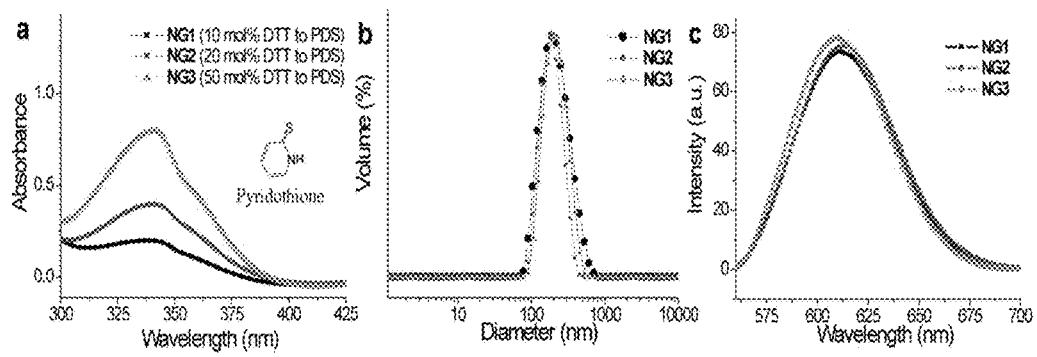
FIG. 4 shows: (a) Exemplary absorption spectra of pyridothione in UV-vis. Pyridothione, which is a byproduct during nanogel synthesis by disulfide bond formation and shows characteristic absorption at 350 nm wavelength, is monitored in each nanogel (10 mg/mL) prepared. (b) Size distribution of nanogels (1 mg/mL) by DLS. (c) The emission spectra of Nile red sequestered in polymer nanogels
Figure 12:
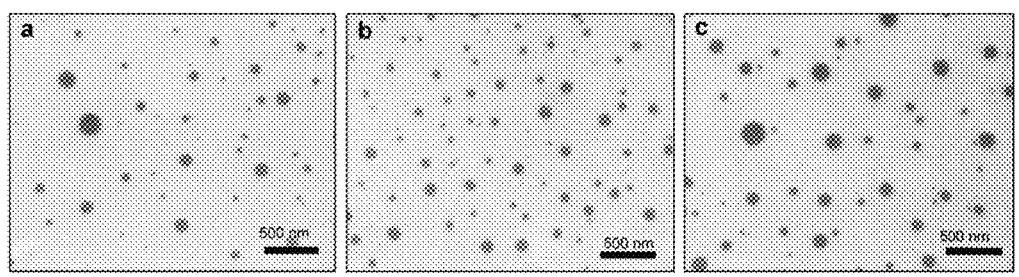
FIG. 12 shows exemplary TEM images of (a) NG1, (b) NG2, and (c) NG3.
Figure 13:
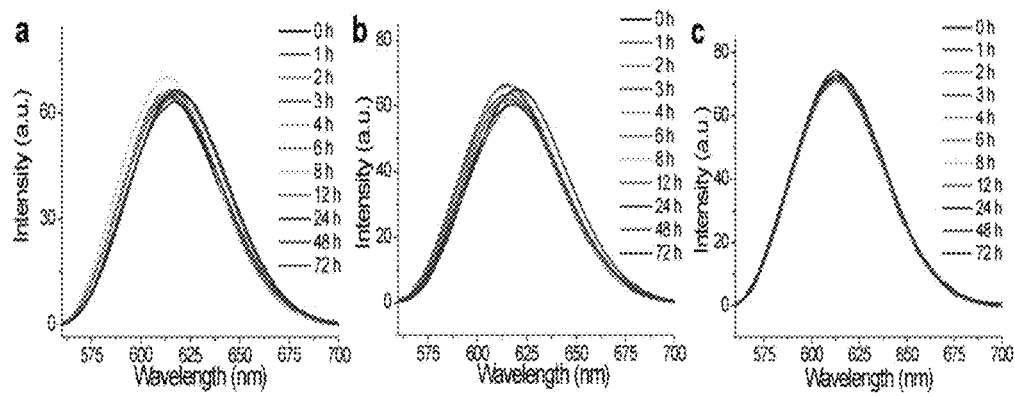
FIG. 13 shows exemplary dye release from (a) NG1, (b) NG2, and (c) NG3 (0.05 wt %) in 10 μM GSH at pH 5.

Three different crosslinked particles were prepared by adding 10, 20 or 50 mol % (against the precursor PDS groups) of DTT to polymer 4. The progress of the reaction was conveniently monitored by release of the pyridothione byproduct through tracing its characteristic absorption at 343 nm. Considering the mechanism by which this addition results in crosslinked polymer particles and the percentage of PDS functionalities in polymer 4, this reaction should result in nanoparticles NG1, NG2, and NG3 with 7%, 14%, and 35% crosslinking densities respectively, assuming 100% reaction efficiency. Estimations, based on pyridothione release, indicate that the actual crosslinking densities correspond to 6%, 13%, and 25% respectively (FIG. 4a). DLS studies reveal that the structures obtained are all about 190 nm in size (FIG. 4b). TEM images reveal well-defined spherical structures with slightly smaller diameters than those observed in DLS, which is attributed to the possible swelling of the nanoparticles in water (FIG. 12). The sizes of all three nanogels are very similar, which suggests that the size of the assembly prior to the crosslinking reaction dictates the nanogel size and that further crosslinking occurs within that nanoassembly.

To investigate encapsulation of hydrophobic guest molecules within the interiors of these nanogels, the DTT-based crosslinking reaction was carried out in the presence of Nile red, a hydrophobic dye. Nile red is inherently insoluble in water. Therefore, the reaction was optimized using acetone as a solvent in the first steps, before addition of water during the crosslinking reaction. Isolation of the nanoparticles and their subsequent dissolution in water retains the presence of Nile red, as discerned by the emission spectra of all three gels (FIG. 4c).

Figure 5:
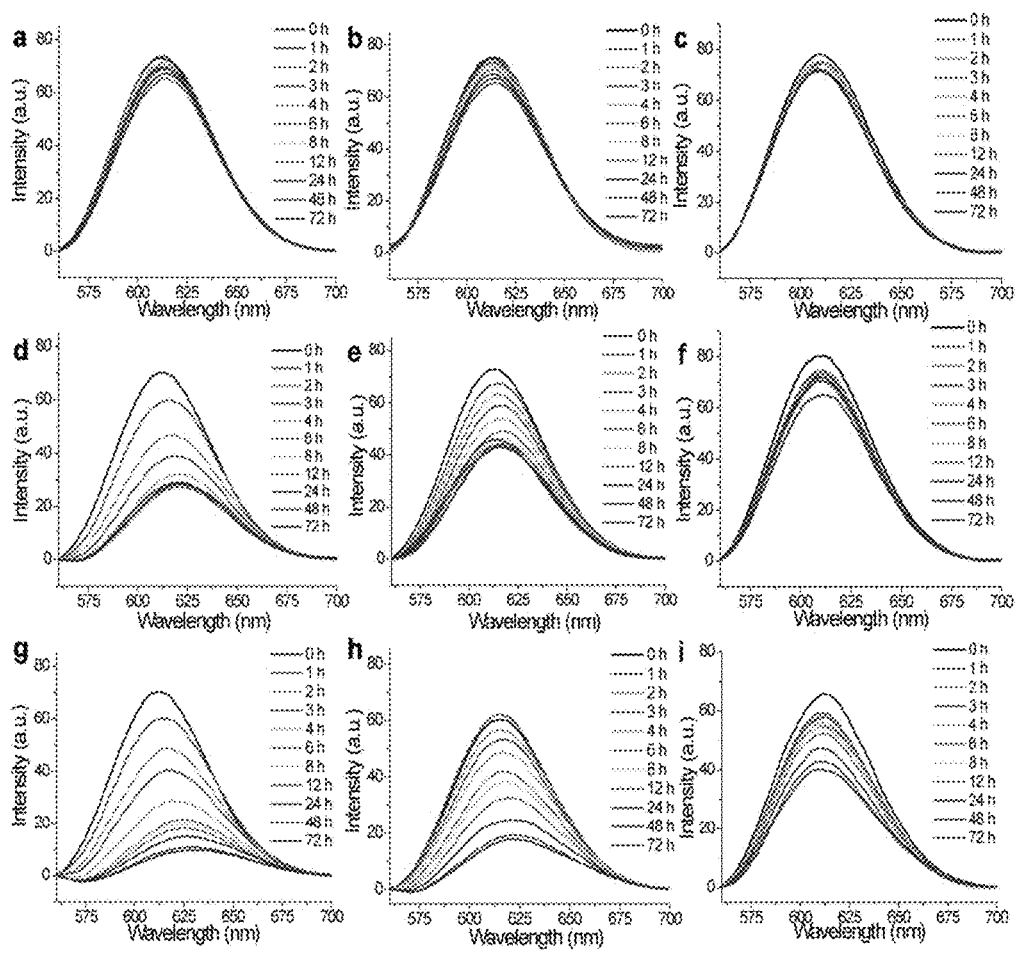
FIG. 5 shows: Exemplary dye release from the nanogels NG1 (a, d, g), NG2 (b, e, f), and NG3 (c, f, i) (0.05 wt %) in response to varied GSH concentrations. (a-c) 10 μM GSH and (d-f) 10 mM GSH at pH 7.4, and (g-i) 10 mM GSH at pH 5. The release only occurred at high GSH concentration. At acidic pH under 10 mM GSH, the release was faster and more continuous over time than that at neutral pH.

To test triggered release, GSH was added into nanogel solutions and the release of Nile red was investigated by tracing the decrease in the hydrophobic dye's spectral emission intensity caused by its insolubility in the aqueous media. To examine the GSH-dependent dye release, Nile red loaded nanogel solutions (0.05 wt %) in pH 7.4 sodium acetate buffer solution were treated with different concentrations of GSH (10 µM and 10 mM) and the intensity of Nile red emission at 610 nm was monitored for three days. At low GSH concentrations (10 µM), little dye release was observed for all nanogels (FIG. 5a-c). This concentration corresponds to that commonly observed outside the cell and within the blood plasma. In contrast, high concentrations of GSH (10 mM), corresponding to those found inside the cell, induced significant dye release (FIG. 5d-f).

Figure 6:
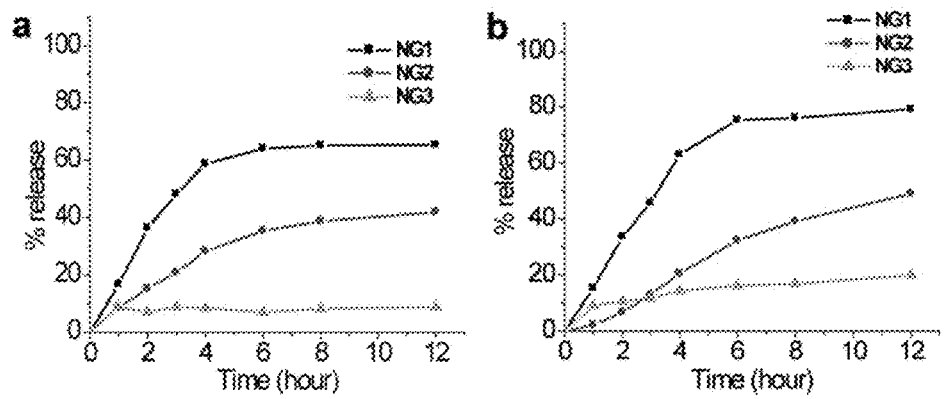
FIG. 6 shows: Exemplary comparison of GSH-induced dye release rate from the nanogels which have different crosslinking densities at (a) pH 7.4 and (b) pH 5.

The rate of dye release from the nanogel interior is influenced by crosslinking density. NG1 (6% crosslinked nanogel) showed rapid release reaching a plateau after 6 h at 10 mM GSH in pH 7.4 buffer solution. NG2 (13% crosslinked nanogel) showed slower release, reaching a maximum at 12 h; NG3 (25% crosslinked nanogel) displayed gradual, highly sustained release for several days. Since the entry of these nanogels would likely involve endocytosis, the release profile at lower pH was analyzed. The release profile difference under acidic conditions (pH 5) was very similar to that observed with pH 7 (FIG. 5g-i and FIG. 13). While this bodes well for endocytosis based entry into the cells, the release profile at high GSH concentration was surprising, as GSH activity is considered most efficient at neutral pH. (Moskaug, et al. 1987 *J. Biol. Chem.* 262, 10339-10345.) As shown in FIG. 6, similar release was observed for all three gels over several hours at both pH 5 and 7.4.

Encapsulation Stability and Tunable in vitro Guest Release

The encapsulation stability of lipophilic molecules is critical to an effective nanocarrier, preventing significant loss of drug due to leakage during circulation. A FRET based method was developed to evaluate the encapsulation stability of nanocarriers in aqueous solutions. (Jiwpanich, et al. 2010 *J. Am. Chem. Soc.* 132, 10683-10685.) The crosslinking densities can significantly influence the encapsulation stability coefficient (A).

Figure 7:
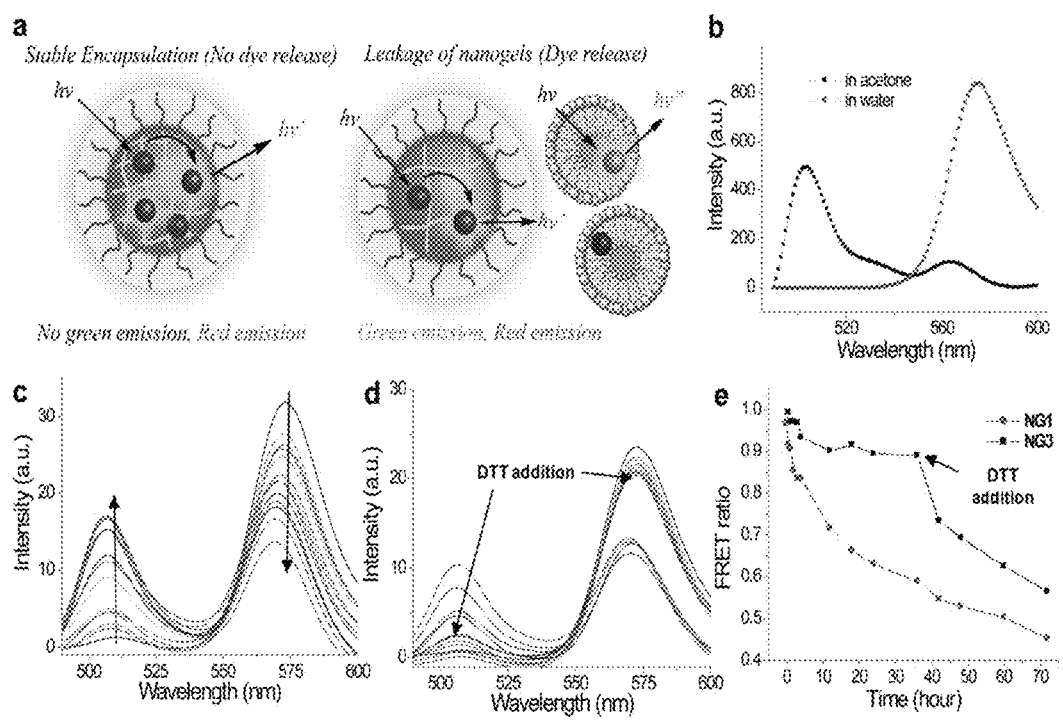
FIG. 7 shows: (a) Schematic representation of the stable and leaky nanocontainers identified by a FRET experiment. (b) Fluorescence spectra of nanogels (NG3) containing a FRET pair, DiO and DiI. Nanogel solutions (2 mg/mL) were prepared containing two hydrophobic dyes, 1 wt % DiO (donor, fluorescence at 503 nm) and 1 wt % DiI (acceptor, fluorescence at 575 nm). Time-resolved spectra of (c) NG1 (0.1 mg/mL) and (d) NG3 (0.1 mg/mL) containing two dyes after mixing with 4 mM DOPC vesicle solution. (e) Change in FRET ratio of the nanogels containing both dyes. The addition of 20 mM DTT to NG3 after 36 h showed significant decrease in the FRET ratio.

To correlate with the in vitro guest release experiments, FRET experiments were carried out to investigate the dye leakage in the presence of dioleoyl phosphatidylcholine (DOPC) bilayer vesicles. (Chen, et al. 2008 *Proc. Natl. Acad. Sci. U.S.A.* 105, 6596-6601.) FRET was used between two non-covalently encapsulated dyes as a diagnostic tool (FIG. 7a). Nanogel solutions containing a mixture of two hydrophobic dyes, 3,3'-dioctadecyloxacarbocyanine perchlorate (DiO: donor, green fluorescence) and 1,1'-dioctadecyl-3,3,3',3'-tetramethylindocarbocyanine perchlorate (DiI: acceptor, red fluorescence), were prepared. To confirm that these two dyes exhibit the requisite FRET inside the nanogels, the nanogel solution was excited at 484 nm, the wavelength at which DiO specifically absorbs. An intense DiI emission at 575 nm was observed, indicating an efficient energy transfer between the closely packed FRET partners within the nanogel interior (FIG. 7b). When this experiment was carried out in acetone, strong DiO fluorescence at 503 nm was observed along with significant reduction of DiI emission, suggesting a loss of FRET due to diffusion of the dyes from the nanogel interior to the solvent. Note that both DiO and DiI are soluble in acetone, but insoluble in water.

DOPC vesicles can absorb the dye molecules, if available in solution. Therefore, if the dye molecules are not stably encapsulated within the nanogels, the transient presence of these dye molecules in the aqueous milieu will result in equilibration of the dye between the DOPC vesicles and the nanogels. This process results in loss of FRET with leaky nanogels, due to the sparse distribution of each dye into the bilayer of DOPC. To investigate the behavior of the nanogels, the fluorescence intensities of nanogel solutions containing DiO and DiI dyes were monitored for 3 days by exciting the solution at 450 nm (DiO). The disappearance of FRET due to the release of hydrophobic guest molecules was then monitored by tracing the increase in the donor (DiO) emission and the concomitant decrease in the acceptor's (DiI). FIGS. 7c-d show the change of the dye emission pattern with different crosslinked nanogels, NG1 (6% crosslinked) and NG3 (25% crosslinked). In the case of the highly crosslinked nanogel (NG3), the emission of FRET remained relatively steady throughout the time of the experiment (FIG. 7d), indicating that the two dyes are stably trapped inside the nanogels.

Conversely, in the case of the lightly crosslinked nanogel (NG1), the acceptor's (DiI) emission was gradually decreased over the three days period with concurrent increase in the donor's (DiO) emission (FIG. 7c). This result indicates that the hydrophobic guest molecules were transferred from the nanocontainer to the DOPC vesicle bilayer. Even though NG1 showed less encapsulation stability than NG3, the leakage is much slower than that from block copolymer micelles previously reported, suggesting the versatility of these nanogels as a delivery vehicle candidate. (Chen, et al. 2008 *Proc. Natl. Acad. Sci. U.S.A.* 105, 6596-6601.) The addition of DTT (20 mM) to the stable nanocontainer (NG3) containing the two dyes led to decreasing FRET (FIG. 7d). The FRET ratio $I_a/(I_d+I_a)$ plotted against time, where $I_a$ and $I_d$ are the maximum emission intensities of the acceptor (DiI) and the donor (DiO) at 575 nm and 503 nm, respectively, clearly shows the difference in encapsulation stabilities of these nanogels (FIG. 7e). This result means that the drug molecules can stably remain inside the nanocontainer during circulation, but be released inside the target cells in response to the higher reductant (GSH) levels.

Figure 8:
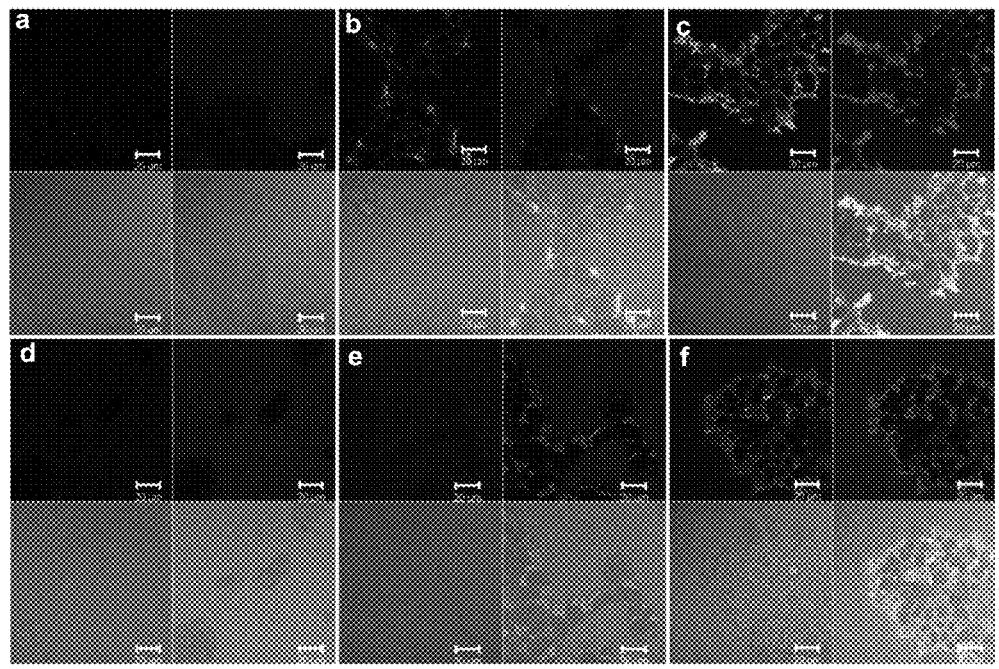
FIG. 8 shows: Exemplary confocal microscopy images of nanogels containing DiO and DiI as a FRET pair at different incubation times. NG1, 6% crosslinked gels, were incubated with MCF-7 cells for (a) 2 h, (b) 4 h, and (c) 24 h. NG3, 25% crosslinked gels, were incubated with MCF-7 cells for (d) 2 h, (e) 4 h, and (f) 24 h. Within each image set, top left is the DiO channel which shows green color (no FRET, dye release) and top right is the DiI channel which shows red color (FRET, no dye release). Bottom left is the DIC image and bottom right is an overlap of all three. Yellow color is overlay with green and red. Scale bar is 20 m.
Figure 14:
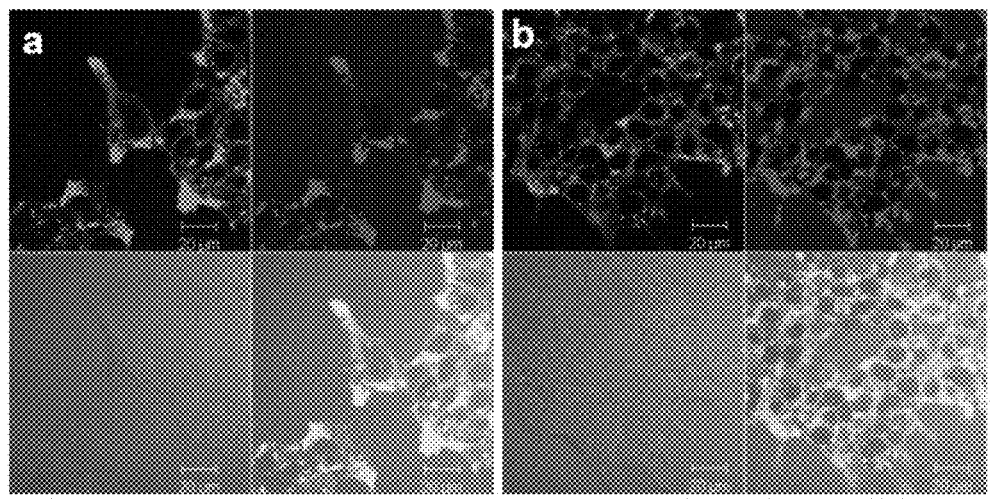
FIG. 14 shows exemplary DiO (green) and DiI (red) release form (a) NG1, and (b) NG3 after 48 h.
Figure 15:
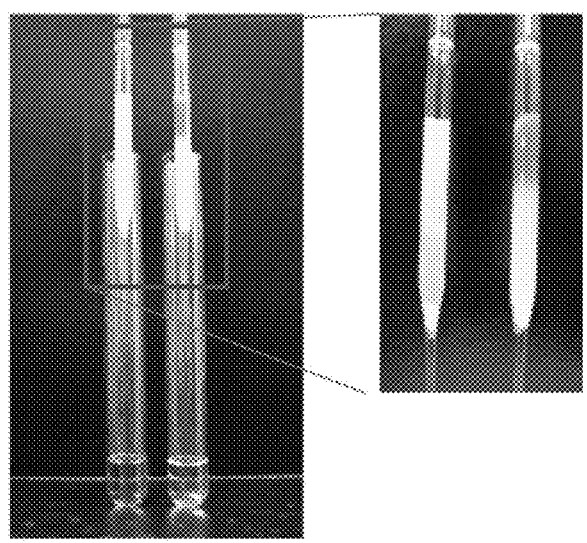
FIG. 15 shows exemplary size exclusion chromatography of Dox-containing nanogel and free Dox.
Figure 16:
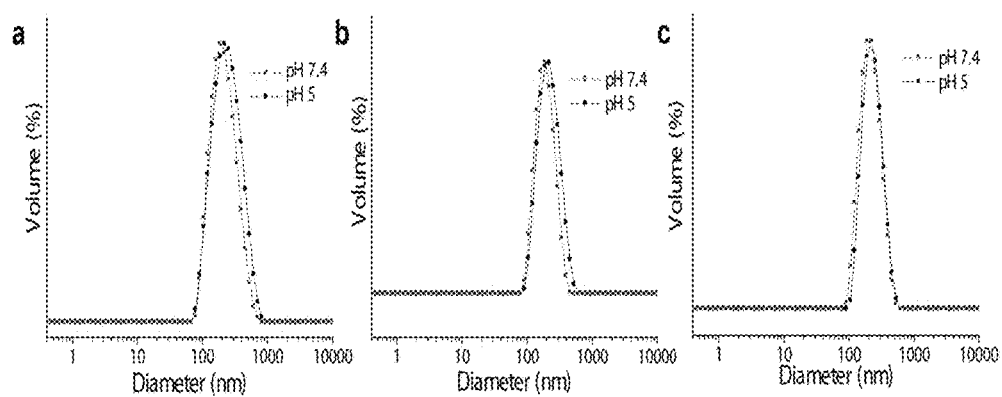
FIG. 16 shows exemplary DLS of nanogels (a) NG1, (b) NG2, and (c) NG3 at pH 7 and 5.
Figure 17:
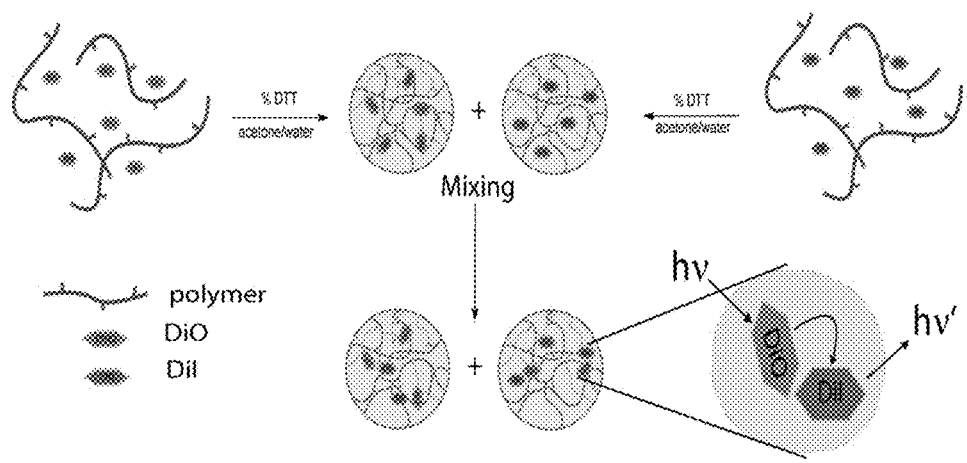
FIG. 17 shows a schematic illustration of an embodiment of using of the fluorescent carbocyanine dyes DiI and DiO.

To test the in vitro release of guest molecules, nanogels having DiO and DiI co-encapsulated within their interiors were used. In this case, if there were no guest release upon cellular internalization, then FRET would be continually observed within the cytosolic interior. However, if the guest release did occur, then the proximity between the DiO and DiI would greatly increase, causing a qualitative decrease in FRET observation. The distribution of red (FRET, 585-615 nm spectral filter) and green (no FRET, 505-520 nm spectral filter) fluorescence was observed over time by confocal microscopy ($\lambda_{ex}$=488 nm). FIG. 8 shows the fluorescence microscopy images. After 2 h, neither of the nanogels had gained significant access to the cells (FIGS. 8a and 8d). Most of the red fluorescence was found in the extracellular environment. The observed red fluorescence suggests that the dye molecules are still intact in the polymer nanoparticles. In the case of NG1 (6% crosslinked), green color begins to appear in the cell membrane with a little red color inside the cell after an incubation period of 4 h (FIG. 8b). The green fluorescence (DiO) in the plasma membrane suggests an initial loss of FRET due to hydrophobic dye transfer from the nanogels to the membrane. As time progresses, the extent of fluorescence (both green & red) increases; the observed yellow color is essentially an overlay of the two colors. After accessing the cell, the green fluorescence from DiO and the red fluorescence from DiI appear more equally inside the cells. This indicates that there is a significant release of the dye molecules from the nanogel, because there is no energy transfer that causes the green fluorescence to be suppressed. While the lightly cross-linked gel, NG1, shows initial dye release from the nanogels to plasma membrane before cellular internalization, the highly crosslinked NG3 exhibits complete internalization prior to any significant release. This difference is clearly observed in FIG. 8e, which shows an abundance of red color and a little yellow color inside the cell with no green color at the membrane after 4 h incubation. At 24 h incubation, the intensity of yellow color increased, but the dominant red color indicates slower release due to the dense cross-linking (FIG. 8f). However, after 48 h of incubation yellow color dominates the image implying the progression of nanogel disruption and subsequent dye release (FIG. 14).

After entry, the less crosslinked nanoparticle NG1 releases the dye molecules faster than the more crosslinked NG3. It is evident from FIG. 8 that the difference between the green and the red fluorescence from these cells is much smaller in the case of NG1, compared to NG3. These results indicate that the intracellular GSH acts on NG1 faster than NG3, just as observed with the Nile red release studies outlined above, and are consistent with the dye release differences depending on crosslinking density from the nanogels to the DOPC bilayer. Importantly, these results demonstrate the tunability in stability of encapsulation and guest release in cells. Also, the cell penetrating processes can be accelerated using ligands that facilitate internalization by recognizing cell surface receptors. (Ryu, et al. 2010 *J. Am. Chem. Soc.* 8246-8247.)

Intracellular Delivery of Doxorubicin

Figure 9:
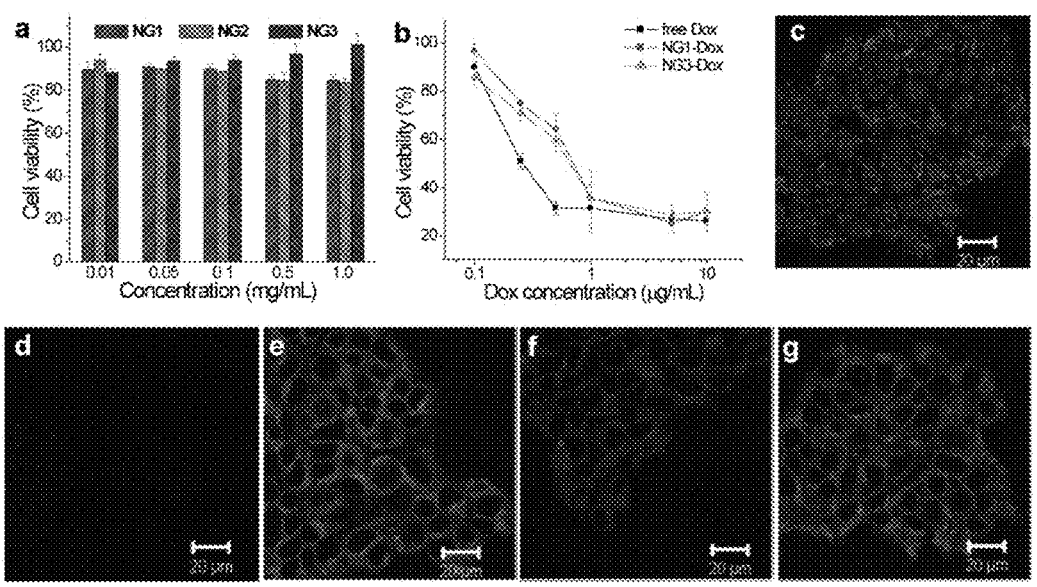
FIG. 9 shows: (a) Exemplary in vitro toxicity of empty nanogels with 293T cells after 24 h incubation; (b) Dox-loaded nanogels with MCF-7 cells after 72 h incubation; Confocal microscopy images of (c) free-Dox after 3 h; NG1-Dox after (d) 3 h and (e) 4 h; NG3-Dox after (f) 3 h and (g) 4 h.
Figure 10:
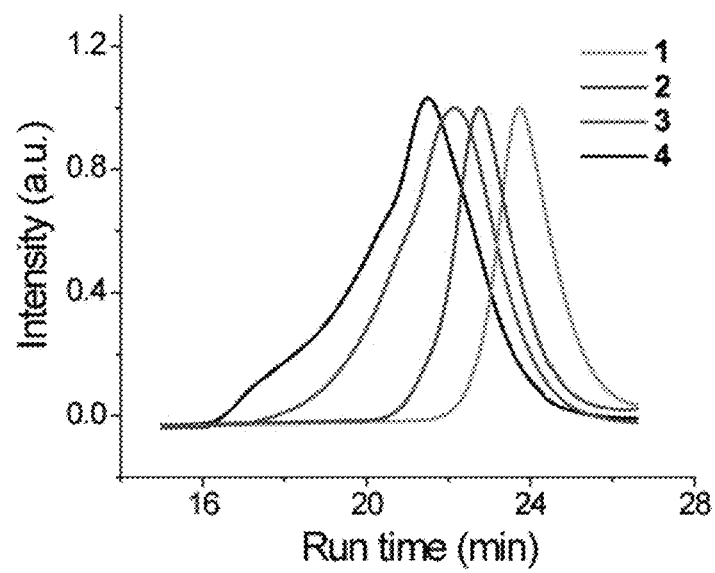
FIG. 10 shows exemplary GPC traces of polymer 1-4.

In vitro cell viability assays were carried out for the polymer nanoparticles prepared above. The nanoparticles are expected to be relatively non-toxic, as they are composed of biocompatible OEG units as surface displays in a methacrylate backbone. Cell viability was investigated by treating 293T human kidney cell lines with nanogels. 293T cells were treated with different concentrations of nanogel solutions and were incubated for 24 h. Cell viability was measured using the Alamar Blue assay. As shown in FIG. 9a, the nanogels exhibit high cell viability and no concentration dependent toxicity up to a nanogel concentration of 1 mg/mL. This result indicates that the nanogel material is non-toxic and thus a potential candidate for biological applications.

To investigate the utilization of the polymer nanoparticles as drug delivery vehicles, the chemotherapeutic cytotoxic drug molecule, doxorubicin (Dox), was encapsulated during nanogel synthesis by in situ loading. The loading capacities were found to be 24 wt % and 20 wt % for NG1 and NG3, respectively. The Dox-loaded nanogels were added to MCF-7 cells and the extent of cell death was investigated after 72 h. As shown in FIG. 9b, the Dox-loaded nanoparticles were toxic, but exhibited slightly lower toxicities than the free drug. This is presumably caused by the delayed release of Dox from the nanogels inside the cells, while free Dox molecules easily diffuse through the cellular membrane. Compared to small drug molecules, however, the nanogels are likely to be more efficient in vivo because of the passive targeting of the nanosized particles to tumor tissue by the enhanced permeability and retention effect.

Interestingly, both NG1 and NG3 containing Dox showed similar toxicity although it was expected that NG1-Dox would be more toxic than NG3-Dox because, as described above, the lightly crosslinked NG1 showed faster dye release in the cell as well as in buffer solution. One possible explanation is a difference in the cellular uptake between the nanoparticles of different crosslinking densities. (You, et al. 2009 *Nano Lett.* 9, 4467-4473; Beningo, et al. 2002 *J. Cell Sci.* 115, 849-856.) Differences in uptake were previously observed by in situ dye release experiments. As shown in FIGS. 8b and 8e, NG3 exhibited higher cellular uptake relative to NG1 at the same time period.

For further study, the cell uptake of both free Dox and Dox-loaded nanogels (20 μM Dox concentration) was monitored using confocal microscopy over time. Initial internalization of Dox was observed within 3 h for free Dox and NG3-Dox, but not until 4 h for NG1-Dox (FIG. 9c-g). While the free Dox showed significant accumulation in the nucleus after 3 h (FIG. 9c), NG1-Dox and NG3-Dox only showed strong fluorescence in the cytoplasm (FIG. 9e-g). Even though NG1 exhibited faster dye release in previous experiments, the effective Dox amount released from NG3 may be similar to that from NG1 due to the differences in cellular uptake. This is presumably the reason that the two nanogels show similar toxicities.

Pentafluorophenyl Activated Esters and Bifunctional Cross-Linkers

Figure 18:
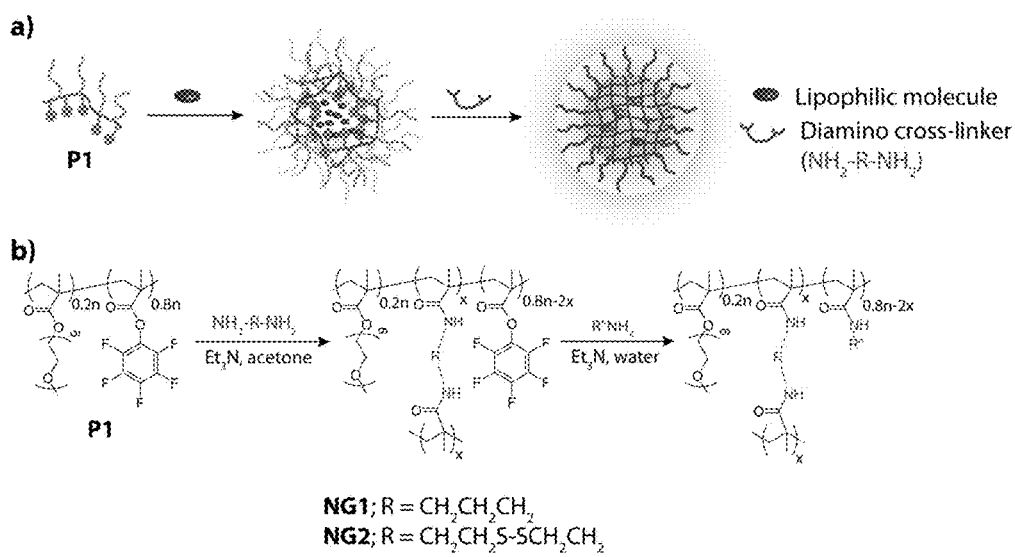
FIG. 18 shows a schematic illustration of an embodiment of the nano-assemblies of the invention. (a) Schematic representation of the preparation of bifunctional cross-linked nanogels. (b) Synthesis of cross-linked nanogels from P1' to make NG1' and NG2'.

Pentaflurophenyl (PFP) has been used as handles for post-polymerization modification with a variety of functional amines. (Eberhardt, et al. 2005 *Eur. Polym. J.* 2005, 41, 1569-1575; Jochum, et al. 2009 *Macromolecules* 42, 5941-5945; Roth, et al. 2008 *Macromolecules* 41, 8513-8519.) While the amidation of PFP is similar to that of the N-hydroxy-succinimide (NHS) activated ester, PFP is relatively more hydrophobic and exhibits high-hydrolytic stability, providing possibilities of running the reaction in either organic solvent or aqueous solution. (Gibson, et al. 2009 *J. Polym. Sci. Part A: Polym Chem* 47, 4332-4345.) The desired polymer precursors contain poly(ethylene glycol) as a hydrophilic unit and pentafluorophenyl ester as a hydrophobic unit (FIG. 18b). The hydrophobic nature of the PFP units drives the polymer precursors to form stable self-aggregates, offering lipophilic encapsulation capabilities. Additionally, the PFP activated esters are known to be replaced with amines with great efficiency. Therefore, the addition of diamine cross-linkers to the stable PEG-PFP polymer aggregates may result in stable cross-linked polymer nanogels, in which lipopohilic molecules can be trapped.

A key feature involves the utility of an amphiphilic random copolymer, where the reactive lipophilic functional groups are utilized for crosslinking. In this case, pentafluorophenyl moiety is used as the lipophilic functional group that provides such reactivity. Random copolymers were prepared containing polyethylene glycol methacrylate (PEGMA) as the hydrophilic unit and the pentafluorophenyl acrylate (PFPA) as the lipophilic unit. Addition of a calculated amount of diamine to a solution of the PPFPA-r-PEGMA random copolymer causes inter- and intra-chain crosslinking amidation reactions to afford the nanogel. Since only a percentage of the PFP moiety is used for the cross-linking reaction, the remaining reactive PFP functionalities can be used for surface functionalization.

Amphiphilic random copolymers (P1') containing 20% biocompatible, water soluble poly(ethylene glycol) monomethyl ether (PEG) monomers and 80% hydrophobic pentafluorophenyl activated ester monomers were synthesized by RAFT polymerization. The resulting polymer was obtained by precipitation and had a molecular weight of $M_n$=12700 g/mol with a narrow molecular weight distribution (PDI=1.17). Polymer nanogels were prepared from random copolymer P1' (20 mg/mL in acetone) by the addition of diamine cross-linkers, including diaminopropane (DAP) and cystamine (CYS or CTM), to initiate cross-linking of the PEG-PFP polymer aggregates. Subsequent addition of water and gradual evaporation of the acetone yielded nanogels NG1' and NG2' respectively (FIG. 18b). The sizes of the nanogels dispersion in water were observed by DLS measurements. At 20 mg/mL, the sizes were observed to be concentrated at 110 nm in both water and acetone. Upon dilution of the resulting nanogels to 2 mg/mL in acetone, the sizes retained at 110 nm, while the sizes of the precursor polymer aggregates diluted to the same concentration were observed to decrease significantly to around 10 nm. The lack of concentration dependence of the sizes of the nanogels in both water and acetone suggests that these are stable, cross-linked particles. If the formation of these nanogels occurs from preformed polymer aggregates, the concentration of polymer precursors would affect the obtained particle size. Indeed, smaller particles (~10 nm) were prepared by decreasing the concentration of P1' to 10 mg/mL during the preparation reaction.

Figure 19:
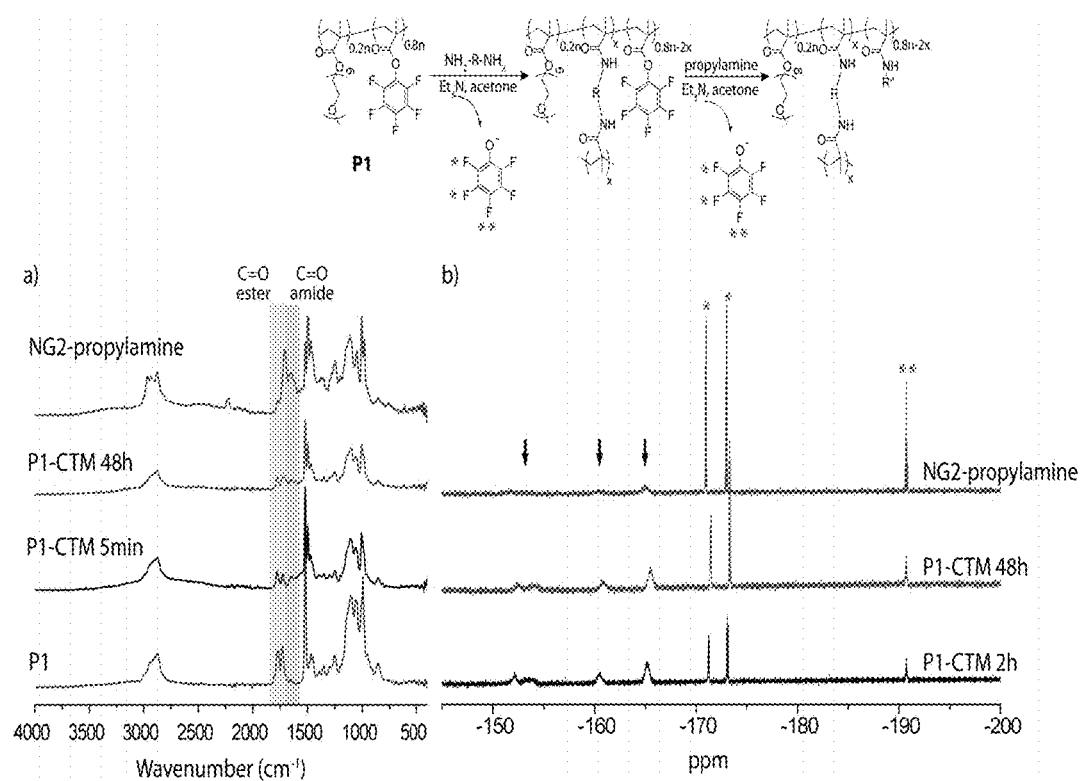
FIG. 19 shows: (a) exemplary IR spectroscopic data and (b) $^{19}$F NMR spectra of the synthesis of cross-linked polymer nanogels: reaction of P1' and CYS at 2 hours (black); 48 hours (red); reaction of NG2' and propylamine (blue).

The amidation of PFP activated esters within the polymer scaffold with diamine cross-linkers was confirmed by FTIR and $^{19}$F NMR (FIG. 19). Tracing the absorption spectra observed by FTIR reveals that the carbonyl of PFP ester band clearly shifts from v=1780 cm$^{-1}$ to 1660 cm$^{-1}$ over time, indicating amide bond formation from reaction of the PFP ester units with the cross-linking functional amines. The additional advantage of the using the PFP ester functionality is that analysis of the reaction progress can be easily monitored by $^{19}$F NMR spectroscopy as shown in FIG. 19b. The $^{19}$F NMR spectrum of the P1' precursors shows four signals at 151.0, 152.6, 159.3, and 164.1 ppm that can be assigned to PFP ester units. After adding the DAP and CYS cross-linkers to cross-link P1', achieving NG1' and NG2' respectively, the evolution of three new sharp peaks of the pentafluorophenol leaving groups at 170.4, 172.3, and 190.7 ppm indicates progress of the PFP conversion reaction. The remaining PFP activated ester groups provide the possibilities for post-modification of the nanogels with molecules containing amine functionalities. To test this, an excess amount of propylamine was added to NG1' and NG2' to displace the residual PFP units. These post-modified nanogels were confirmed by FT-IR and $^{19}$F NMR. The disappearance of the absorption of the carbonyl ester band at 1780 cm$^{-1}$ and the appearance of the carbonyl amide band at 1660 cm$^{-1}$ suggest that the remaining PFP esters were completely converted to propylamide functional groups. The progress of the amidation reaction was also monitored by tracking the release of the petafluorophenol byproduct. The increase of pentafluorophenol signals observed by $^{19}$F NMR further confirms that replacement of PFP esters with propylamine can be achieved under mild reaction conditions.

To investigate the possibility of encapsulating lipophilic guest molecules within the formed cross-linked nanogels and to evaluate the encapsulation stability observed in such a carrier scaffold, the FRET based method employed above was used. In this experiment, the lipophilic FRET pair dyes, DiO (DiOC18(3), FRET donor) and DiI (DiIC18(3), FRET acceptor), were independently loaded into separate nanogel solutions.

Aqueous solutions of NG1' and NG2' (2 mg/mL) containing 1 wt % of either DiO or DiI were prepared from P1' (10 mg/mL) stock solution, represented as NGx-DiI and NGx-DiO where x=1' and 2'. The solutions containing the separate dyes were then mixed in water (at 10 times dilution). Fluorescence from DiO excitation at 450 nm was monitored over time. Analysis of the linear fit to the first 6 hours of data revealed leakage coefficients (Λ) of ~0.009 h$^{-1}$ and 0 h$^{-1}$ for NG1' and NG2', respectively suggesting that the nanogels exhibit high encapsulation stabilities.

Figure 20:
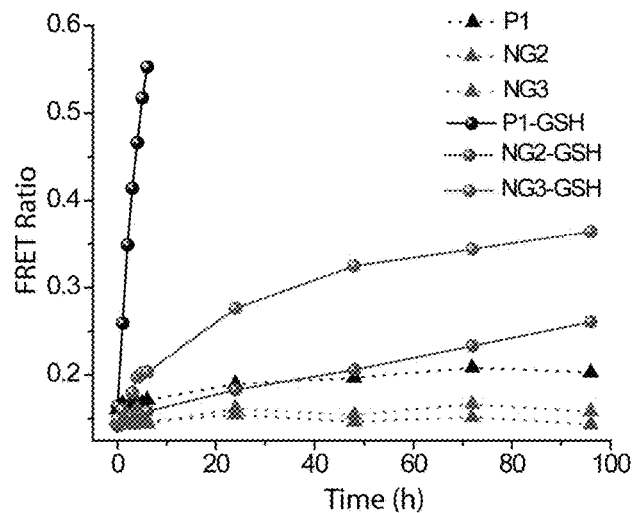
FIG. 20 shows exemplary encapsulation stabilities of P1' (black), NG2' (blue), and NG3' (red) in the presence of GSH (solid line) and absence of GSH (broken line).

The FRET evolution of a NG2'-DiO and NG2'-DiI mixed solution in the presence of 10 mM GSH was traced. The resulting increase of the FRET ratio observed over a 96 hour periods suggests that the encapsulation stability of NG2' decreases upon disulfide bond cleavage, leading to the leakage or release of the encapsulated dyes molecules (FIG. 20). To test tenability of the encapsulation stability and release rate, NG3' was prepared at lower cross-linking densities by decreasing the CTA feeding amount to 0.1 mol % with respect to the P1' precursors. Dye exchange with NG3' in the presence of GSH, as observed by the FRET based experiments, is faster than the higher cross-linked NG2'. P1' aggregates in water also show high encapsulation stability with Λ=0.001 h$^{-1}$. However, P1' aggregates in the presence of 10 mM GSH exhibit dramatically increased of FRET with Λ=0.064 h$^{-1}$, which is higher than what was observed in the cross-linked nanogels. Note that GSH is a tripeptide that contains a primary amine. Thus, GSH can react with PFP units causing changes in the hydrophobic-lipophilic balance (HLB) of the polymer aggregates and leading to a loss of encapsulation stability due to increase solubility of the polymer chains.

Figure 21:
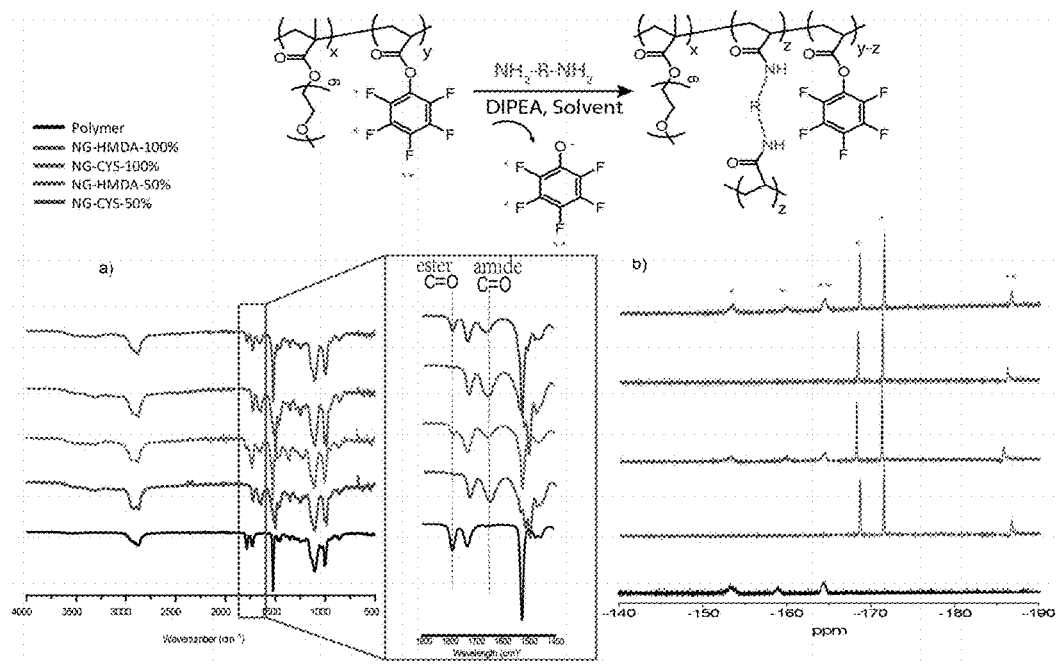
FIG. 21 shows exemplary characterization of cross-linking in the presence of hexamethylenediamine and cystamine: (a) amidation monitored by FTIR; (b) release of pentafluorophenyl groups tracked by $^{19}$F-NMR.

In another example, cross-linked nanogels with 50% and 100% cross-linking density (with respect to the PFP units) were prepared from a PPFPA-r-PEGMA solution (10 mg/mL in THF) by adding a calculated amount of CYS and hexamethylenediamine (HMDA) followed by the addition of water and evaporation of THF. Reaction between the amine the activated ester results in the formation of the amide bond and the concurrent release of the PFP moiety in the form of pentafluorophenol (FIG. 21). IR spectra of reaction mixtures, listed in FIG. 21a, were recorded after heating at 50° C. for 4 h. The peak at 1780 cm$^{-1}$, corresponding to the activated ester C=O stretching, disappeared with the concurrent appearance of the peak at 1640 cm$^{-1}$ ascribed to the amide C=O stretching. When 0.25 eq. of cross-linker was used, half of the PFP esters were converted to amide. The remaining PFP activated ester C=O signal can still be observed.

Figure 22:
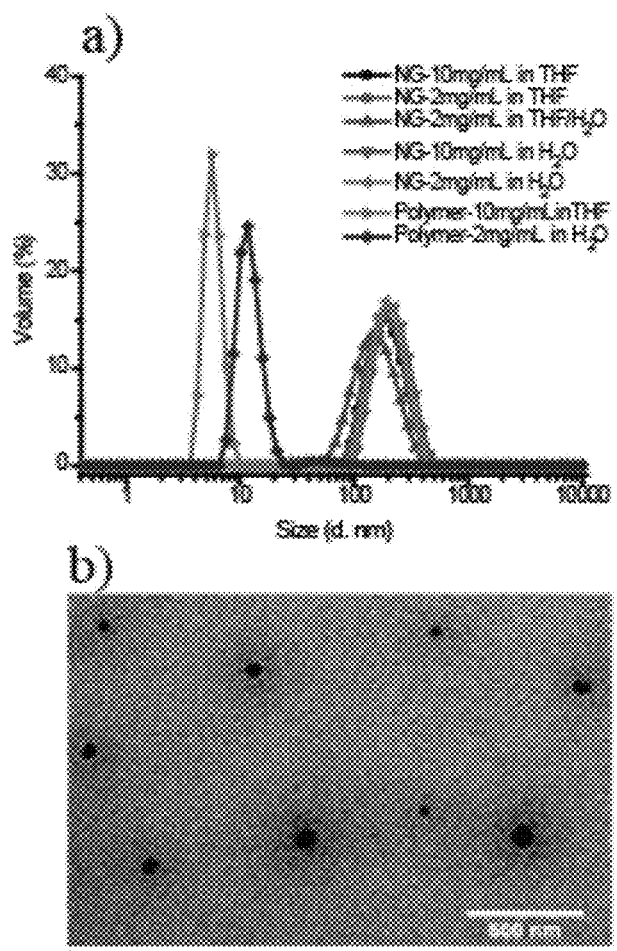
FIG. 22 shows exemplary (a) Size distributions of nano-gel cross-linked by CYS, and then re-dispersed in different solvents with various concentrations; (b) TEM image of nanogel; The scale bar is 500 nm.
Figure 29:
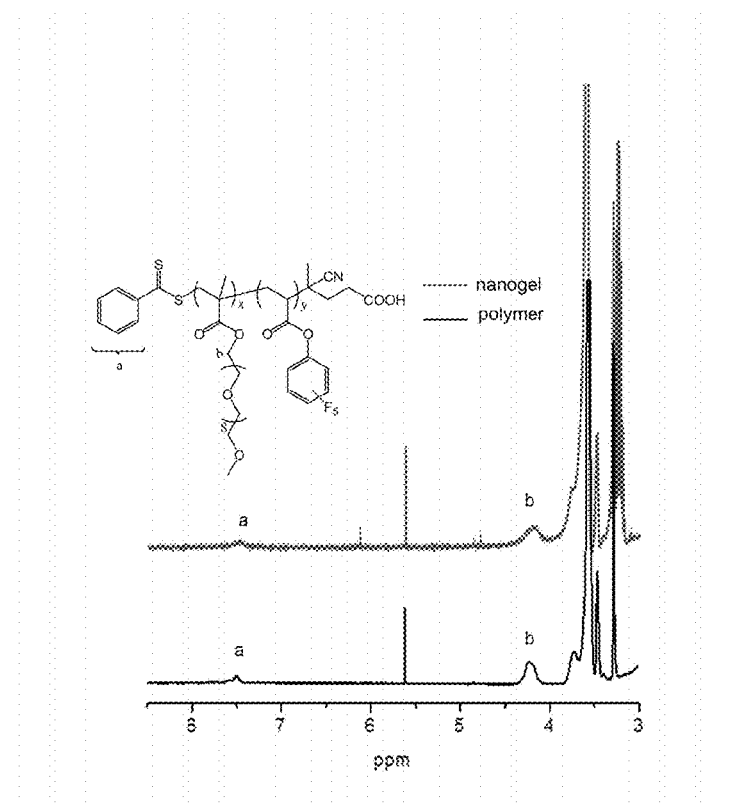
FIG. 29 shows exemplary end group analysis for polymer and nanogel by $^1$HNMR.

The $^{19}$F NMR spectrum of the polymer (FIG. 21b) shows three broad peaks at −153.4, −159.9, and −164.3 ppm. After adding CYS or HMDA cross-linkers, the polymer was cross-linked to affording nanogels, releasing $C_6F_5OH$ groups, which show sharp signals located at −168.5, −171.4 and −186.6 ppm. The broad peaks fully disappeared with the addition of 0.5 eq. of cross-linker, suggesting 100% cross-linking density in yielded nanogels. The remaining broad peaks and new sharp peaks are simultaneously observed when 50% of the PFP groups were cross-linked. The dramatic change in chemical shift indicates the conversion from activated ester to amide and hence cross-linking. Additionally, end group analysis by $^1$H NMR reveals that most of end groups remain intact after cross-linking (FIG. 29). The size of the nanogels prepared from a 10 mg/mL polymer solution in THF with CYS were measured by DLS shown in FIG. 22.

Figure 27:
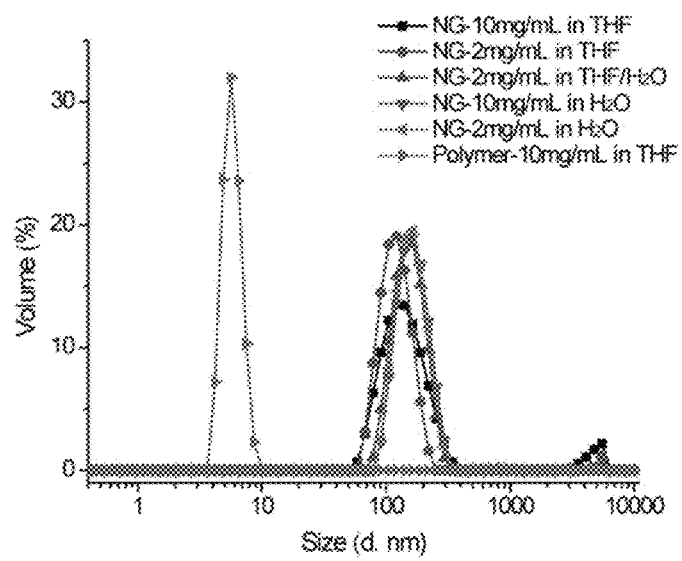
FIG. 27 shows exemplary size distribution of nanogel cross-linked by HMDA and dispersed in different solvents.

The size of the nanogel dispersion in water was ~180 nm, which is coincident with what was observed from TEM. In order to show that the synthesized nanogels are stable cross-linked networks, rather than the simple aggregation of the polymer, nanogels were re-dispersed in THF and a THF/H$_2$O mixture at various concentrations and were compared. Sizes of the same nanogel dispersed in THF or THF/H$_2$O mixture are similar to that in H$_2$O alone. Also, dilution of the nanogels to 2 mg/mL in THF or H$_2$O does not result in a size change (remains at ~180 nm). However, the same dilution of the polymer aggregates, prior to the cross-linking reaction, reduces the aggregate sizes to ~13 nm. These results suggest that the nanogel is from a covalently crosslinked network and has no concentration and solvent dependency. A similar result was observed from the nanogel cross-linked by HMDA (FIG. 27). Although PPFPA-r-PEGMA dissolved in THF shows peaks at around 10 nm, the poor correlation function is taken to indicate ill-defined aggregation. Since the nanogel sizes are much larger than the aggregate sizes of PPFPA-r-PEGMA in THF, there is some inter-aggregate crosslinking under these reaction conditions.

Figure 23:
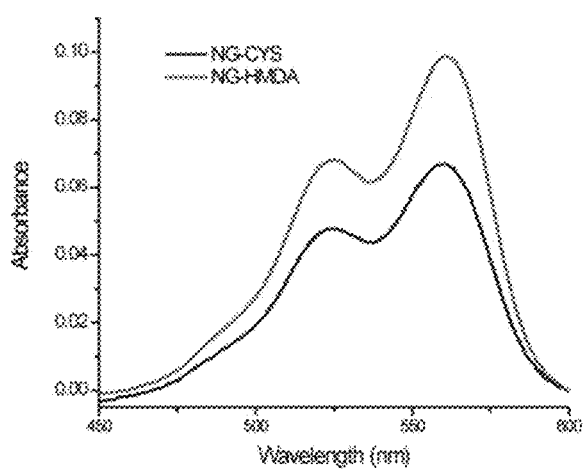
FIG. 23 shows exemplary absorbance of nanogel respectively cross-linked by CYS and HMDA and loaded with DiI. Concentration of both measured nanogel solution is 0.2 mg/mL.

A lipophilic guest molecule, DiI was encapsulated in nanogels during cross-linking. During this encapsulation, 1 wt % of DiI with respect to polymer was initially fed. Guest molecule encapsulation was measured by absorbance spectroscopy shown in FIG. 23.

Figure 24:
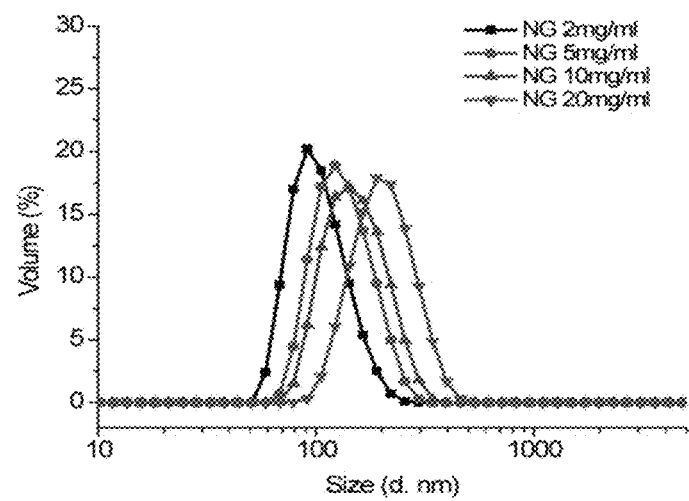
FIG. 24 shows exemplary size of nanogels prepared in a variety of PPFPA-PEGMA concentrations.

Nanoparticle size is known to play a significant role in several applications. For example, in the case of drug delivery, size has impact on biodistribution, cellular uptake, and permeability in disease sites, thus affecting the therapeutic efficacy. (He, et al. 2010 *Biomaterials*, 31, 3657; Balogh, et al. 2007 *Nanomed-Nanotechnol*, 3, 281; Wong, et al. 2011 *Natl Acad Sci USA*, 108, 2426.) Larger nanogel size is a result of small percentage of inter-aggregate cross-linking in addition to the desired intra-aggregate crosslinking. The inter-aggregate phenomenon is expected to be highly concentration dependent. Hence, the nanogel size would be significantly affected by the original concentration of the PPFPA-r-PEGMA solution. Four nanogels were prepared from 2 mg/mL, 5 mg/mL, 10 mg/mL and 20 mg/mL PPFPA-PEGMA solution in THF. As shown in FIG. 24, the size of the nanogel dispersed in $H_2O$ shifts from 100 nm to 200 nm along with the increase in PPFPA-PEGMA concentration.

Preparing the nanogels directly in water offers several advantages: (i) the organic solvent free nanocarrier preparation method is much preferred in terms of removing the trace amounts of solvent and its environment-friendly nature; (ii) allows for an additional handle to tune the particle size; (iii) allows for efficient incorporation of a broader range of lipophilic guest molecules within the nanogels. (Nilles, et al. 2011 *Polym. Chem.* 2, 376; Gibson, et al 2009 *J Polym. Sci. Pol. Chem.* 47, 4332.)

Figure 25:
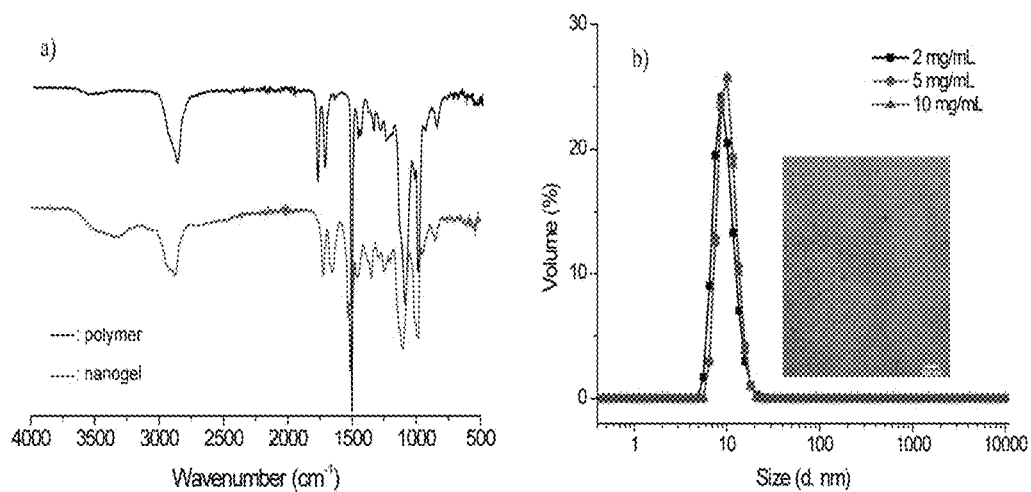
FIG. 25 shows exemplary synthesis of nanogel in $H_2O$: (a) Cross-linking followed by FTIR; (b) Size of nanogel prepared from 2 mg/mL, 5 mg/mL, 10 mg/mL of PFPA-PEG solution in $H_2O$; Inset is TEM image of nanogel where the scale bar is 100 nm.

Nanogels were prepared in aqueous solutions using a PPFPA-r-PEGMA solution at a variety of polymer concentrations. The cross-linking reaction in $H_2O$ was also detected by FTIR. The collected FTIR spectrum of the aqueous reaction mixture after 4 h heating was shown in FIG. 25a. No remaining PFP groups were observed after cross-linking, indicated by the complete disappearance of the activated ester C=O absorbance. Evolution of a peak at 1640 $cm^{-1}$ further confirms the amidation. Another potential issue is the extent to which the PFP activated ester was converted to amide, compared to the potential hydrolysis of the ester during the cross-linking process. This can be addressed by monitoring the IR spectrum. The absorbance of the poly methacrylic acid, the product of hydrolysis, should be observed if hydrolysis occurred during the cross-linking process. However, no significant evidence was observed for the hydrolysis peak, which is expected to be at around 1710 $cm^{-1}$. (Billingham, et al. 1997 *Vibrational Spectroscopy*, 14, 19; Arndt, et al. 1999 *Acta Polym.* 50, 383; Dubinsky, et al. 2005 *J. Polym. Sci. Polym. Phys.* 43, 1168.) This suggests that cross-linking is the predominant reaction. Interestingly, the sizes of the nanogels prepared in $H_2O$ were around 10 nm independent of the concentration of PPFPA-PEGMA solutions used. Size measurements from DLS are in good agreement with the TEM results shown in FIG. 25b.

The residual PFP moieties can be utilized to additionally functionalize the surface of the nanogels, providing at least two key advantages: (i) this post-nanogel formation reaction can be used to eliminate the remaining reactive PFP moieties. This is useful in applications such as drug delivery, where the reactivity of the PFP moiety could be a source of toxicity; (ii) this allows for the incorporation of functionalities on the surface of the nanogels. An example of an implication of such a capability includes incorporation of ligands for sensing and targeted delivery.

Figure 26:
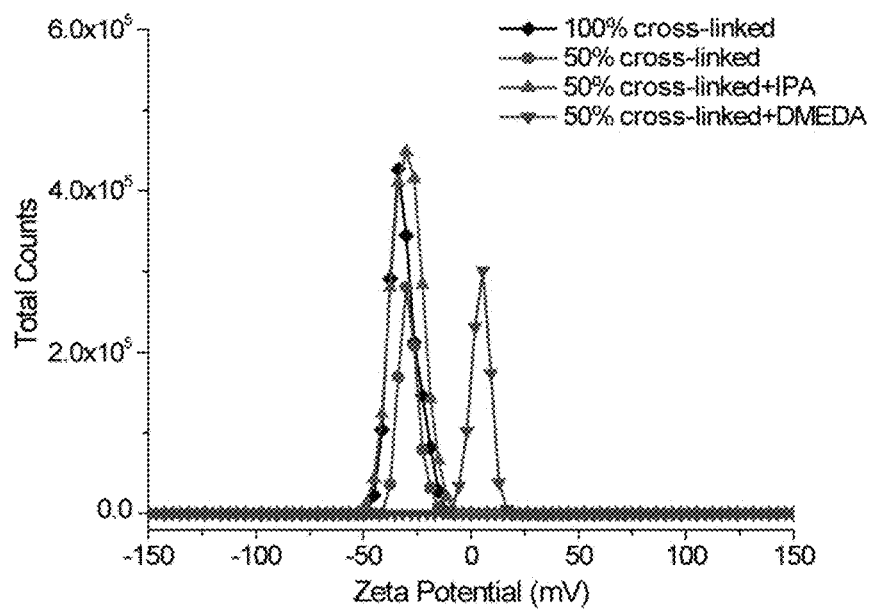
FIG. 26 shows exemplary charged surface of nanogels without and with post-nanogel modification.
Figure 28:
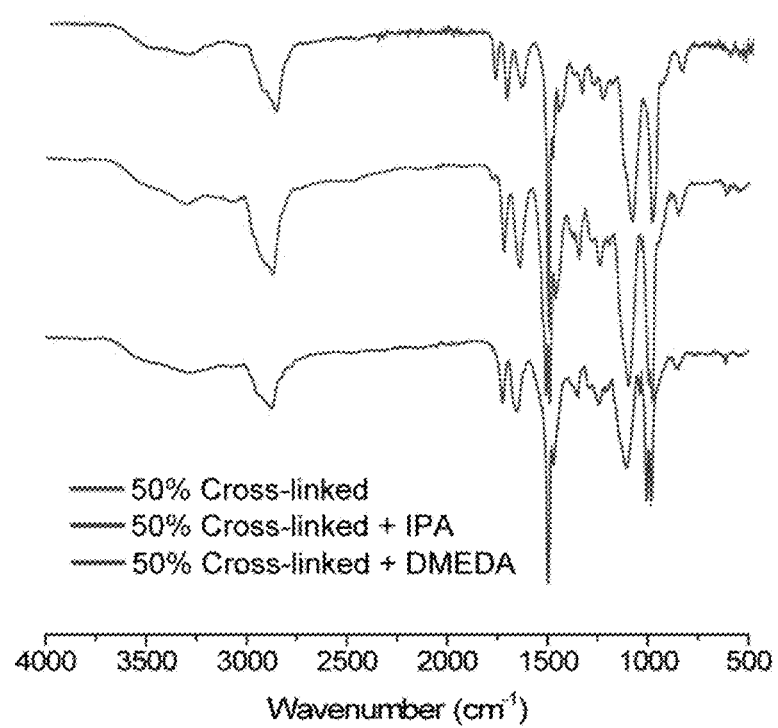
FIG. 28 shows exemplary FTIR spectrum of nanogel and nanogel modified by isopropylamine (IPA) and N,N-dimethylethylenediamine (DMEDA).

In order to demonstrate the possibility of surface engineering on these nanogels, isopropylamine (IPA) and N,N-dimethylethylenediamine (DMEDA) were incorporated onto the 50% crosslinked nanogel after the nanogel synthesis. This reaction with IPA and DMEDA was monitored by FTIR (FIG. 28), which clearly indicates that the amidation step can indeed be carried out in the post nanogel synthesis steps. Moreover, zeta potentials of these nanogels were measured to obtain additional evidence for surface modification (FIG. 26). Zeta potentials of the 50% and 100% cystamine crosslinked nanogels were around −30 mV. Similarly, the 50% cross-linked nanogel modified by IPA also has a zeta potential of −30 mV. The observation of negatively charged nanogel surface is surprising. However, when the nanogel was modified by DMEDA, the zeta potential was found to shift to +5 mV. The positively charged surface is attributed to the protonation of DMEDA and therefore taken to designate surface modification. The presence of these functionalities on the nanogel surface can also be presumed, because prior studies with the disulfide crosslinked nanogels show that cell penetrating peptide ligands are indeed available on the surface after a similar functionalization step. (Ryu, et al. 2010 *J. Am. Chem. Soc.* 132, 8246.)

Thus, the invention provides a facile methodology to achieve polymeric nanogels using a simple reaction between the lipophilic activated PFP ester and diamines. This strategy has an advantage that the syntheses of nanogels are not limited to disulfide crosslinked systems or self-crosslinking reactions. The intermolecular nature of the crosslinking reaction allows for incorporating a broader variety of stimuli-sensitive features in the diamine crosslinkers and thus in the nanogel. Advantages of the disclosed approach include: (i) there is significant tunability in the size of the nanogels, especially in THF; (ii) these nanogels can encapsulate lipophilic guest molecules during the crosslinking step of the nanogel synthesis; (iii) the nanogels are dispersible in water, irrespective of whether they were prepared in THF or water; (iv) residual PFP moiety can be used in a post-nanogel assembly step to incorporate surface functionalities.

Concurrent Binding and Delivery of Proteins and Lipophilic Small Molecules

Nanoscale vehicles are desired that can concurrently sequester and deliver two different molecules. (Kelkar, et al. 2011 *Bioconjug. Chem.* 22, 1879-1903; Kelkar, et al. 2011 *Acc. Chem. Res.* 44, Issue #10; Jain 2001 *Nature Med.* 7, 987-989; Sengupta, et al. 2005 *Nature*, 436, 568-572.) It is less challenging when two lipophilic or two hydrophilic molecules are co-sequestered and delivered. It is much more difficult and complicated when a combination of a water-soluble hydrophilic molecule and a water-insoluble lipophilic molecule are to be co-encapsulated and delivered, especially so when one of the cargos is a protein. The propensity of proteins to irreversibly denature under non-native conditions presents a significant challenge. (Kim, et al. 2009 *Langmuir* 25, 14086-14092; Kim, et al. 2011 *Mol. Pharmaceutics* 8, 1955-1961; Wiradharma, et al. 2009 *Biomaterials* 30, 3100-3109.)

Figure 30:
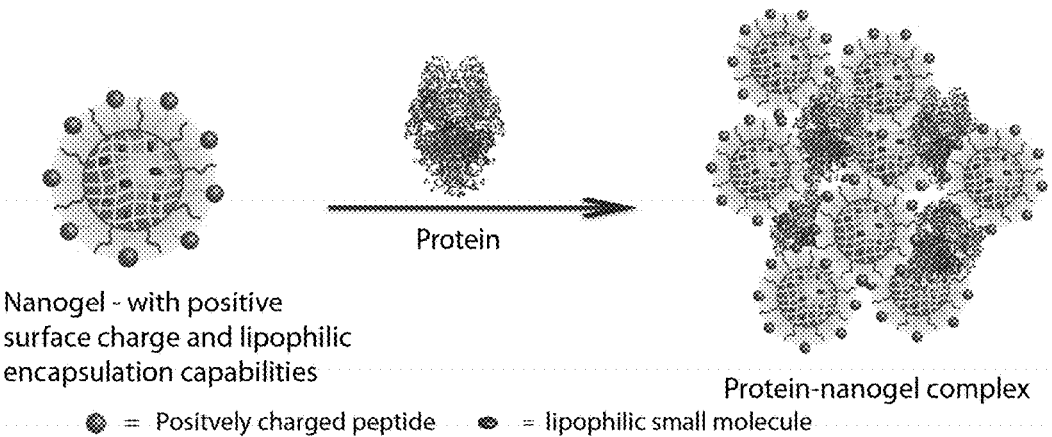
FIG. 30 shows exemplary nanogel-protein complexation by complementary electrostatic interactions.

As schematically illustrated in FIG. 30, the invention utilizes the hydrophobic interior of a polymer assembly to stably encapsulate lipophilic guest molecules, while utilizing the complementary electrostatic interaction between the surface of the polymer assembly with a peptide to bind proteins. β-galactosidase (β-gal, pI: 4.8, from *E. coli*) is used as the model protein for testing, which offers the benefit of studying the activity of this enzyme both inside and outside the cells. DiI dye is used as the model small molecule, which is lipophilic and exhibits fluorescence characteristics (complementary to the fluorescein labeling of the protein) allowing for concurrent monitoring of the protein and the small molecule in solution and inside the cells. Self-crosslinked nanogels of the invention are used as the nanocarrier, which offer the capabilities for stably encapsulating lipophilic dye molecules. (Ryu, et al. 2010 *J. Am. Chem. Soc.* 132, 17227-17235; Jiwpanich, et al. 2010 *J. Am. Chem. Soc.* 132, 10683-10685.)

Two nanogels, NG1 and NG2, were prepared with 6% and 14% crosslinking densities respectively. As provided herein, the nanogels were prepared from a random copolymer, obtained using a hydrophilic oligoethyleneglycol methacrylate and a lipophilic methacrylate monomer containing a PDS moiety. The self-assembled structure was "locked in" with the non-covalently sequestered lipophilic guest DiI molecules by initiating a thiol-disulfide exchange reaction among the PDS units using DTT. (Jiwpanich, et al. 2010 *J. Am. Chem. Soc.* 132, 10683-10685.) The extent of crosslinking was controlled by the amount of DTT added to the reaction mixture.

Figure 31:
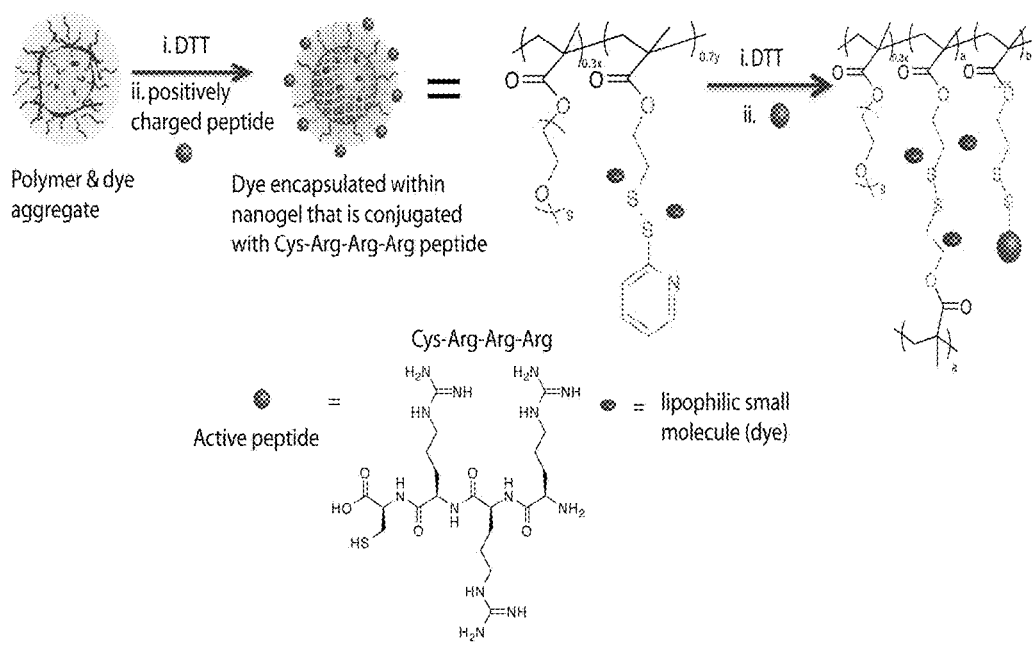
FIG. 31 shows exemplary structures of the nanogel's polymer precursor and tri-arginine peptide.

The surface of this nanogel contained charge-neutral functional groups. Positively charged functional groups, tri-arginine, were introduced to bind to the negatively charged surface of β-gal. This tripeptide can perform the dual role of providing the positive charge and also exhibiting cell-penetrating peptide characteristics. (Rothbard, et al. 2004 *J. Am. Chem. Soc.* 126, 9506-9507; Nakase, et al. 2008 *Adv. Drug Deliv. Rev.* 60, 598-607.) Since only a small percentage of the PDS groups were used for the crosslinking reaction, the residual PDS moieties conjugated the tri-arginine moiety using a Cys-Arg-Arg-Arg (CRRR) peptide. Here, the thiol moiety in cysteine reacts with the PDS units to provide the targeted nanogel. The structures of the nanogel's polymer precursor and the CRRR peptide are shown in FIG. 31.

Figure 36:
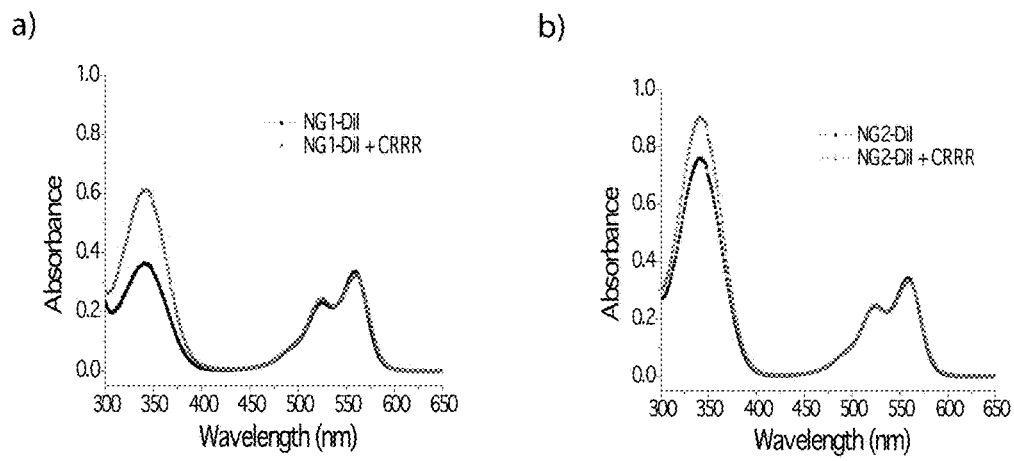
FIG. 36 shows exemplary absorbance of: (a) NG1 (10 mol % DTT) and (b) NG2 (20 mol % DTT) before and after modification with CRRR peptide.
Figure 37:
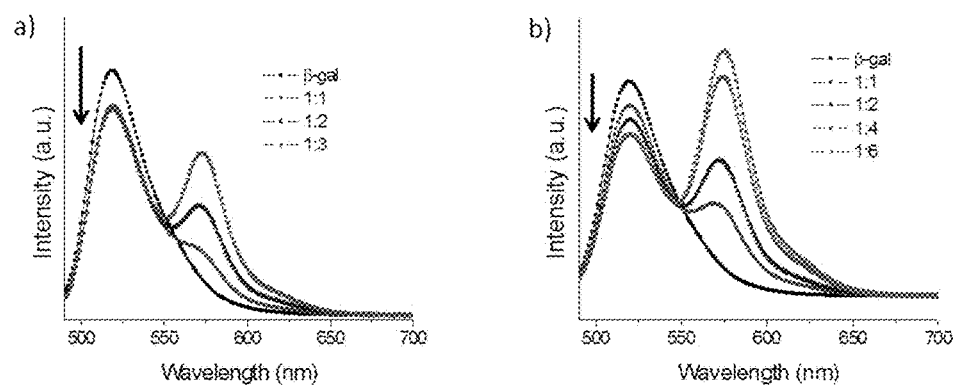
FIG. 37 shows exemplary fluorescence emission change of FITC labeled β-gal and encapsulated DiI in (a) NG1-CRRR and (b) NG2-CRRR varying nanogel ratios.

In the nanogel formation process, NG1 showed only a small amount of production of pyridiothione (the byproduct of disulfide crosslinking) at 330-340 nm. On the other hand, NG2 showed a large amount of pyridiothione release indicating that NG2 is more densely crosslinked (FIG. 36). Subsequent CRRR addition showed a further increase in the absorption peak of pyridiothione, indicative of peptide conjugation onto the surface of the nanogels. The same amount of CRRR addition showed a smaller increase for NG2 compared to NG1. This means that the degree of modification with CRRR peptide is much more for NG1 than for NG2. This is because the remaining PDS groups for surface modification after nanogel formation are less at high crosslinking densities. Thus, the two nanogels have different degrees of surface functionalization, which should have implications in protein binding and delivery. The absorption intensity of hydrophobic dye, DiI, did not change during the surface modification step, indicating that peptide modification process doesn't affect the encapsulation stability of the hydrophobic guest in the nanogel.

Next, β-gal functionalized with fluorescein (FITC-β-gal) was used to test binding of the nanogels. The absorption and emission spectra of DiI and fluorescein suggest that these two dye molecules can be ideal FRET partners. Using FRET, it was found that the optimum ratios of NG1-CRRR and NG2-CRRR complexation with β-gal were 2:1 and 4:1, respectively. NG1-CRRR showed stable complexation at a lower concentration than NG2-CRRR, indicating stronger binding by the former nanogel, likely due to the greater amount of the peptide on the NG1-CRRR surface.

Figure 32:
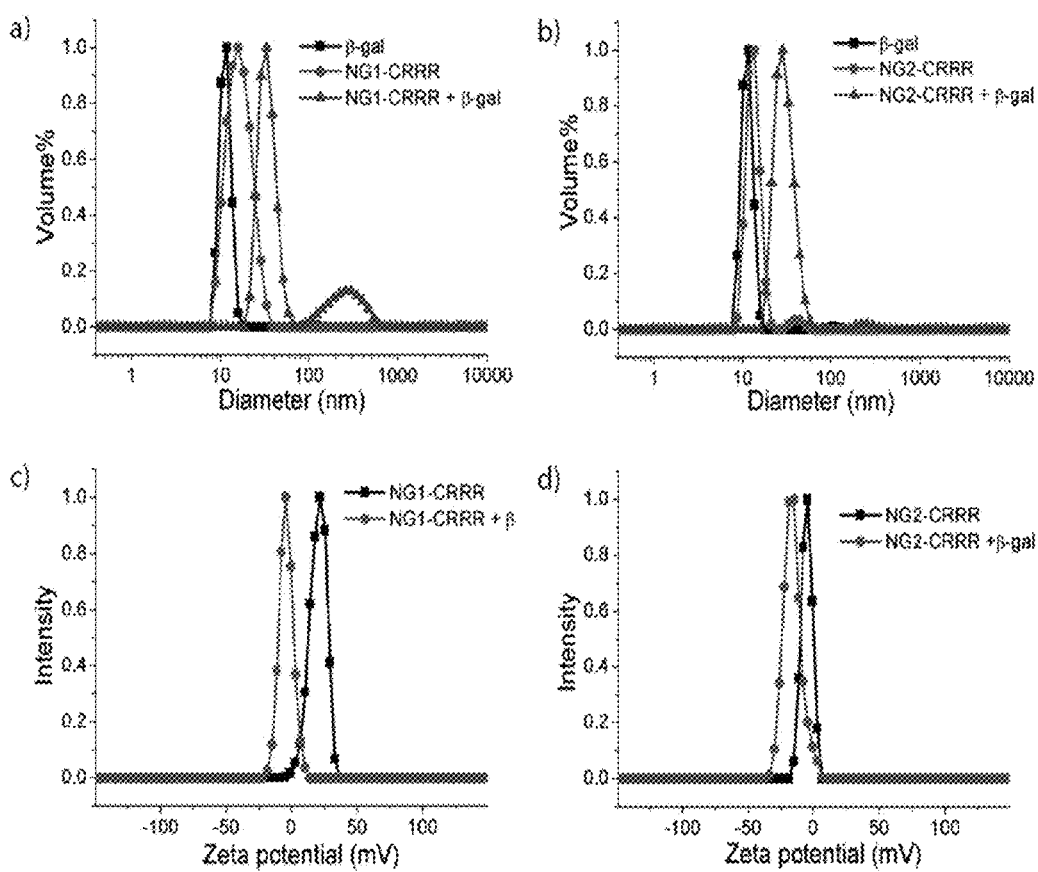
FIG. 32 shows exemplary DLS and ζ-potential graphs of: (a) β-gal, NG1-CRRR and β-gal:NG1-CRRR complex (1:2) and (b) β-gal, NG2-CRRR and β-gal:NG2-CRRR-β-gal complex (1:4).
Figure 38:
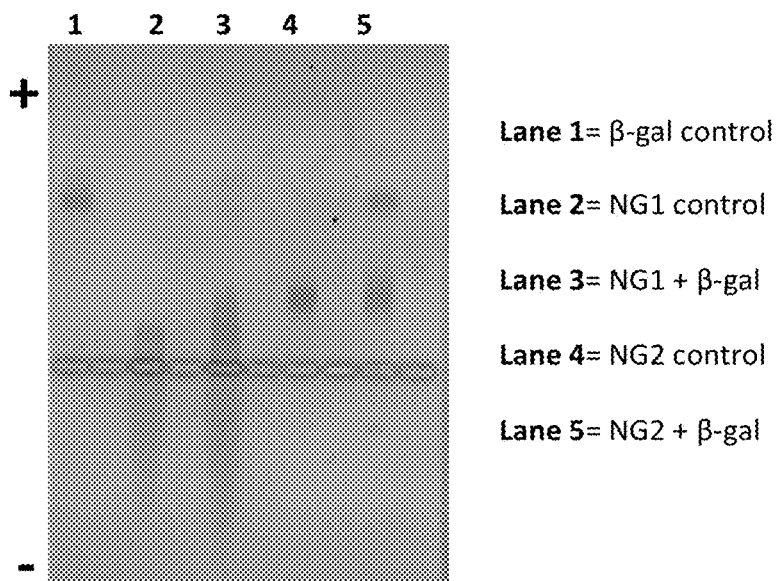
FIG. 38 shows exemplary Agarose Gel Electrophoresis for β-gal complexed to NG1-CRRR or NG2-CRRR.

Also evaluated were the size change and charge alteration of the nanogel surface due to the complexation event using DLS and zeta potential measurements respectively. The hydrodynamic diameters of individual NG1-CRRR, NG2-CRRR, and β-gal were found to be approximately 20 nm, 12 nm, and 10 nm, respectively (FIGS. 32*a* and 32*b*). Once the nanogels and the protein were mixed, the size shifts to about 40 nm for the complex of NG1-CRRR/Pβ-gal and 30 nm for NG2-CRRR/β-gal complex. Based on the sizes of the nanogels, β-gal, and the complexes, combined with their ratio, the average numbers of nanogel and β-gal per complex were estimated to be 7.6 and 3.8, respectively, for NG1-CRRR and 13.6 and 3.4 for NG2-CRRR. Zeta-potential studies showed that the apparent surface charge of the nanoparticles shifted towards the negative values, from +25 mV to −5 mV for NG1-CRRR and from 0 mV to −20 mV for NG2-CRRR after β-gal incorporation (FIGS. 32*c* and 32*d*). Nanogel-protein complexation was also reinforced by gel electrophoresis studies (FIG. 38). While, NG2-CRRR showed a large amount of unbound β-gal, NG1-CRRR showed a negligible amount of free β-gal. These results demonstrated that while both nanogels bind β-gal, the more positively charged NG1-CRRR exhibits stronger binding to the protein.

Figure 39:
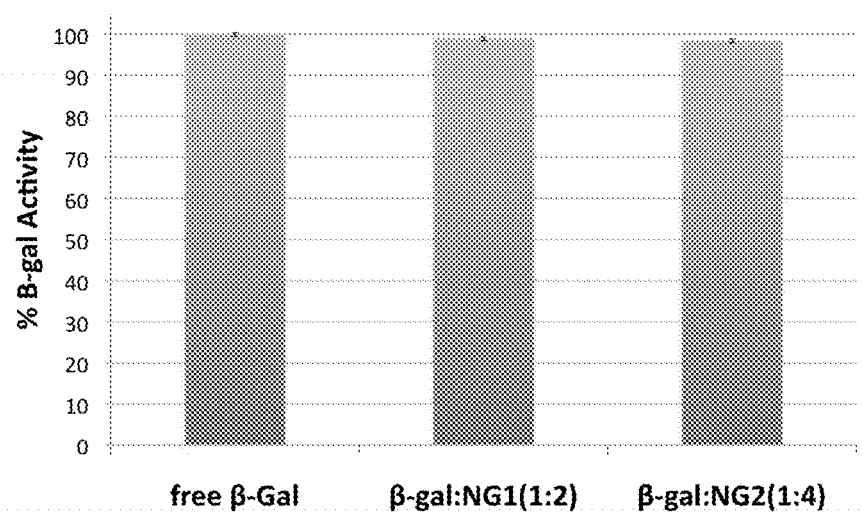
FIG. 39 shows exemplary activity assay of β-gal complexed to NG1-CRRR and NG2-CRRR.

The key motivation in developing this system is to achieve efficient intracellular delivery of the hydrophilic protein along with the lipophilic small molecules. It is important to maintain stability and activity of the delivered protein throughout the process. (Rothbard, et al. 2004 *J. Am. Chem. Soc.* 126, 9506-9507; Nakase, et al. 2008 *Adv. Drug Deliv. Rev.* 60, 598-607.) To this end, the activity of the protein was tested when complexed to the nanogel in solution before performing any intracellular release studies. An enzyme activity assay was done for β-gal complexed to NG1-CRRR and NG2-CRRR after 1 h incubation with the nanogels. It was observed that the protein retains its activity even when bound to the surface of the nanogels (FIG. 39). These results demonstrate the robustness of the complex in maintaining protein activity.

Intracellular delivery of DiI and β-gal was also tested. As the nanogels consist of biodegradable disulfide crosslinkers, the release of the complexed protein and encapsulated lipophilic molecule can be triggered upon exposure to glutathione (present at higher concentrations inside the cells (mM), compared to the extracellular concentration (M)). To compare the release profile of these dual delivery systems, NG1-CRRR and NG2-CRRR containing DiI in its interior and complexed with FITC labeled β-gal, were added to HeLa cells with serum and without serum. In the case of cell internalization of both encapsulated DiI and FITC labeled protein, a yellow color would be observed due to the co-localization and overlay of both red and green fluorophores for DiI and FITC, respectively. If there is no internalization of the nanogel, no color could be observed.

Figure 33:
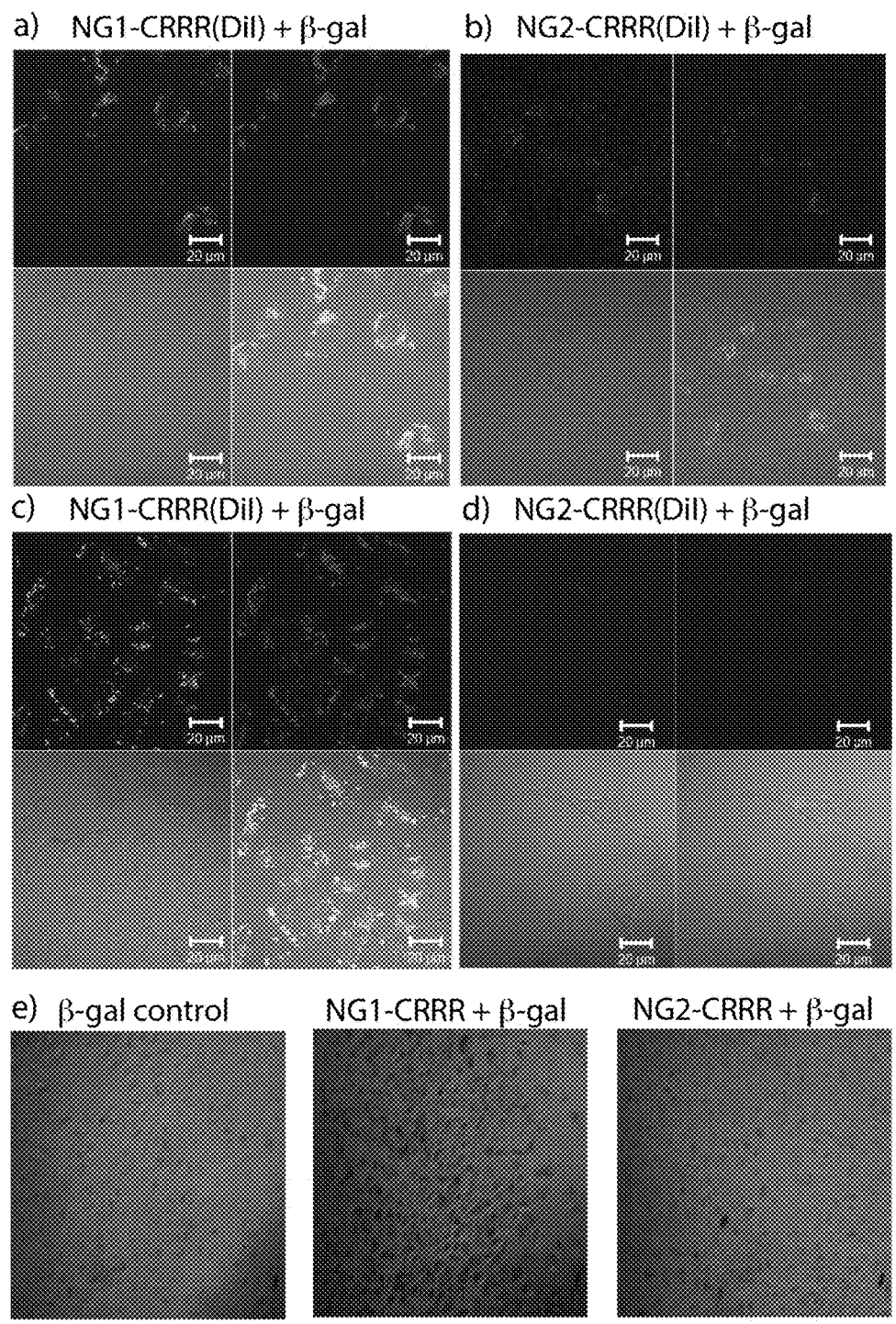
FIG. 33 shows exemplary protein and hydrophobic dye delivery using NG1-CRRR (a and c) and NG2-CRRR (b and d) without serum, and with serum, respectively. Within each image set, top left is the FITC channel which shows green color (β-gal) and top right is the DiI channel that shows red color (hydrophobic dye). Bottom left is the DIC image and bottom right is an overlap of all three. Yellow color is overlay of green and red. Scale bar is 20 μm. (e) X-gal activity assay of delivered β-gal into cells.
Figure 34:
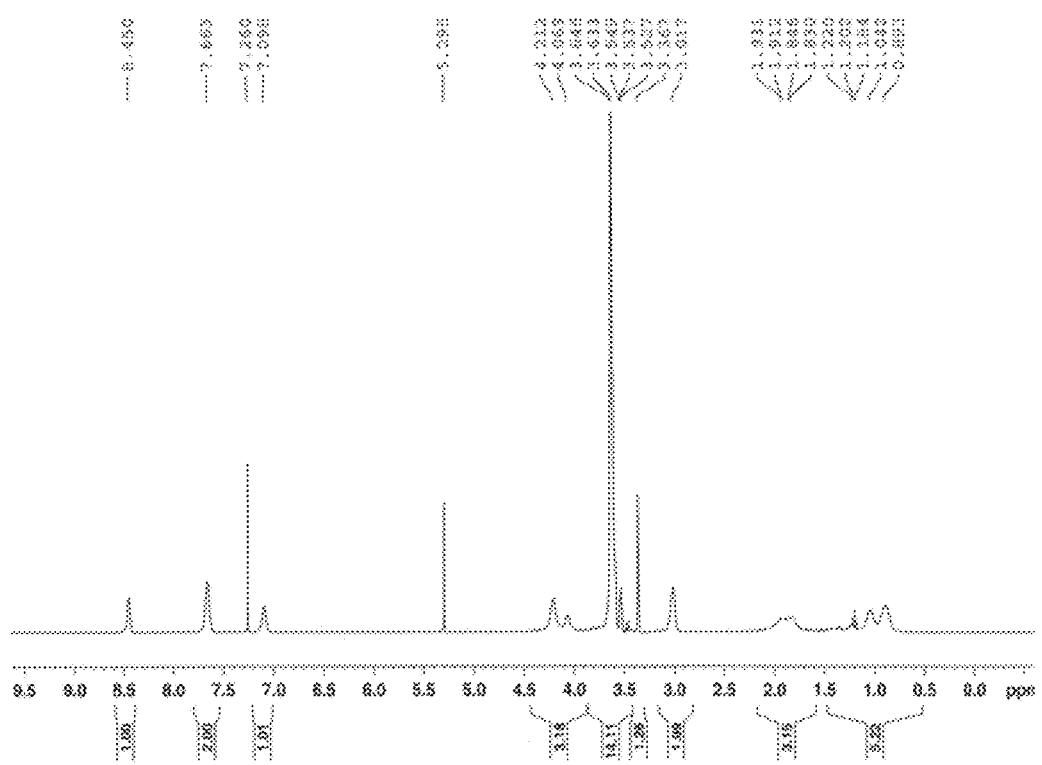
FIG. 34 shows exemplary NMR spectra of PEO:PD-SEMA polymer.
Figure 40:
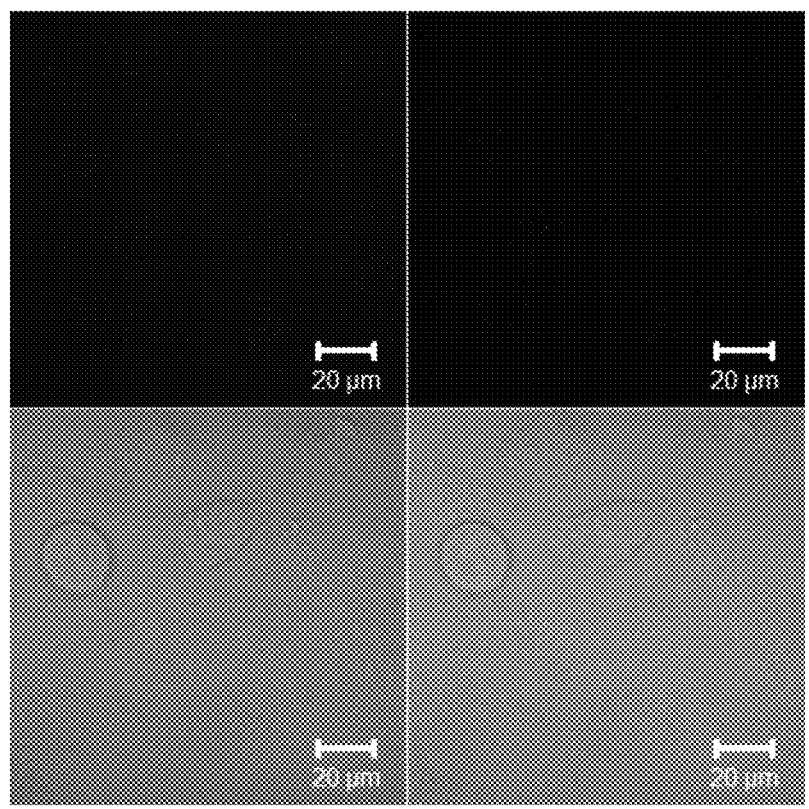
FIG. 40 shows exemplary intracellular delivery of native β-gal is not efficient without nanogel.

HeLa cells were treated with a 2:1 ratio of NG1-CRR/FITC-β-gal complexes and a 4:1 ratio of NG2-CRRR/FITC- β-gal complexes. Fluorescence distribution of DiI and FITC was observed over time by confocal fluorescence microscopy with simultaneous excitation of both dye molecules at 488 nm and 543 nm for FITC and DiI, respectively. As shown in FIGS. 33a and 33b, green and red emissions were observed when the cells were treated with the nanogel-protein complexes. On the other hand, cells incubated with FITC-β-gal alone displayed no fluorescence, indicating that the protein is not capable of cell penetration by itself (FIG. 40). The green fluorescence of the FITC (label for protein) and red fluorescence for DiI (encapsulated small molecule) appear uniformly distributed. While co-localization of DiI dye and β-gal in cells both with and without serum was observed for NG1-CRRR (FIGS. 33a and 33c), NG2-CRRR showed almost no efficiency of intracellular delivery of either cargos in the presence of serum (FIGS. 33b and 33d). The differences in delivery efficiency appear to be due to the stronger interaction of the protein with NG1-CRRR compared to NG2-CRRR, where serum proteins appear to compete for the interaction with the nanogels. The presence of red fluorescence with the yellow fluorescence in the case of the NG1-CRRR complex indicates that the nanogel and the protein are not only internalized, but also are also starting to spatially separate from each other, presumably due to GSH-based degradation of the disulfide bonds.

X-gal assays were performed on cells, which had been incubated with the nanogel β-gal complex, to probe the intracellular activity of the delivered β-gal (FIG. 33e). The observed blue color is due to the conversion of the 5-bromo-3-indoyl-β-D-galactopyranoside substrate to an intensely blue colored indigo derivative, by β-gal. From the optical microscope images, it can be observed that the cells treated with protein conjugated NG1-CRRR show enhanced blue coloration, due to greater β-gal internalization compared to NG2-CRRR and the control cells. These studies demonstrate that the delivered β-gal is active inside the cells. The observation that protein bound to NG1-CRRR has better intracellular activity than NG2-CRRR is consistent with the internalization studies using confocal microscopy. The results herein show that concurrent delivery of a protein and a hydrophobic dye simultaneously is indeed feasible with the approach outlined here.

Thus, the invention provides a nanogel that is capable of encapsulating lipophilic small molecules within its cross-linked interiors and binding proteins on its surface through electrostatic interactions. The nanogels can be functionalized with cell penetrating peptides efficiently. The nanogels bind oppositely charged proteins and that the charge density on the nanogel surface affects the efficiency of binding of the complementarily charged proteins. Complexation of the protein with the nanogel does not alter the activity of the protein. The complex exhibits efficient uptake by cells, where both the lipophilic small molecule and the protein are concurrently taken up by the cells. The enzyme retains its activity even upon cellular entry. The design strategy outlined here could have broad implications in a variety of areas including therapeutics, diagnostics, and a combination of the two by way of nanotheranostics.

Ligand-Decorated Nanogels and Cellular Targeting

Ligand-modified nanocarriers that are capable of targeting specific cells hold great promise in therapeutic applications, such as cancer chemotherapy. (Brannon-Peppas, et al. 2004 *Adv. Drug Delivery Rev.* 56, 1649-1659; Davis et al. 2008 *Nat. Rev. Drug Discovery* 7, 771-782; Kabanov, et al. 2009 *Angew. Chem. Int. Ed.* 48, 5418-5429; Duncan 2003 *Nat. Rev. Drug Discovery* 2, 347-360; Peer, et al. 2007 *Nat. Nanotechnol.* 2, 751-760.) When such nanoscale platforms also exhibit the propensity to act as carriers for non-covalently loaded cargo, these implications are even greater.

Targeting mechanisms for nanocarriers in cancer chemotherapy can be broadly classified into two categories, active and passive. Passive targeting is based on the propensity of nanoscopic objects, with 10-200 nm sizes, to selectively accumulate in solid tumor tissue due to the increased permeability of the tumor vasculature and ineffective lymphatic drainage, which is known as the enhanced permeation retention (EPR) effect. (Baban, et al. 1998 *Adv. Drug Delivery Rev.* 34, 109-119; Maeda, et al. 2000 *J. Controlled Release,* 65, 271-284.) Active targeting is achieved by associating the nanocarrier with ligands that exhibit high affinity for receptors that are overexpressed on the cancer cell surface. (Allen 2002 *J. Controlled Release* 2, 750-763; Byrne, et al. 2008 *Adv. Drug Delivery Rev.*, 60, 1615-1626.) While either of these targeting approaches can be effective, the most successful approach will likely be achieved by combining the key features of both strategies.

Targeting ligands, such as folic acid, have been studied as components of active targeting systems in the field of drug delivery. (Nasongkla, et al. 2004 *Angew. Chem. Int. Ed.* 43, 6323-6327; Lee, et al. 2008 *Angew. Chem. Int. Ed.,* 47, 2418-2421; Aluri, et al. 2009 *Adv. Drug Delivery Rev.,* 61, 940-952; Sudimack, et al. 2000 *Adv. Drug Delivery. Rev.* 41, 147-161.) In many cases, these ligands are attached to the hydrophilic ends of assembly-forming amphiphilic molecules (e.g. block copolymers). (Sutton, et al. 2007 *Pharm. Res.* 24, 1029-1046; Yoo, et al. 2004 *J. Controlled Release* 96, 273-283; Xu, et al. 2007 *Angew. Chem. Int. Ed.* 46, 4999-5002.) However, the installation of such ligands onto these molecules requires complicated synthetic steps, limiting the versatility of ligand functionalization to tailor carriers for targeting specific cell types. Additionally, modification of the self-assembling molecules by this method could alter their hydrophilic-lipophilic balance (HLB) and introduce undesirable variations in assembly behavior, thus requiring optimization on a case-by-case basis.

A class of drug delivery vehicle, which affords surface modification of chemically-crosslinked nanocarriers with reactive functional groups in a post-assembly step, can address these complications. In such a system, the nanocarrier morphology is maintained during modification, providing versatility in surface functionalization without compromising the structural integrity of assembly properties of the nanoscopic scaffold. The nanocarrier hosts stably encapsulate guest/drug molecules until they reach the site of the targeted cells.

Figure 41:
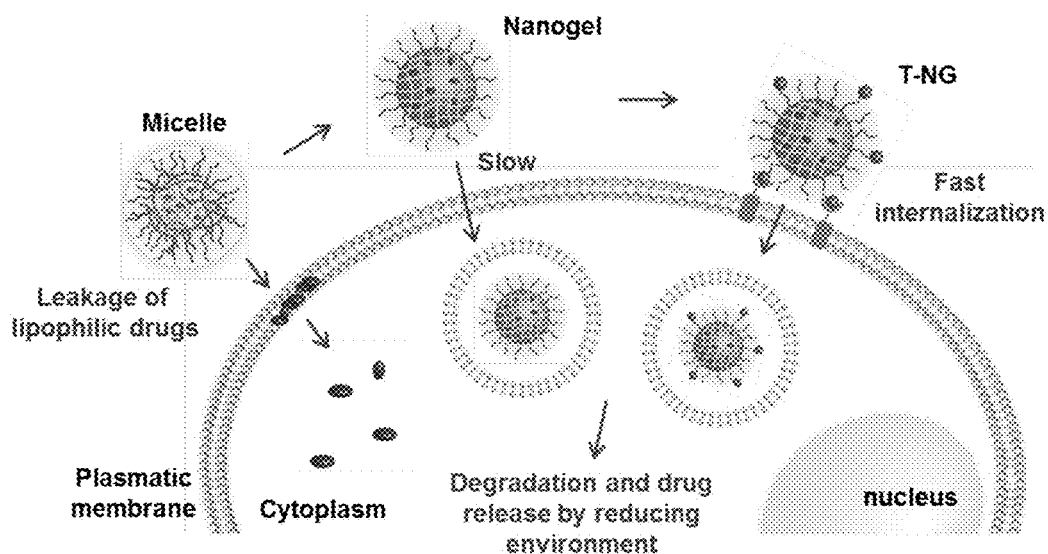
FIG. 41 shows exemplary nanogels are non-leaky, but exhibit slow celluar internalization; polymeric micelles exhibit rapid internalizations of lipophilic drug molecules due to leakage of free drug from the assembly interior; T-NGs exhibit high encapsulation stability and fast cellular internalization, which has a great potential for passive and active targeting drug delivery.

Herein disclosed is a fast, one-pot synthesis of ligand-decorated nanogels (FIG. 41). The resulting delivery vehicles exhibit high encapsulation stability to exploit passive targeting mechanisms and can be easily modified at their surfaces with various ligands for the active targeting of cell surface receptors.

The targeted nanogels (T-NGs) were prepared within 2 h by a one-pot synthesis and exhibited very narrow size distributions. These nanogels can be simply prepared with cysteine-modified ligands including folic acid, cyclic arginine-glycine-aspartic acid (RGD) peptide, and cell-penetrating peptide. As demonstrated herein, the T-NGs hold their payloads, undergo facilitated cell internalization by receptor-mediated uptake, and release their drug content inside cells due to cleavage of crosslinked disulfide bonds by the reducing intracellular environment. (Vader, et al. 2011 *Pharm. Res.* 28, 1013-1022; Lin, et al. 2009 *J. Expert Opin.*

Drug Deliv. 6, 421-439; Bronich, et al. 2002 *J. Am. Chem. Soc.* 124, 118720-11873; Kim, et al. 2010 *Biomacromolecules* 11, 919-926.)

Figure 42:
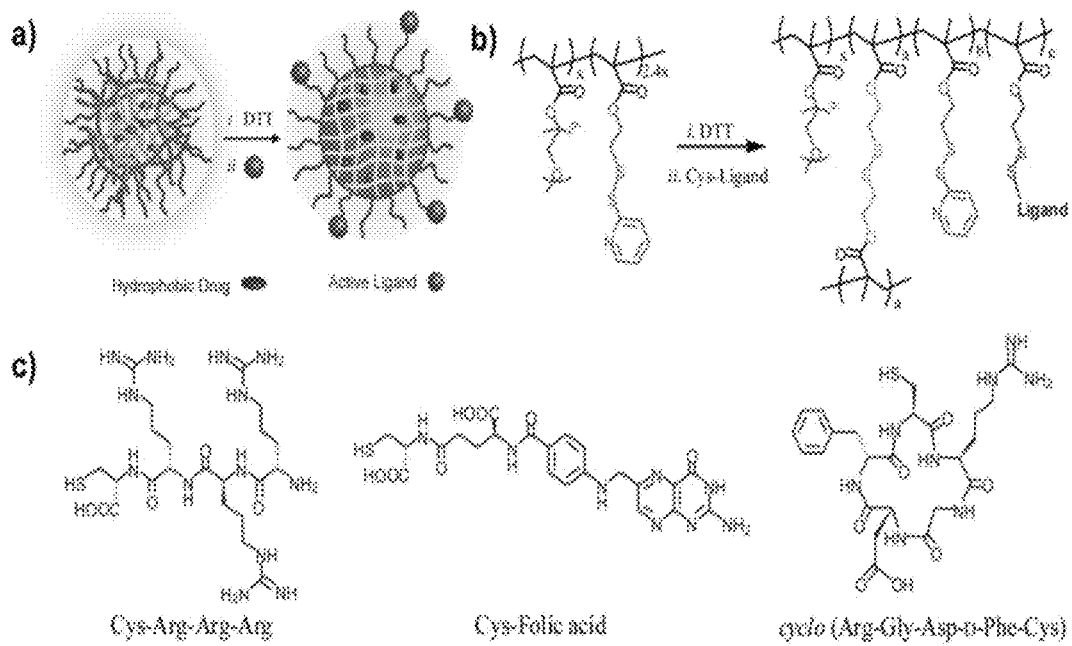
FIG. 42 shows exemplary (a) Schematic representation of the one-pot synthesis of T-NGs, (b) chemical structure of polymer and T-NGs, and (c) cysteine-containing targeting ligands.
Figure 43:
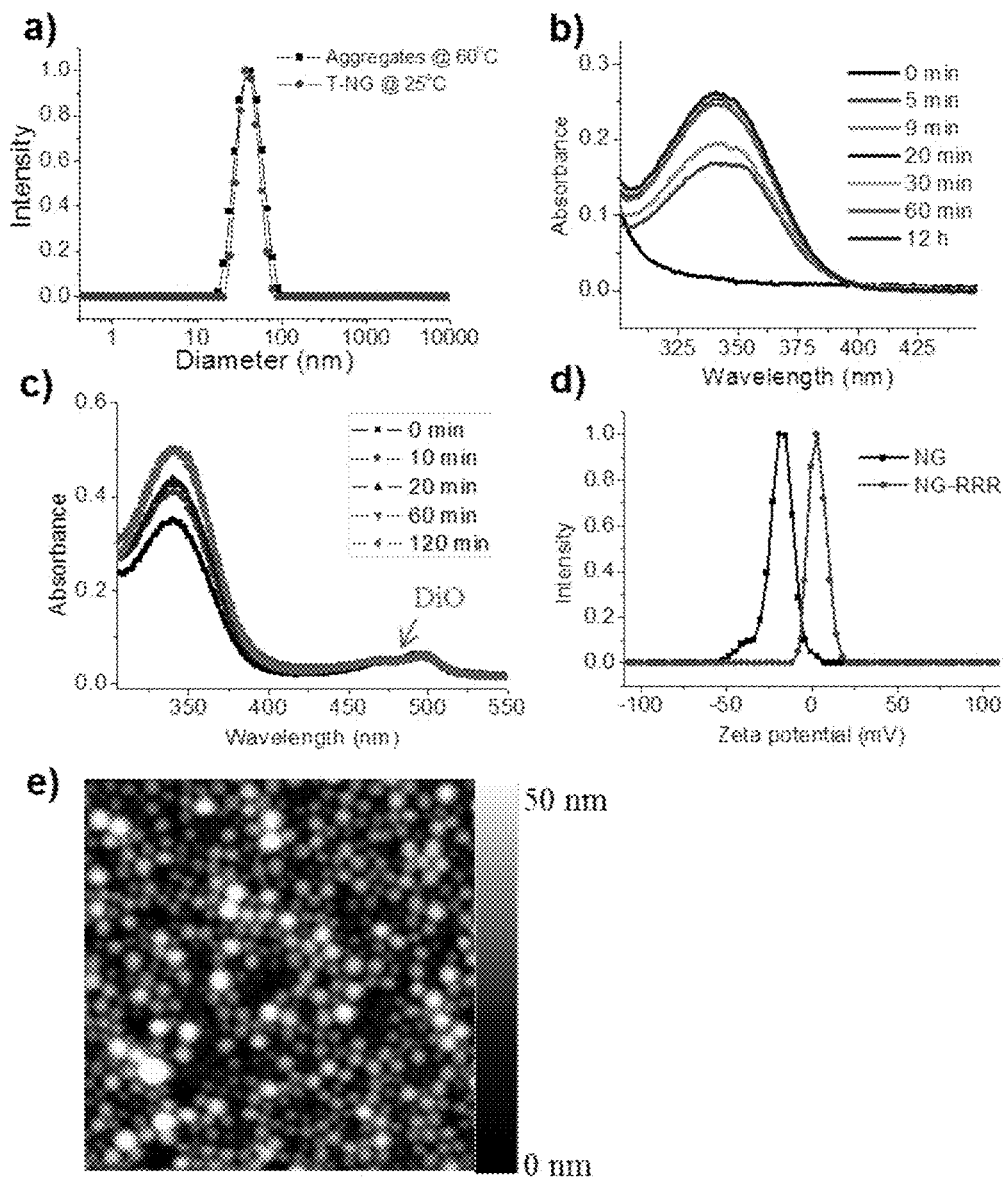
FIG. 43 shows exemplary (a) Dynamic light scattering of polymer aggregates (10 mg/mL) at 60° C. and T-NG (10 mg/mL) at room temperature. UV absorbance of pyridothione (b) during nanogel synthesis (0.04 mg/mL) and (c) ligand modification with CRRR (0.05 mg/mL). (d) Zeta potential of nanogel (NG) (1 mg/mL) and NG-RRR (1 mg/mL). (e) AFM image of T-NG (2 μm×2 μm).

Preparation of T-NG. T-NGs were prepared through the lock-in strategy using a random copolymer that contains oligoethylene glycol (OEG) units (29%) and PDS moieties (71%) as side chain functionalities (FIG. 42). At elevated temperatures, the polymer formed larger aggregates (42 nm in diameter) than at room temperature (24 nm in diameter), likely due to intermolecular associations between the polymer chains caused by LCST behavior of the OEG units (FIG. 43*a*). Preparation at high temperatures facilitates the crosslinking reaction and that subsequent addition of cysteine-containing ligands would enable a fast, one-pot T-NG synthesis. The crosslinking and surface modification reactions were observed to finish within a very short time period. FIG. 43*b*, which traces production of the pyridothione byproduct of disulfide bond formation during nanogel synthesis, plateaus within 20 min. A deficient amount of DTT (20 mol % against the precursor PDS groups) cleaved a corresponding amount of polymer PDS functionalities, generating free thiols that can then react with remaining PDS functionalities in the polymer chain (both intra- and inter-chain) to provide the crosslinked polymer nanogel. Based on pyridothione release, the actual crosslinking density was found to be 13-14% (39 mol % of PDS is consumed), which is very close to the theoretically calculated crosslinking density of 14%.

The cysteine-containing ligand, cysteine-triarginine (CRRR) peptide, was added to this reaction mixture to modify the surface and attachment of the ligand was evaluated by further increase in pyridothione absorption. The peak became saturated within 60 min and it was calculated that 17 mol % of total PDS is reacted with CRRR (FIG. 43*c*). It was estimated that there were about seven thousand ligands per T-NG. One can question whether such a thiol-containing ligand will cleave the crosslinking disulfide bonds, resulting in size change, nanogel disassembly, and leakage of hydrophobic guest molecules during ligand modification. T-NG retained their size from the polymer aggregate at high temperature (FIG. 43*a*), and the absorption intensity of hydrophobic dye, DiO, which is encapsulated prior to crosslinking and surface modification was not changed, indicating that the nanogels were sufficiently stable to retain their guest molecules during this functionalization period (FIG. 43*c*). Surface modification was confirmed of the nanogels by monitoring the change of surface charge. As shown in FIG. 43*d*, the nanogels modified with CRRR (NG-RRR) showed positive zeta potentials (+4 mV), while the nanogels showed negative zeta potentials (−20 mV) before surface modification.

The resulting T-NGs showed narrow size distribution. Atomic force microscope (AFM) images reveal well-defined spherical structures with very uniform size. The size is around 50 nm in diameter, which may be ideal for the passive targeting applications. (Chithrani, et al. 2007 *Nano Lett.* 7, 1542-1550.) Additional ligands, including cysteine-modified folic acid and cysteine-containing cyclic arginine-glycine-aspartic acid (RGD) peptides, were also linked by this synthetic method to make T-NGs, NG-FA and NG-RGD, respectively.

Several features are noteworthy in the modified synthetic methods: (i) the current method allows for obtaining these nanogels in very short amount of time; (ii) it also allows for decorating the nanogels with targeting ligands in a single pot and the precursor polymer is crosslinked into a nanogel and decorated with targeting ligands in less than two hours; (iii) the resultant nanogels exhibit narrow polydispersity; and (iv) these nanogels also exhibit enhanced encapsulation stability. (Ryu, et al. 2010 *J. Am. Chem. Soc.* 132, 8246-8247; Ryu, et al. 2010 *J. Am. Chem. Soc.* 132, 17227-17235.)

Figure 44:
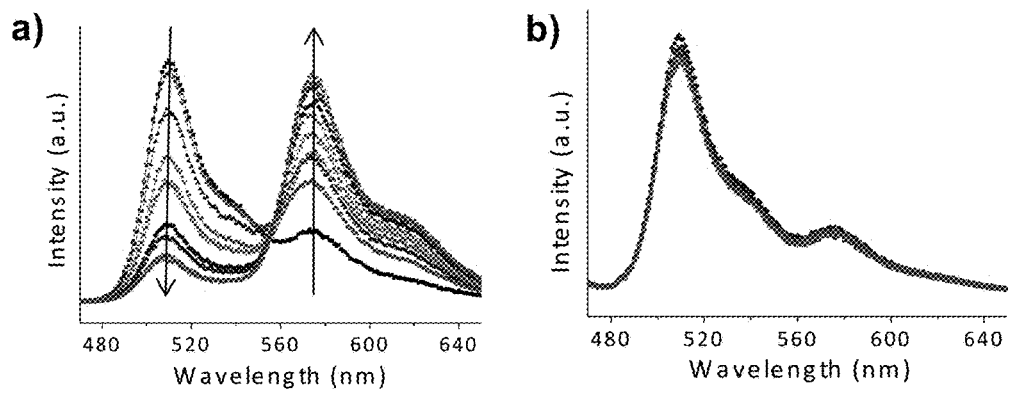
FIG. 44 shows exemplary fluorescence emission spectra of mixed polymer aggregates (a) and NG (b) separately encapsulated DiI/DiO.

Encapsulation stability. The noncovalent encapsulation stabilities of the T-NGs were tested from the dynamics of guest interchange in the nanocarriers using a FRET experiment. (Jiwpanich, et al. 2010 *J. Am. Chem. Soc.* 132, 10683-10685.) Two lipophilic FRET pair dye molecules, DiO and DiI, were independently encapsulated in the nanogels. While significant and rapid FRET evolution was observed in the case of the polymer aggregates, the crosslinked nanogels showed no significant peak shift, indicating their high encapsulation stabilities (FIG. 44).

Figure 45:
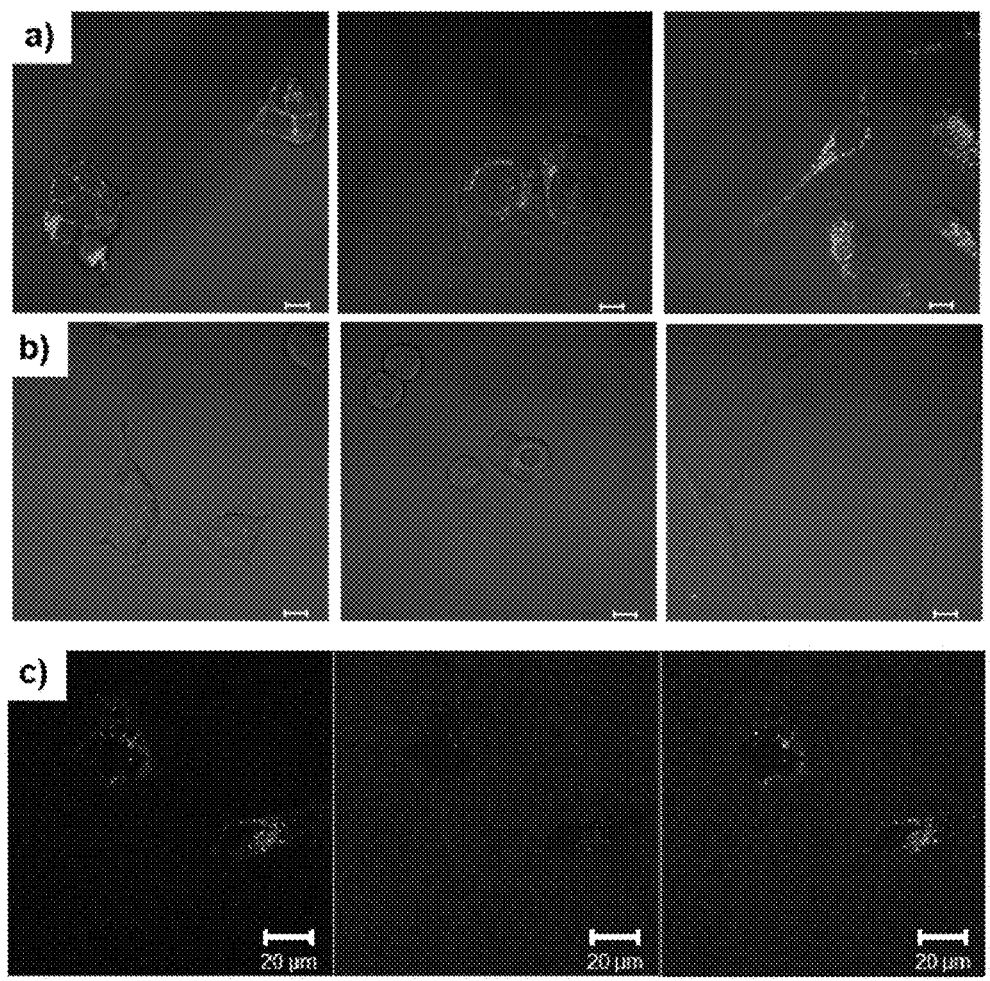
FIG. 45 shows exemplary cell internalization of DiO which is encapsulated in polymer aggregates (a) and NG (b) at different cell lines (left: 293T, middle: (MCF7, right: HeLa, scale bar=10 μm). (c) In situ cell internalization of hydrophobic dye by FRET (left: DiO channel, middle: DiI channel, right: overlap of both channel). No FRET inside cell indicates that the dyes only were transferred into the cells without polymer aggregates. Each cell line was cultured in DMEM/F12 with 10% FBS supplement.

Cellular internalization of polymer micelle and NG. The differences in cellular internalization of the polymer aggregates, nanogels and T-NGs loaded with hydrophobic dye molecules were tested. The polymer aggregates and nanogels, containing DiO as a hydrophobic dye, were added into three different cell cultures (293T, MCF-7, and HeLa cell lines). The uptake was monitored by tracing the dye's fluorescence using confocal microscopy (FIG. 45*a-b*). In the case of the polymer aggregates, intense green emission inside the cells was observed within 6 h across all cell lines. In contrast, the nanogels showed no emission, indicating that the nanogels were not internalized in this short time period. Also performed were in situ FRET experiments with HeLa cells using the amphiphilic aggregates in which the FRET pair DiO (green emission) and DiI (red emission) was co-encapsulated. In this case, if the polymeric aggregates were internalized through the membrane, then FRET (red emission, 585-615 nm spectral filter) would be continually observed in the cytosolic interior within a short time period. After 3 h incubation, it was observed that green (no FRET, 505-520 nm spectral filter) fluorescence is dominant inside the cell by confocal microscopy (ex=488 nm), indicating that the two dyes are not close together within the assembly core, but that they have released from the micelles (FIG. 45*c*). This demonstrates that liphophilic guests loaded inside micellar aggregates can be transferred into any cells, resulting in non-specific delivery. High encapsulation stability is essential to prevent premature, non-triggered release and achieve selective delivery of the drug molecules to target cells.

Selective cellular internalization of T-NG. To promote selective and rapid internalization into target cells, the surfaces of the slow-internalizing nanogels were decorated with specific ligands. To probe the versatility of ligand functionalization, three different ligands were used: CRRR, CRGD, and cysteine modified-folic acid. RGD is the ligand of the integrin $\alpha_v\beta_3$ that is involved in tumor angiogenesis and metastasis and is overexpressed in many solid tumor types such as breast, prostate, and ovarian cancers. (Haubner, et al. 1996 *J. Am. Chem. Soc.* 118, 7461-7472.) Folic acid is a widely used ligand in targeted delivery research, because folate receptors (FR) are notably overexpressed on the surfaces of many cancer cells such as ovarian, lung, and uterine tumors. (Lu, et al. 2002 *Adv. Drug Delivery Rev.* 54, 675-693.) RRR can be considered as a positive control, as it is a model cell penetrating peptide and is thus rapidly and non-selectively taken up by most cell types. These arginine-rich peptides are considered to be mimics of the well-known TAT peptides, which are known for translocating molecules and nanoscale objects across the cellular membrane. (Rothbard, et al. 2005 *Adv. Drug Delivery Rev.* 57, 495-504.)

Cellular uptake of the nanogels modified with CRRR, CRGD, and cysteine-modified-folic acid (referred to as NG-RRR, NG-RGD, and NG-FA, respectively) were tested in varied cell lines: 293T kidney cells are normal cells used as a control, MCF7 is a slightly FR-positive tumor cell line and is negative to RGD, while SKOV3 and HeLa cells are positive to both ligands.

Figure 46:
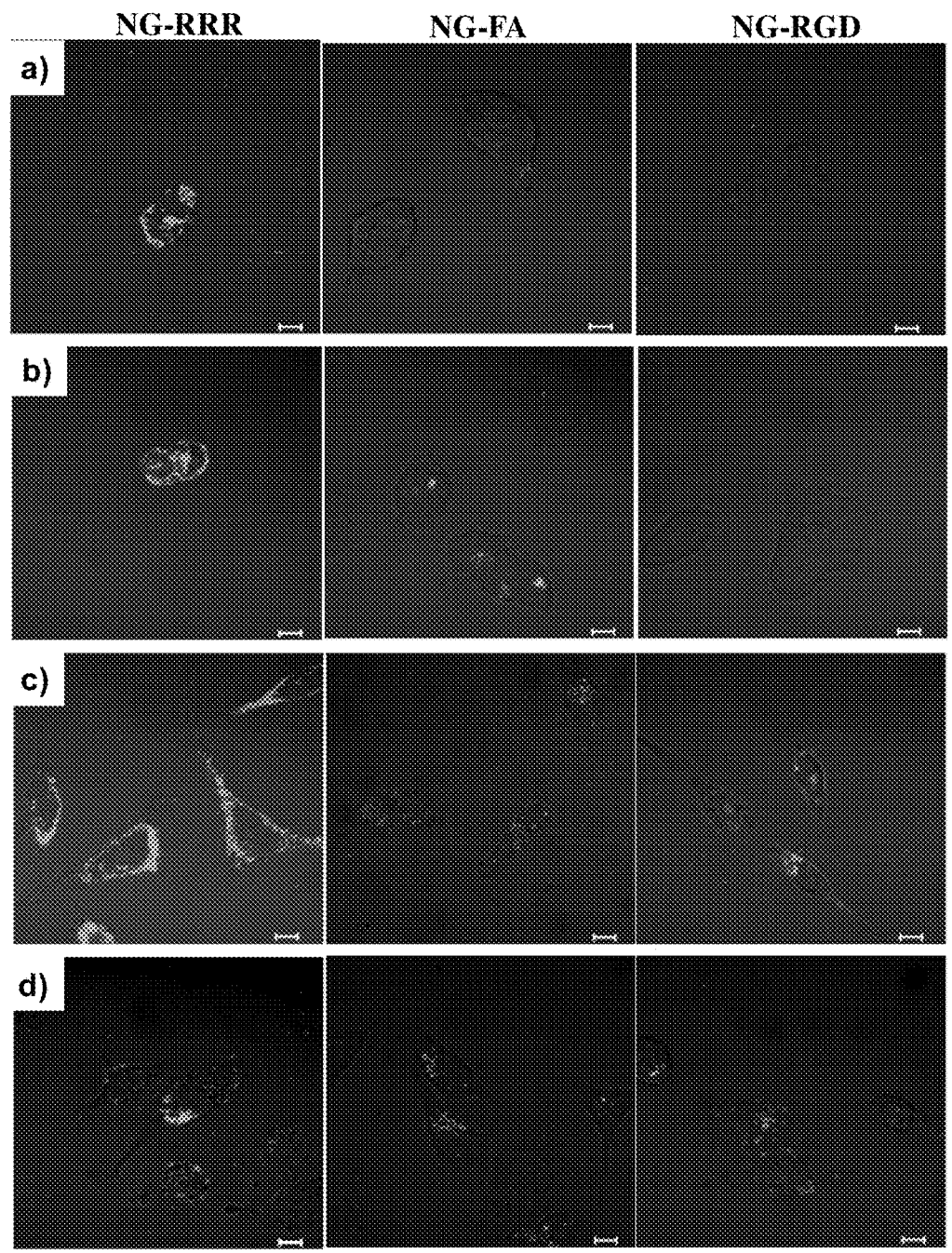
FIG. 46 shows exemplary confocal microscopy images of T-NGs containing DiO at different cell lines, (a) 293T, (b) MCF7, (c) HeLa, and (d) SKOV3. (left: NG-RRR, middle: NG-FA, right: NG-RGD, scale bar=10 μm). Each cell line was cultured in DMEM/F12 with 10% FBS supplement.

To test selective cellular internalization by receptor-mediated endocytosis, ligand-decorated nanogels encapsulating DiO as a model hydrophobic drug molecule were incubated with various cell lines for 6 h and then qualitatively examined through confocal microscopy (FIG. 46). In the case of NG-RRR, high green emission was observed inside cells in all cell lines within just 2 h, indicating that the nanogels were internalized rapidly because of the highly positive cell penetrating peptide, RRR. In the case of NG-FA, the nanogels exhibited fast cellular uptake with SKOV3, HeLa and MCF7 cells in which FR is overexpressed. However, the FR-negative 293T cells showed negligible cellular uptake of the folic acid decorated nanogel. Similarly, with NG-RGD, HeLa and SKOV3 exhibited high internalization, as these cells are considered to overexpress integrin $\alpha_v\beta_3$. However, MCF7 and 293T cells, which are negative to integrin, showed little internalization. These results demonstrate the selective internalization of the various T-NGs through receptor mediated endocytotic pathways.

Figure 47:
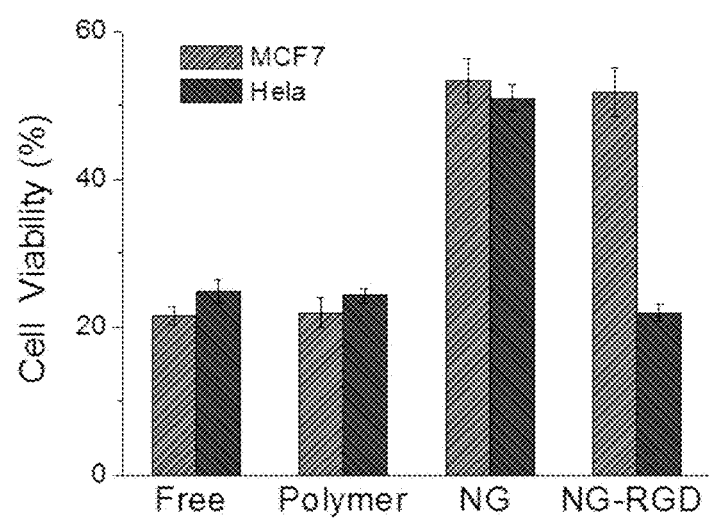
FIG. 47 shows exemplary in vitro toxicity of PTX-loaded NG-RGD with MCF7 and HeLa cells after 72 h incubation. The loading amount of PTX is 5 wt % for polymer and NG. 10 μM of PTX is used for all experiments.
Figure 48:
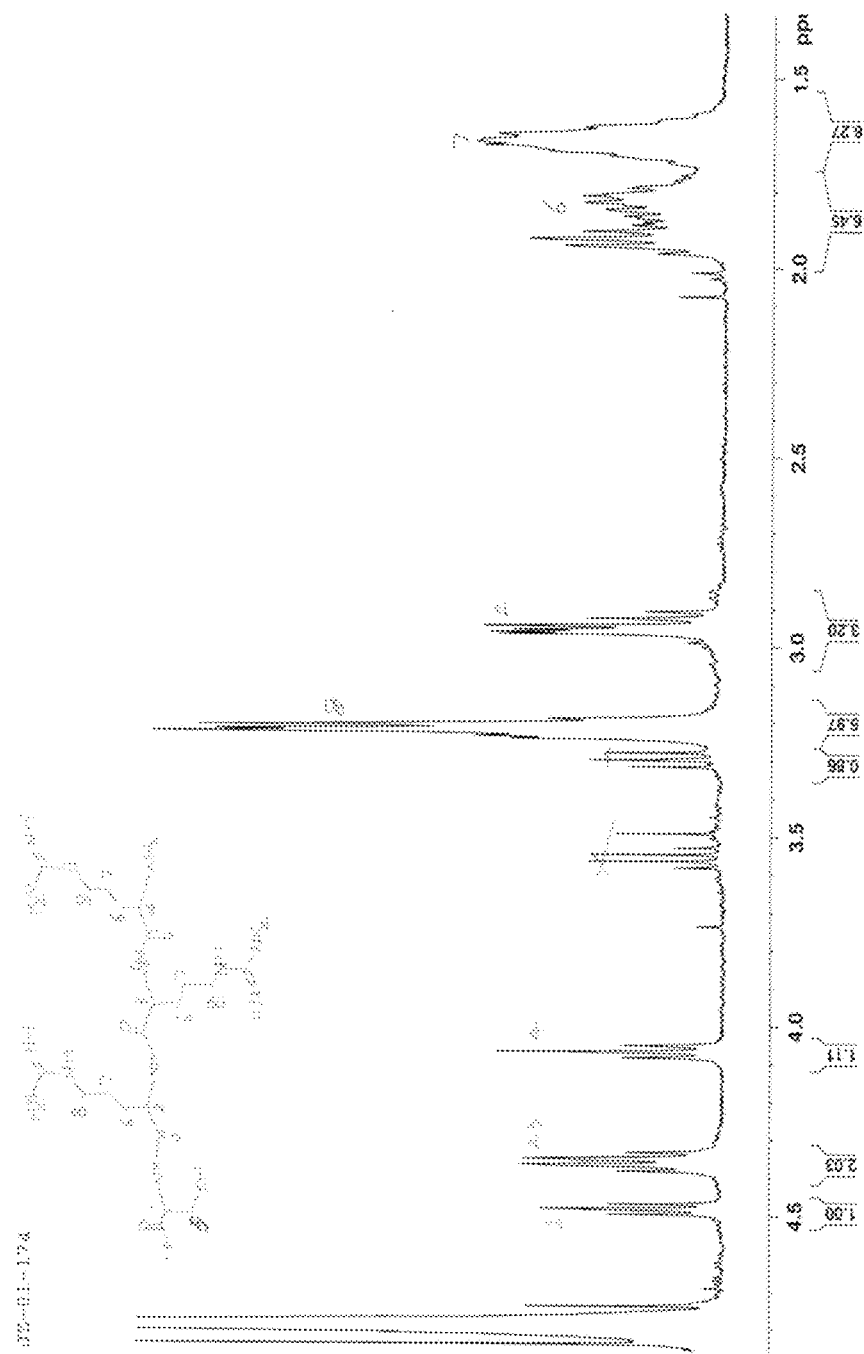
FIG. 48 shows exemplary $^1$H-NMR and MS of cell penetrating peptide CRRR.
Figure 49:
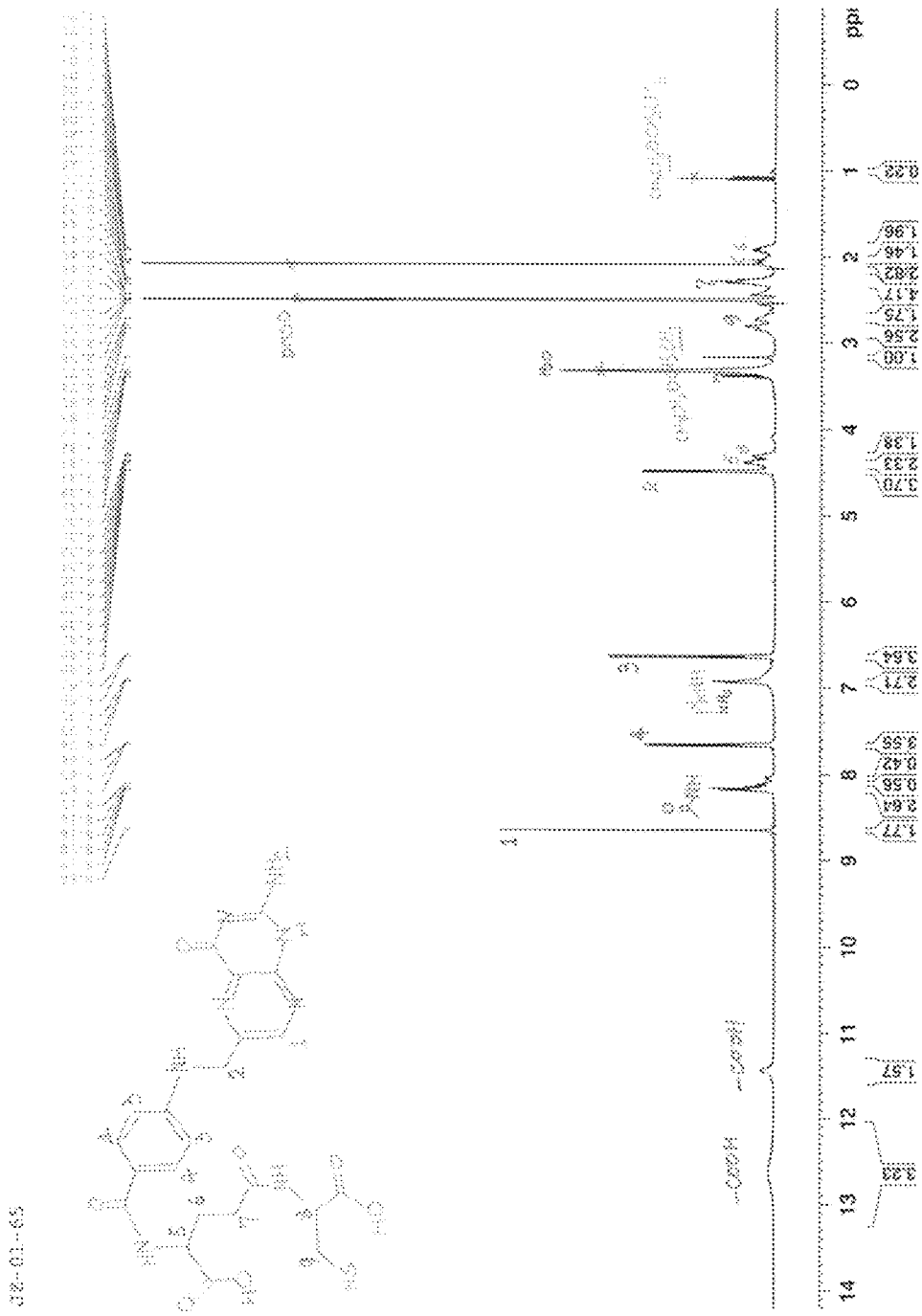
FIG. 49 shows exemplary $^1$H-NMR and MS of cysteine-folic acid.
Figure 50:
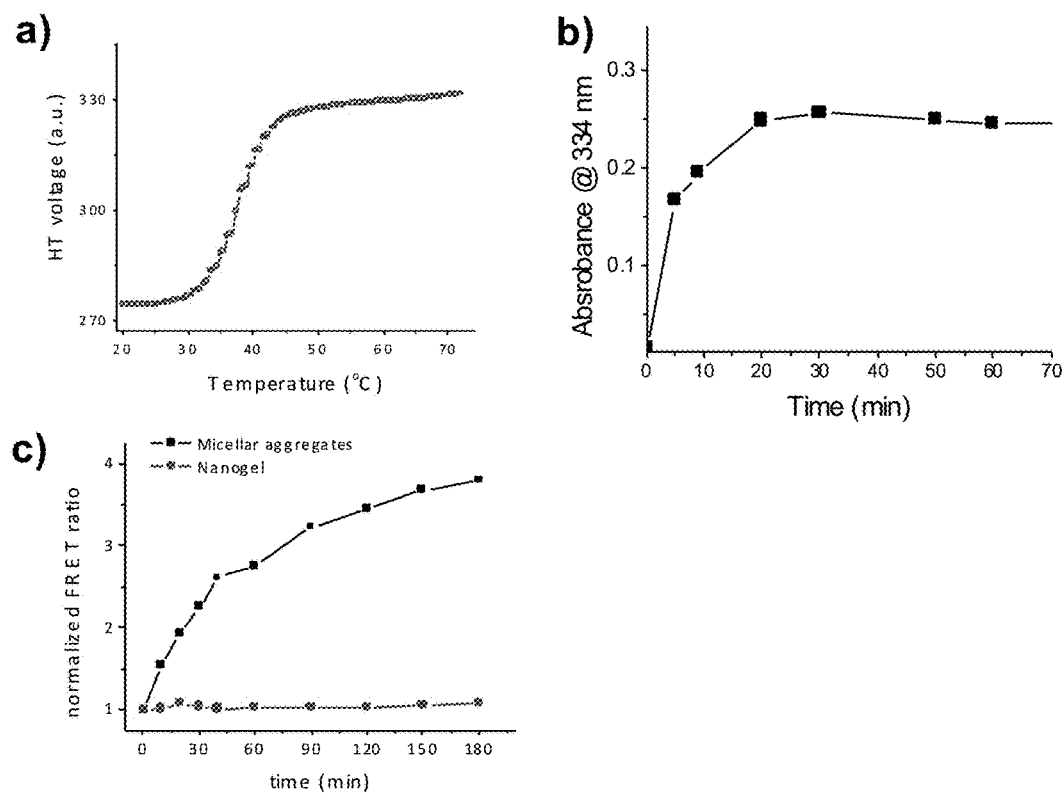
FIG. 50 shows exemplary (a) Turbidity experiment shows the change in high tension voltage with temperature of the polymer due to the LCST behavior of oligoethylene glycol (OEG) in the polymer side chain. b) Plot of the absorption maximum of pyridothione which is a byproduct of the disulfide bond formation during nanogel synthesis. The production of pyridinethione plateaus within 20 min, indicating that disulfide crosslinking is finished within 20 min. c) Plot of fluorescence of resonance energy transfer (FRET) ratio vs. time. The nanogels showed no significant FRET ratio change, indicating the high encapsulation stability, while polymer aggregates themselves showed very fast FRET evolution, suggesting the leakage property of these aggregates.
Figure 51:
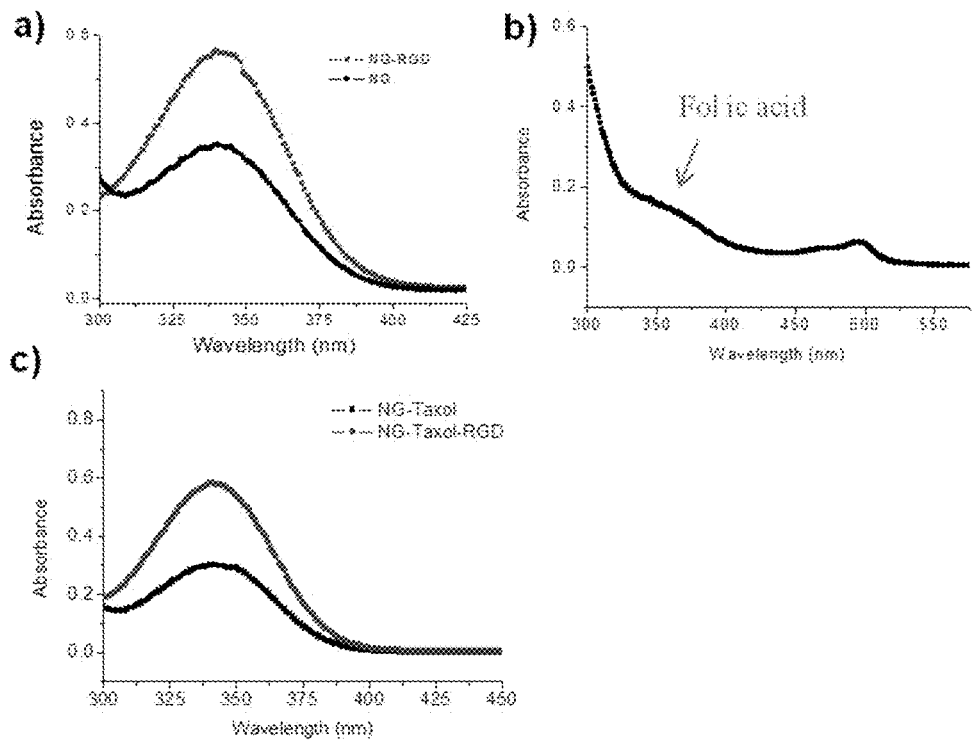
FIG. 51 shows exemplary UV-vis absorbance of T-NGs. (a) UV-vis absorbance of pyridothione after nanogel synthesis (black) and ligand modification (red) with CRGD (0.05 mg/mL). (b) UV-vis absorbance of folic-acid decorated (0.05 mg/mL). The measurement was performed after purification by dialysis because the absorbance of folic acid and pyridothione are overlapped. (c) UV-vis absorbance of pyridothione of taxol containing nanogel (black) and ligand modification (red) with CRGD (0.05 mg/mL).
Figure 52:
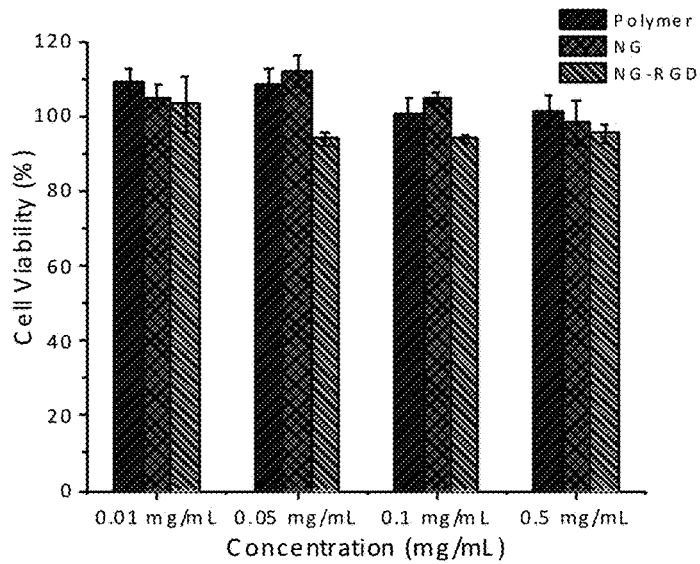
FIG. 52 shows exemplary (a) In vitro toxicity of polymer, empty nanogels, and RGD-coated nanogels with 293T cells after 24 h incubation. Cell viability was measured using the Alamar Blue assay. The polymer, empty nanogels, and RGD-coated nanogels exhibit high cell viability and no concentration dependent toxicity up to the concentration of 0.5 mg/mL, indicating that the all material is non-toxic.

Selective delivery of chemotherapeutic drug. To test whether the observed target selectivity would translate into differential cell kill efficiency, the ligand-coated nanogels encapsulating a chemotherapeutic drug molecule, paclitaxel (PTX) were prepared. The PTX-loaded polymeric aggregates (polymer-PTX), NG (NG-PTX) and NG-RGD (NG-RGD-PTX) were added to MCF7 cells and HeLa cells and the extent of cell death was investigated after 72 h. As shown in FIG. 47, free PTX and polymer-PTX were highly toxic in both cell lines. This supports the hypothesis that the polymeric micellar aggregates have a leaky nature, which leads to free drug being translocated through the cellular membrane. In contrast, NG-PTX showed less toxicity, compared to both free-PTX and polymer-PTX. This is consistent with the observed slow internalization of nanogels, which should result in a reduced amount of chemotherapeutic inside the cells. Remarkably, NG-RGD-PTX showed different cell killing efficiency in two different cell lines. While MCF7 showed similar toxicity with NG-PTX, HeLa showed high toxicity that is similar to free-PTX, indicative of the selective delivery of PTX to this cell line. Together with the cellular internalization experiments, this result demonstrates that NG-RGD is highly internalized into the integrin receptor overexpressing HeLa cells, thus enhancing the efficiency of chemotherapeutics by promoting selective drug delivery.

Thus, the invention provides a facile synthetic method for the preparation of nanogels: (i) these nanogels can be prepared in under two hours from their polymeric precursor; the reaction time includes the ligand decoration step; (ii) these nanogels exhibit high encapsulation stability of lipophilic guest molecules; (iii) the facile ligand functionalization possibility can be utilized to decorate these nanogels with cell targeting ligands; (iv) while the unfunctionalized nanogels are taken up very poorly by various cells, the ligand-decorated nanogels exhibit facilitated receptor-dependent cellular uptake, as demonstrated by selective uptake of RGD- and folic acid-decorated nanogels by cells overexpressing integrin and folate receptors; (v) functionalization of the nanogels with cell penetrating peptides caused rapid non-specific uptake by the cells, independent of the receptor; (vi) the selective internalization capability can be translated to delivering a chemotherapeutic drug molecule specifically to a specific receptor-rich cell. Overall, the reported versatile one-pot synthetic method for synthesizing the ligand-decorated nanogels, combined with the intrinsic encapsulation stability and targeting capabilities of the formed T-NGs, should open up new avenues in targeted drug delivery for crosslinked polymer nanogels.

EXPERIMENTAL

General. 2,2'-Dithiodipyridine, 2-mercaptoethanol, polyethylene glycol monomethyl ether methacrylate (MW 450), D,L-dithiothreitol (DTT), 1,1'-dioctadecyl-3,3,3',3'-tetramethylindocarbocyanine perchlorate (DiI) and 3,3'-dioctadecyloxacarbocyanine perchlorate (DiO), Nile red, Tat-SH, and other conventional reagents were obtained from commercial sources and were used as received unless otherwise mentioned. Polymer was synthesized using RAFT polymerization and then purified by precipitation. S-dodecyl-S'-2-(2,2-dimethylacetic acid) trithiocarbonate, (Lai, et al. 2002 *Macromolecules* 35, 6754-6756.) 2-Cyano-2-propyl benzodithioate and pyridyl disulfide ethyl methacrylate (PDSEMA) was prepared using a previously reported procedure. (Brown, et al. 2007 *Chem. Commun.* 2145-2147; Ghosh, et al. 2006 Macromolecules 39, 5595-5597.) $^1$H-NMR spectra were recorded on a 400 MHz Bruker NMR spectrometer using the residual proton resonance of the solvent as the internal standard. Molecular weights of the polymers were estimated by gel permeation chromatography (GPC) using PMMA standard with a refractive index detector. DLS measurements were performed using a Malvern Nanozetasizer. The fluorescence spectra were obtained from a JASCO FP-6500 spectrofluorimeter. Transmission electron microscopy (TEM) images were taken from JEOL 100 CX at 100 KV.

Random copolymer 1. A mixture of 2-Cyano-2-propyl benzodithioate (3 mg, 0.0135 mmol), PDSEMA (52 mg, 0.203 mmol), polyethylene glycol monomethyl ether methacrylate (96.7 mg, 0.203 mmol) and AIBN (0.11 mg, 0.6 µmol) was dissolved in THF (300 µL) and N$_2$ gas was purged 30 min to the solution. To this reaction mixture, 500 µL THF was added and sealed and then put into a pre-heated oil bath at 62° C. for 40 h. To remove unreactive monomers, the resultant mixture was precipitated in cold ethyl ether (20 mL) to yield the random copolymer as a waxy liquid. GPC (THF) $M_n$: 6.9 K. PDI: 1.2. $^1$H NMR (400 MHz, CDCl$_3$) δ: 8.45, 7.66, 7.09, 4.20-4.06, 3.90-3.36, 3.01, 2.15-1.62, 1.43-0.86. The molar ratio between two blocks was determined by integrating the methoxy proton in the polyethylene glycol unit and the aromatic proton in the pyridine and found to be 4.7:5.3 (PEO:PDSEMA).

Random copolymer 2. A mixture of 2-Cyano-2-propyl benzodithioate (3 mg, 0.0135 mmol), PDSEMA (104 mg, 0.407 mmol), polyethylene glycol monomethyl ether methacrylate (193.4 mg, 0.407 mmol) and AIBN (0.22 mg, 1.3 µmol) was dissolved in THF (300 µL) and N$_2$ gas was purged 30 minutes to the solution. To this reaction mixture, 500 µL THF was added and sealed and then put into a pre-heated oil bath at 62° C. for 40 h. To remove unreactive monomers, the resultant mixture was precipitated in cold ethyl ether (20 mL) to yield the random copolymer as a waxy liquid. GPC (THF) $M_n$: 13 K. PDI: 1.2. $^1$H NMR (400 MHz, CDCl$_3$) δ: 8.46, 7.68, 7.11, 4.35-4.09, 3.94-3.37, 3.03, 2.04-1.64, 1.43-0.87. The molar ratio between two blocks was determined by integrating the methoxy proton in the polyethylene glycol unit and the aromatic proton in the pyridine and found to be 5.0:5.0(PEO:PDSEMA).

Random copolymer 3. A mixture of 2-Cyano-2-propyl benzodithioate (3 mg, 0.0135 mmol), PDSEMA (77.6 mg, 0.304 mmol), polyethylene glycol monomethyl ether methacrylate (61.89 mg, 0.130 mmol) and AIBN (0.22 mg, 1.3 µmol) was dissolved in THF (300 µL and $N_2$ gas was purged 30 min to the solution. To this reaction mixture, 500 µL THF was added and sealed and then put into a pre-heated oil bath at 62° C. for 40 h. To remove unreactive monomers, the resultant mixture was precipitated in cold ethyl ether (20 mL) to yield the random copolymer as a waxy liquid. GPC (THF) $M_n$: 14.4 K. PDI: 1.6. $^1$H NMR (400 MHz, $CDCl_3$) δ: 8.44, 7.65, 7.08, 4.29-4.05, 3.78-3.35, 3.00, 2.02-1.66, 1.34-0.87. The molar ratio between two blocks was determined by integrating the methoxy proton in the polyethylene glycol unit and the aromatic proton in the pyridine and found to be 3.3:6.7 (PEO:PDSEMA).

Random copolymer 4. A mixture of S-dodecyl-S'-2-(2,2-dimethylacetic acid) trithiocarbonate (90 mg, 0.28 mmol), PDSEMA (5 g, 19.6 mmol), polyethylene glycol monomethyl ether methacrylate (4 g, 8.4 mmol) and AIBN (10 mg, 0.056 mmol) was dissolved in DMF (10 mL) and degassed by performing three freeze-pump-thaw cycles. The reaction mixture was sealed and then put into a pre-heated oil bath at 70° C. for 12 h. The resultant mixture was dissolved in dichloromethane (5 mL) and precipitated in hexane (200 mL). To remove unreactive monomers, the precipitate was further dissolved in dichloromethane (5 mL) and re-precipitated in ethyl ether (200 mL) to yield purified the random copolymer as a waxy liquid. Yield: 78%. GPC (THF) $M_n$: 24.7 K. PDI: 1.6. $^1$H NMR (400 MHz, $CDCl_3$) δ: 8.45, 7.68, 7.11, 3.80-3.42, 3.02, 2.04-1.65, 1.24-0.87. The molar ratio between two blocks was determined by integrating the methoxy proton in the polyethylene glycol unit and the aromatic proton in the pyridine and found to be 3.1:6.9 (PEO:PDSEMA).

Nanogel Preparation: The polymer (10 mg) was dissolved in water and placed in a vessel pre-heated at 70° C. for 10 min. When the polymer solution turned turbid, a measured amount of DTT was added. Then the mixture was stirred for another hour to allow for crosslinking. The resulting nanogels were purified by dialysis using a 10,000 g/mol membrane.

Crosslinking density: To determine the crosslinking density, the polymer (0.8 mg/mL) in water was first treated with the requisite amount of DTT (10, 20, 50 mol % compared to PDS groups), and stir the mixture overnight at room temperature. UV-vis measurements were performed with samples of this solution diluted ten times. Once this was measured, the amount of pyridothione was calculated based on its known molar extinction coefficient ($8.08 \times 10^3$ $M^{-1}$ $cm^{-1}$ at 343 nm) (*Bioconjugate Chem.* 2006, 17, 1376-1384). The percentage of cross-linking was calculated by assuming that formation of a single, crosslinking disulfide bond would require cleavage of two PDS units and produce two pyridothione molecules.

Nanogels with Encapsulated Lipophilic Guest Molecules: The polymer (10 mg) and Nile red (2 mg) were dissolved in 200 µL of acetone and a measured amount of DTT (2 µmol, 4 µmol and 5 µmol for 10 mol %, 20 mol % and 50 mol % respectively against PDS groups) was added. After stirring for 10 min, 1 mL of deionized water was added and the mixture was stirred overnight at room temperature, open to the atmosphere allowing the organic solvent to evaporate. Excess insoluble Nile red was removed by filtration and pyridothione was removed from the nanogel solution by ultrafiltration (triplicate) using a membrane with a molecular weight cutoff of 10,000 g/mol (Amicon Ultra cell-10K). For FRET experiments, nanogels were prepared using 1% DiO and 1% DiI in acetone instead of Nile red using the same procedure. Dox encapsulated nanogels were prepared using doxorubicin hydrochloride dissolved in $CH_2Cl_2$ with 3 eq. $NEt_3$ using the same procedure.

Cell Culture: The cell viabilities of the nanogels were tested with 293T cells. 293T cells were cultured in T75 cell culture flasks using Dulbecco's Modified Eagle Medium/ Nutrient Mixture F-12 (DMEM/F12) with 10% fetal bovine serum (FBS) supplement. The cells were seeded at 10,000 cells/well/200 µL in a 96 well plate and allowed to grow for 24 h under incubation at 37° C. and 5% $CO_2$. These cells were then treated with nanogels of different concentrations and were incubated for another 24 h. Cell viability was measured using the Alamar Blue assay with each data point measured in triplicate. Fluorescence measurements were made using the plate reader SpectraMax M5 by setting the excitation wavelength at 560 nm and monitoring emission at 590 nm on a black well plate. The toxicity of Dox-encapsulated polymer nanogels was tested against the MCF-7 cell line. The cells were treated with Dox-encapsulated polymer nanogels of different concentrations and were incubated for 72 h. Cell death was measured by the Alamar Blue assay in triplicate.

Laser Scanning Confocal Microscopy: The laser confocal experiment was performed with MCF-7 cells. MCF-7 cells were cultured in T75 cell culture flask containing DMEM/ F12 with 10% FBS supplement. The cells were seeded at 10,000 cells/100 µL in cover slip-bottomed Petri dishes and allowed to grow for 3 days at 37° C. in a 5% $CO_2$ incubator. The cells in 2 mL of culture medium were treated with 200 µL of nanogels containing two dyes or doxorubicin and incubated at 37° C. for different time intervals before monitoring the cells by confocal microscopy.

Pentafluorophenyl Activated Esters and Bifunctional Cross-Linkers

Unless mentioned, all chemicals were used as received from Sigma-Aldrich. $^1$H-NMR spectra were recorded on a 400 MHz Bruker NMR spectrometer while $^{19}$F-NMR spectra were collected on a 300 MHz Bruker NMR spectrometer. Molecular weight of the polymers was measured by gel permeation chromatography (GPC, Waters) using a PMMA standard with a refractive index detector. THF was used as eluent with a flow rate of 1 mL/min. DLS measurements were performed using a Malvem Nanozetasizer. FTIR spectra were recorded on a Perkin Elmer spectrometer.

Synthesis of pentafluorophenyl acrylate PFPA: Monomer was synthesized by using a previously reported procedure. Briefly, pentafluorophenol (5.40 g, 29.3 mmol) and 2,6-lutidine (3.80 mL, 32.7 mmol) were dissolved in dry dichloromethane (50.0 mL). The above solution was cooled in an ice bath and then acryloyl chloride was added (2.65 mL, 32.7 mmol). After stirring at ambient temperature for 12 h, the reaction mixture was washed with water. The organic layer was collected, and dried over anhydrous sodium sulfate. Crude product was further purified by flash chromatograph to afford pure product. Yield: 54%. $^1$H NMR (400 MHz, CDCl3) δ : 6.74 (d, 1H), 6.36 (q, 1H), 6.19 (d, 1H). $^{19}$F NMR (300 MHz, CDCl3) δ: −152.5 (2F, d), −157.9 (1F, t), −162.3 (2F, d).

Synthesis of random copolymer PPFPA-r-PEGMA: To a Schlenk-flask, pentafluorophenyl acrylate (500.0 mg, 2.1 mmol), poly(ethylene glycol) methyl ether methacrylate (428.0 mg, 0.9 mmol), recrystallized azodiisobutyonitrile (AIBN) (2.5 mg, 0.015 mmol), and 4-cyano-4-((thiobenzoyl)-sulfanyl) pentanoicacid (33.5 mg, 0.120 mmol) were mixed in 1, 4-dioxane (900 µL). The solution mixture was subjected to three freeze-pump-thaw cycles. The sealed flask was immersed in a preheated oil bath at 75° C. The polymerization reaction was allowed to proceed for 5 days. The reaction was stopped by immersing the reaction flask in cold water. After the removal of 1, 4-dioxane, the mixture was precipitated in hexane. The resulting mixture was dissolved in THF and then precipitated in hexane. The same operation was repeated one more time to afford the pure polymer. Yield 90%: $^1$H NMR (400 MHz, CDCl3) δ: 4.0-4.2 ppm, 3.5-3.8 ppm, 3.3-3.4 ppm, 2.7-3.2 ppm, 0.9-2.6 ppm. $^{19}$F NMR (300 MHz, CDCl$_3$) δ: −152 to −155 ppm (2F), −158 to −160 ppm (1F), −164 to −166 ppm (2F). GPC (THF) Mn: 9.5 kDa. PDI: 1.3. By comparing the integral of the methylene protons adjacent to the ester in the polyethylene glycol unit and the polymer backbone proton in both the polyethylene glycol and the pentafluorophenyl units, the molar ratio was found to be 3:7 (PEGMA: PFPA).

Nanogel preparation in THF: 4.0 mg of polymer was dissolved in a known volume of dry THF to make a polymer solution with the desired concentration. To the polymer solution was added 0.50 equivalents of cross-linker with respected to the PFP groups and 1 equivalent of diisopropylethylamine (DIPEA). The solution was then heated at 50° C. for 4 h to afford 100% cross-linked nanogel. The cross-linking reaction was characterized by FTIR. H$_2$O was added to the nanogel solution and the THF was evaporated by stirring the solution in air for 24 h. The volume of nanogel solution was adjusted by adding water to afford the desired concentration. Preparation of the nanogel loaded with DiI (DiIC18(3)) follows the same procedure using a polymer solution mixed with 1 wt % DiI. After cross-linking and evaporation of THF, the nanogel solution was further purified by triplicate dialysis in milliQ water for 3 days.

Nanogel preparation in water: 4.0 mg of polymer solution was dissolved in H$_2$O to afford a polymer solution with the desired concentration. To the polymer solution, 0.50 equivalents of cross-linker with respect to the PFP groups and 1 equivalent of diisopropylethylamine (DIPEA) were added. The polymer solution was heated at 50° C. for 4 hours to afford 100% cross-linked nanogel.

Nanogel modification: 400 mL of 10.0 mg/mL polymer solution in THF was half cross-linked by the addition of 0.25 equivalents of CYS and 0.50 equivalents of DIPEA with respect to the PFP groups. After heating at 50° C. for 4 hours, 2.0 equivalents of isopropylamine (IPA) or N,N-dimethylethylenediamine (DMEDA) with 2 equivalents of DIPEA (with respect to the remaining PFP groups after cross-linking) were added to the nanogel solution and heated at 50° C. for another 4 hours. Cross-linking and post-nanogel substitution were monitored by FTIR. Water was added to the modified nanogel solution. THF was evaporated by stirring the sample in air for 24 hours. The nanogel solution was further purified by triplicate dialysis in milliQ water for 3 days.

Concurrent Binding and Delivery of Proteins and Lipophilic Small Molecules

All chemicals, 2,2'-Dithiodipyridine, polyethylene glycol monomethyl ether methacrylate (MW 450), D,L-dithiothreitol (DTT), 1,1'-dioctadecyl-3,3,3',3'-tetramethyl-indocarbocyanine perchlorate (DiI), β-galactosidase (β-gal) from *E. coli*, 2-nitrophenyl-β-D-galactopyranosidase, UltraPure Agarose and solvents were purchased from commercial sources and were used as received, unless otherwise mentioned. Pyridyl disulfide ethyl methacrylate (PDSEMA) was prepared using a previously reported procedure (*Macromolecules* 2006, 39, 5595-5597). $^1$H-NMR spectra were recorded on a 400 mHz Bruker NMR spectrometer using the residual proton resonance of the solvent as the internal standard. Chemical shifts are reported in parts per million (ppm). Molecular weights of the polymers were estimated by gel permeation chromatography (GPC) using PMMA standard with a refractive index detector. DLS measurements were performed using a Malvern Nanozetasizer. UV-vis absorption spectra were recorded on a Varian (model EL 01125047) spectrophotometer. The fluorescence spectra were obtained from a JASCO FP-6500 spectrofluorometer.

Synthesis of Random Copolymer: A mixture of 2-cyano-2-propyl benzodithioate (21 mg, 0.0949 mmol), PDSEMA (860 mg, 3.37 mmol), polyethylene glycol monomethyl ether methacrylate (620 mg, 1.31 mmol) and AIBN (5.0 mg, 0.0305 mmol) was dissolved in THF (3 mL) and degassed by performing three freeze-pump-thaw cycles. This reaction vessel was sealed and then placed in a pre-heated oil bath at 60° C. for 12 h. To remove unreactive monomers and purify the polymer, the resultant mixture was precipitated in cold ethyl ether (20 mL) to yield the random copolymer as a waxy solid. GPC (THF) M$_n$: 23 K. PDI: 1.38. $^1$H NMR (400 MHz, CDCl$_3$) δ: 8.45, 7.66, 7.09, 4.20-4.06, 3.90-3.36, 3.01, 2.15-1.62, 1.43-0.86. The molar ratio between two blocks was determined by integrating the methoxy proton in the polyethylene glycol unit and the aromatic proton in the pyridine and found to be 29%:71% (PEO:PDSEMA)

Synthesis of CRRR peptide: 2-chloro-trityl chloride resin was selected as the solid support to prepare the peptide using solid phase synthesis. Coupling reaction was carried out in the presence of 3 equiv. of Fmoc protected amino acid, 3 equiv. of HATU and 3 equiv. of DIPEA and was tested by Kaiser Test. Deprotection of Fmoc group was obtained by treating the resin with 20% piperidine in DMF. The peptide was finally cleaved from resin by reacting with TFA/TIS/H$_2$O/EDT mixture. Precipitating the mixture in cold ether 5 times affords the crude peptide. Peptide was used without further purification. Yield: 80%. Peptide was characterized by $^1$H NMR and MS. $^1$H NMR (400 MHz, D$_2$O) δ:4.45-4.52, 4.30-4.41, 4.03-4.11, 3.15-3.26, 2.92-3.01, 1.73-1.96, 1.55-1.96. MS (FAB): exact mass calculated: 590.7. Found: 590.0.

Nanogel synthesis and surface modification: The polymer (10 mg) was dissolved in water (1 mL) and the hydrophobic dye (0.2 mg of DiI) in acetone (100 μL) was added. The mixture was stirred for 6 h at room temperature, open to the atmosphere allowing the organic solvent to evaporate. To this micellar aggregate solution, was added a measured amount of DTT and then the mixture was stirred for 12 h at room temperature to allow for crosslinking. To modify the nanogel's surface, the ligand (5 mg), CRRR, was added and then stirred for another 12 h. The resulting nanogels were purified by filtration and unattached excess ligand was removed from the nanogel solution by ultrafiltration (triplicate) using a membrane with a molecular weight cutoff of 10,000 g/mol (Amicon Ultra cell-10 K).

Crosslinking density and peptide modification: In order to determine the crosslinking density, UV-vis measurements were performed with samples of this solution diluted ten times. Once this was measured, the amount of pyridothione was calculated based on its known molar extinction coefficient ($8.08 \times 10^3$ M$^{-1}$ cm$^{-1}$ at 343 nm) (*Bioconjugate Chem.* 2006, 17, 1376-1384). The percentage of cross-linking was calculated by assuming that formation of a single, cross-linking disulfide bond would require cleavage of two PDS units and produce two pyridothione molecules. The attachment of the ligand was evaluated by further increase in pyridothione absorption (FIG. 36).

Calculation of Crosslinking Density:
  Sample concentration in UV: 0.1 mg/ml of polymer.
  The molar ratio of each unit: PDS:PEG=x mol: y mol=71:29 (from repeating unit by NMR)
  PDS molecular weight=255 g/mol, PEG molecular weight=475 g/mol
So, x mol*255 g/mol+y mol*275 g/mol=0.1 mg
x mol=71/29 y mol
Therefore, x mole (PDS) is $2.23*10^{-7}$ mol in this solution
NG1
Absorbance is 0.31 at 343 nm.
By Beer's law, $$A=\varepsilon bc$$

$$0.31=8.08*10^3 M^{-1}\, cm^{-1}*1\, cm*c$$

$$c=3.84*10^{-5} M$$

Therefore, 1 mL of resulting nanogel solution contains $3.84*10^{-8}$ mol pyridothione (byproduct).
It is 17 mol % of total PDS unit ($2.23*10^{-7}$ mol). It was assumed that two pyridothione are from one disulfide formation and PDS unit is 71 mol % of total polymer.
Therefore, 17%/2*0.71=6% crosslinking density.
NG2
Absorbance is 0.703 at 343 nm.
By Beer's law, $$A=\varepsilon bc$$

$$0.703=8.08*10^3 M^{-1}\, cm^{-1}*1\, cm*c$$

$$c=8.70*10^{-5} M$$

Therefore, 1 mL of resulting nanogel solution contains $8.70*10^{-8}$ mol pyridothione (byproduct).
It is 39 mol % of total PDS unit ($2.23*10^{-7}$ mol). It is assumed that two pyridothiones are from one disulfide formation and PDS unit is 71 mol % of total polymer.
Therefore, 39%/2*0.71=14% crosslinking density.
Loading Degree of Hydrophobic Dye (DiI):
  2 wt % DiI (0.2 mg/mL) were added into polymer solution (10 mg/mL). The final loading amount was calculated based on molar extinction coefficient of DiI ($104\times10^3$ $M^{-1}$ $cm^{-1}$ at 555 nm.
  The polymer concentration: 0.1 mg/mL solution (diluted from 5 mg/mL stock from the nanogels used for UV measurement to 0.1 mg/ml to final volume of 0.6 mL)
NG1:
absorbance at 555 nm=0.310

$$C=0.310/(104\times10^3 M^{-1}\, cm^{-1}\times 1\, cm)=2.98\times10^{-6} M$$

Conversion to grams of DiI:

$$2.98\mu M\times 961.32\, g/mol\times 0.6\, mL=1.7\, \mu g\, DiI$$

wt % loading=DiI in nanogel/weight total nanogel=1.7 µg/0.1 mg×100=1.7 wt %
Loading efficiency: loaded amount/feed amount=1.7 µg/2 µg×100=85%
NG2:
absorbance at 555 nm=0.323

$$C=0.323/(104\times10^3 M^{-1}\, cm^{-1}\times 1\, cm)=3.11\times10^{-6} M$$

Conversion to grams of DiI:

$$3.11\mu M\times 961.32\, g/mol\times 0.6\, mL=1.8\, \mu g\, DiI$$

wt % loading=DiI in nanogel/weight total nanogel=1.8 µg/0.1 mg×100=1.8 wt %
Loading efficiency: loaded amount/feed amount=1.8 µg/2 µg×100=90%

Labeling of β-gal with FITC: Fluorescein isothiocyanate isomer I (FITC) was dissolved in dimethyl sulfoxide at a concentration of 4 mg/mL. The β-gal (2.5 mg) was dissolved in 900 µL of 0.1 M sodium bicarbonate solution (pH 9.0) and mixed with 250 µL freshly prepared FITC solution. The mixture was protected from light and stirred gently at room temperature for 2 h. The resulting FITC labeled β-gal was purified by size exclusion chromatography with Sephadex G-25 as stationary phase and phosphate buffer (5 mM, pH 7.4) as mobile phase. Finally, the β-gal concentration and labeling efficiency were measured by UV-vis absorption spectroscopy.

Nanogel-protein complex optimization: NG-CRRR with encapsulated DiI (2 mg/mL) and FITC labeled β-gal (1 mg/mL) stock solutions were prepared in 5 mM Sodium phosphate buffer. β-gal-NG-CRRR complex solutions were prepared from 1:1 to 1:6 ratios (β-gal:NG-CRRR) and incubated for 1 h before spectroscopic measurements. The change of the intensity of FITC, which occurs by FRET between FITC in β-gal and DiI inside nanogels, was recorded by fluorescence spectroscopy with increasing nanogel concentration at same β-gal concentration in the solution. The intensity of FITC was decreasing as increasing the DiI-containing nanogels and stopped changing for NG1-CRRR-β-gal complex at 2:1 ratio and at 4:1 ratio for NG2-CRRR-β-gal, indicating that the stable complexation is formed above this concentration.
Estimation of Number of Nanogels Per Protein in Complex:
Diameter Values(DLS):
β-gal=10 nm
NG1-CRRR=20 nm NG1-CRRR-β-gal=40 nm
NG2-CRRR=12 nm NG2-CRRR-β-gal=30 nm
Calculation for NG1:
NG1-CRRR-β-gal complex radius=20 nm
Volume=4/3 π $(20\, nm)^3 = 3.35\times10^4\, nm^3$
NG1-CRRR radius=10 nm
Volume=4/3 π $(10\, nm)^3 = 4.19\times10^3\, nm^3$
β-gal radius=5 nm
Volume=4/3 π $(5\, nm)^3 = 5.23\times10^2\, nm^3$
Note: The ratio is 2:1 of NG1 and/β-gal.
Assuming that number of NG1-CRRR is 2p and number of β-gal is p in complex.
The summation of volume of 2p NG1-CRRR and p β-gal=the volume of complex:

$$2p\times 4.19\times 10^3\, nm^3 + p\times 5.23\times 10^2\, nm^3 = 3.35\times 10^4\, nm^3$$

$$p=3.35\times 10^4\, nm^3/(2\times 4.19\times 10^3\, nm^3+5.23\times 10^2\, nm^3)=3.76$$

Thus, the average numbers of NG1-CRRR and β-gal per complex are 7.6 and 3.8 respectively.
Calculation for NG2:
NG2-CRRR-β-gal complex radius=15 nm
Volume=4/3 π $(15\, nm)^3 = 1.41\times10^4\, nm^3$
NG2-CRRR radius=6 nm.
Volume=4/3 π $(6\, nm)^3 = 9.04\times10^2\, nm^3$
β-gal radius=5 nm
Volume=4/3 π $(5\, nm)^3 = 5.24\times10^2\, nm^3$
Note: The ratio is 4:1 of NG2 and β-gal.
Assuming that number of NG2 is 4 q and number of β-gal is q in complex.
The summation of volume of 4 q NG2 and q β-gal=the volume of complex:

$$4q\times 9.04\times 10^2\, nm^3 + q\times 5.24\times 10^2\, nm^3 = 1.41\times 10^4\, nm^3$$

$$q=1.41\times 10^4\, nm^3/(4\times 9.04\times 10^2\, nm^3+5.24\times 10^2\, nm^3)=3.41$$

Result:
Thus, the average numbers of NG2-CRRR and β-gal per complex are 13.6 and 3.4 respectively.

Agarose Gel Electrophoresis Studies: Agarose gel electrophoresis was performed to observe nanogel and protein complexation taking advantage of the nanogel (positive) and β-gal (negative) charges differences. 10 μL samples were prepared in Milli Q water: (1) β-gal control (100 μg), (2) NG1-CRRR control (200 μg), (3) NG1-CRRR: β-gal complex (200 μg: 100 μg, (4) NG2-CRRR control (400 μg), and (5) NG2-CRRR: β-gal complex (400 μg: 100 μg: with the addition of 1 μL Bromophenol blue (10 mg/mL). The nanogels were incubated with the protein for 1 hour at room temperature. To prepare the gel, 270 mg of Ultra Pure Agarose was diluted in 1×TAE buffer pH 8.0 and the solution was microwaved until getting a homogeneous solution. The gel was poured in a FisherBiotech Electrophoresis System (FB-SB-710) and let stand until the gel solidified with an 8 well comb. The gel was run with 1×TAE buffer at 100 mV for 1 hour and 10 minutes at room temperature. The gel was washed with Milli Q water for 10 minutes and stained with Gel Code Blue for 1 hour.

Figure 35:
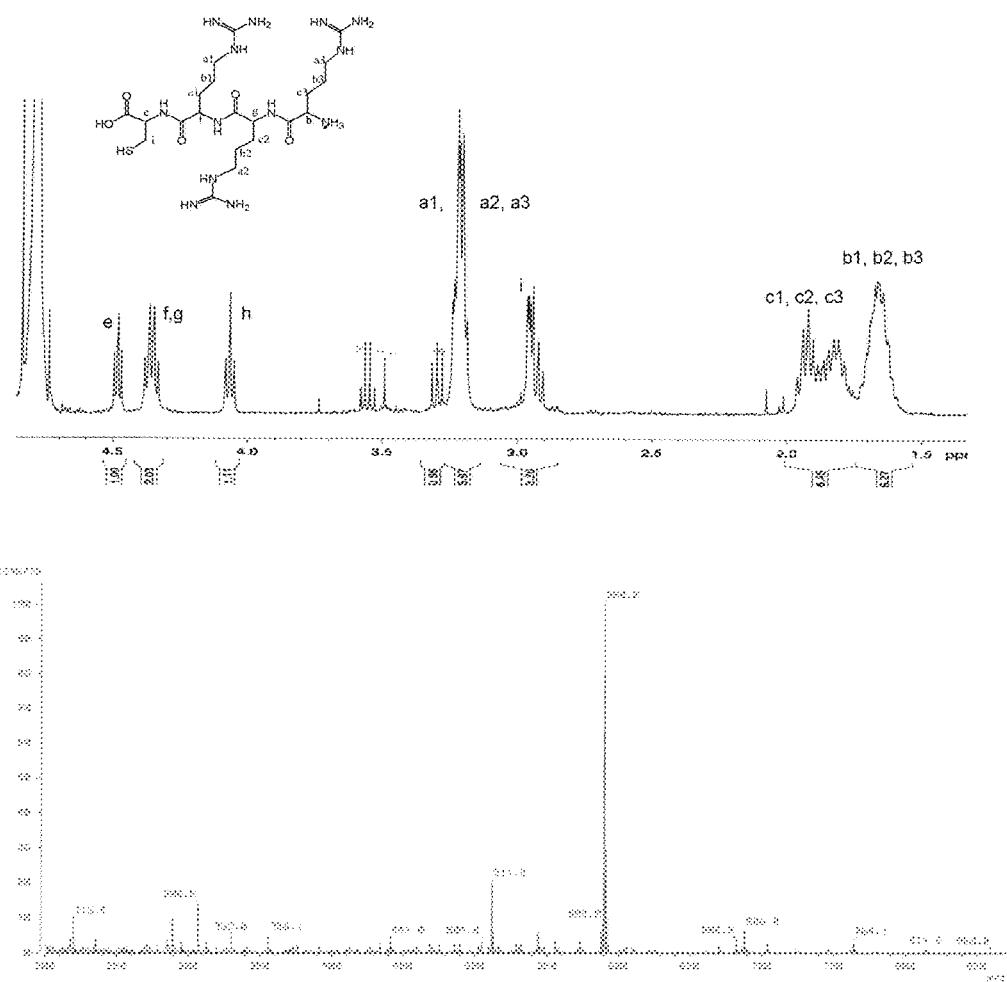
FIG. 35 shows exemplary NMR and Mass spectra of triarginine peptide.

As shown in FIG. 35 complexation of NG1-CRRR with β-gal is evident in Lane 3. Free protein in lane 3 almost disappeared and there is some extension of the nanogel mark towards the cathode showing interaction between the nanogel and protein charges meaning that the positive charges of the nanogel are shielded by negative charges of β-gal. Some complexation between NG2-CRRR and β-gal is observed as well, however this interaction is weaker than that with NG1.

β-gal activity assay: Solutions of native β-gal (MW=116, 300 g/mol monomeric form), β-gal-NG1-CRRR (1:2 ratio) and β-gal-N2-CRRR (1:4 ratio) were prepared in PBS buffer pH 7.4 and incubated for 1 hour. β-gal activity was assessed in a 96 well plate using SpectraMax M5 plate reader. By adding the colorimetric substrate 2-nitrophenyl-β-D-galactopyranoside (2.5 mM) activity of β-gal was recorded by the absorbance increase over time of pNP at 405 nm excitation wavelength.

Laser Scanning Confocal Microscopy: The laser confocal experiment was performed with HeLa cells which were cultured in T75 flasks containing DMEM/F12 with 10% FBS supplement. The cells were seeded at 10,000 cells/100 μL in cover slip-bottomed Petri dishes and allowed to grow for 1 day at 37° C. in a 5% $CO_2$ incubator. The cells in 2 mL of culture medium were treated with nanogels (0.1 mg/mL) containing dye and bound to protein; incubated for 3 hours at 37° C. before monitoring the cells by confocal microscopy (excitation of both dye molecules at 488 nm and 543 nm for FITC and DiI, respectively)

X-gal Studies:
HeLa cells were seeded in a 96 well plate at 10,000 cells/well. After 24 hours cells were washed with PBS. NG1 and NG2 complexes with β-gal were prepared at ratios of 2:1 and 4:1 respectively and added to cells in serum free DMEM/F12 media. Cells were incubated with the complexes for 3 hours. This was followed by washing cells with PBS twice and addition of DMEM/F12 with 10% FBS supplement. After another 3 hours of incubation, X-gal staining studies were carried out according to the manufacturers' protocol (Genlantis). Briefly, after fixing cells for 15 minutes they were washed twice with 1×PBS followed by addition of 80 μL 1× staining buffer. After overnight incubation cells were washed again and images were taken with an inverted microscope at 40× magnification using the Micron software.

Ligand-Decorated Nanogels and Cellular Targeting

General. 2,2'-Dithiodipyridine, 2-mercaptoethanol, polyethylene glycol monomethyl ether methacrylate (MW 450), D,L-dithiothreitol (DTT), 1,1'-dioctadecyl-3,3,3',3'-tetramethylindocarbo-cyanine perchlorate (DiI) and 3,3'-dioctadecyloxacarbocyanine perchlorate (DiO), folic acid, cyclo (Arg-Gly-Asp-D-Phe-Cys) peptide, 2-cyano-2-propyl benzodithioate and other conventional reagents were obtained from commercial sources and were used as received, unless otherwise mentioned. Polymers were synthesized using RAFT polymerization and then purified by precipitation. Pyridyl disulfide ethyl methacrylate (PDSEMA) was prepared using a previously reported procedure. (Ghosh, et al. 2006 Macromolecules 39, 5595-5597)$^1$H-NMR spectra were recorded on a 400 MHz Bruker NMR spectrometer using the residual proton resonance of the solvent as the internal standard. Molecular weights of the polymers were estimated by gel permeation chromatography (GPC) using PMMA standard with a refractive index detector. DLS measurements were performed using a Malvem Nanozetasizer. The fluorescence spectra were obtained from a JASCO FP-6500 spectrofluorimeter. Transmission electron microscopy (TEM) images were taken from JEOL 100 CX at 100 KV.

Random copolymer. A mixture of 2-cyano-2-propyl benzodithioate (21.0 mg, 0.095 mmol), PDSEMA (860 mg, 3.37 mmol), polyethylene glycol monomethyl ether methacrylate (620 mg, 1.31 mmol) and AIBN (5.0 mg, 0.031 mmol) was dissolved in THF (3 mL) and degassed by performing three freeze-pump-thaw cycles. This reaction vessel was sealed and then put into a pre-heated oil bath at 60° C. for 12 h. To remove unreactive monomers, the resultant mixture was precipitated in cold diethylether (20 mL) to yield the random copolymer as a waxy liquid. GPC (THF) $M_n$: 23 K. PDI: 1.38. H NMR (400 MHz, $CDCl_3$) δ: 8.45, 7.66, 7.09, 4.20-4.06, 3.90-3.36, 3.01, 2.15-1.62, 1.43-0.86. The molar ratio between two blocks was determined by integrating the methoxy proton in the polyethylene glycol unit and the aromatic proton in the pyridine and found to be 29%:71% (PEO:PDSEMA).

Cell penetrating peptide CRRR: Peptide was synthesized on 2-chloro-trityl chloride resin by solid phase synthesis using standard Fmoc methodology. Briefly, coupling reaction was achieved by 3 equiv. Fmoc protected amino acid, 3 equiv. HATU, and 3 equiv DIPEA in DMF and monitored by Kaiser Test. Fmoc protection group was removed by 20% piperidine in DMF. Cleavage of peptide from resin was performed in the presence of $TFA/TIS/H_2O/EDT$ mixture. Then cleavage mixture was precipitated in cold ether 5 times to afford crude peptide. Peptide was used without further purification. Yield: 80%. Peptide was characterized by $^1$H-NMR and mass spectrometry.

Cysteine-folic acid: The ligand was prepared on cysteine preloaded 2-chlorotrityl resin by solid phase synthesis. The resin was treated with 1.2 eq folic acid and 1.2 eq DIPEA in DMSO for 24 hours. The coupling reaction was repeated twice. Cleavage of cysteine-folic acid was done by treating the resin with $TFA/TIS/H_2O/EDT$ mixture. Crude product was obtained by precipitation in cold ether 5 times. Yield: 78%. Characterization was followed by $^1$H-NMR and mass spectrometry.

T-NGs preparation: The polymer (10 mg) was dissolved in water (1 mL) and hydrophobic dyes (0.1 mg of DiO or DiI) or 0.5 mg paclitaxel in acetone (100 μL) was added and the mixture was stirred for 6 h at room temperature, open to the atmosphere allowing the organic solvent to evaporate. It was placed in a vessel pre-heated at 60° C. for 10 min and then a measured amount of DTT was added. Then the mixture was stirred for 30 min to allow for crosslinking. To modify the nanogels surface, the ligand (5 mg), CRRR, cRGD, or cyteine-modified folic acid, was added and then stirred for another 1 h. The resulting nanogels were purified by filtration and unattached excess ligand was removed from the nanogel solution by ultrafiltration (triplicate) using a membrane with a molecular weight cutoff of 10,000 g/mol (Amicon Ultra cell-10 K).

Crosslinking density and surface modification: In order to determine the crosslinking density, the polymer in water was first treated with the requisite amount of DTT (20 mol % compared to PDS groups), and stir the mixture at 60° C. UV-visible spectroscopic measurements were performed with samples of this solution diluted ten times. Once this was measured, the amount of pyridothione was calculated based on its known molar extinction coefficient ($8.08 \times 10^3$ $M^{-1}$ $cm^{-1}$ at 343 nm). (Kavimandan, et al. 2006 *Bioconjugate Chem.*, 17, 1376-1384) The percentage of cross-linking was calculated by assuming that formation of a single, crosslinking disulfide bond would require cleavage of two PDS units and produce two pyridothione molecules. The attachment of the ligand was evaluated by further increase in pyridothione absorption.

Cell culture: The cell viabilities of the nanogels were tested with 293T cells. 293T cells were cultured in T75 cell culture flasks using Dulbecco's Modified Eagle Medium/Nutrient Mixture F-12 (DMEM/F12) with 10% fetal bovine serum (FBS) supplement. The cells were seeded at 10,000 cells/well/200 μL in a 96 well plate and allowed to grow for 24 hours under incubation at 37° C. and 5% $CO_2$. These cells were then treated with nanogels of different concentrations and were incubated for another 24 hours. Cell viability was measured using the Alamar Blue assay with each data point measured in triplicate. Fluorescence measurements were made using the plate reader SpectraMax M5 by setting the excitation wavelength at 560 nm and monitoring emission at 590 nm on a black well plate. The toxicity of paclitaxel (PTX)-encapsulated polymer aggregates, NG, and NG-RGD were tested against the MCF7 and HeLa cell line. The cells were treated with PTX-encapsulated polymer nanogels of 10 μM concentrations and were incubated for 72 hours. Cell death was measured by the Alamar Blue assay in triplicate.

Laser scanning confocal microscopy: The laser confocal experiment was performed with different cell lines. Each cell line was cultured in T75 cell culture flask containing DMEM/F12 with 10% FBS supplement. The cells were seeded at 10,000 cells/100 μL in cover slip-bottomed petri dishes and allowed to grow for 1 day at 37° C. in a 5% $CO_2$ incubator. The cells in 2 mL of culture medium were treated with polymer aggregates, nanogels, or T-NGs (0.1 mg/mL) containing dyes and incubated at 37° C. for different time intervals before monitoring the cells by confocal microscopy.

Calculation of the number of ligand (CRRR) per T-NG. The attachment of the ligand was evaluated by further increase in pyridothione absorption. Based on UV-vis measurement and molar extinction coefficient of pyridothione, the amount of the ligand was calculated that is attached onto the surface of nanogels. The number of ligand per T-NG was estimated by following equation. It was assumed that the nanogel density is around 1.00 g/cm³.

The volume of one $T\text{-}NG =$
$$4\pi r^3/3 = 4\pi (21 \text{ nm})^3/3 = 3.879 \times 10^4 \text{ nm}^3 = 3.879 \times 10^{-23} \text{ m}^3$$

The mass of one $T\text{-}NG$ = the volume of $T\text{-}NG/$
density of $T\text{-}NG$
$= 3.879 \times 10^{-23} \text{ m}^3 / 1.00 \text{ g/cm}^3$
$= 3.879 \times 10^{-17}$ g The number of $T\text{-}NG$ in solution = total nanogel amount/
the mass of one $T\text{-}NG$
$= \dfrac{6.35 \times 10^{-5} \text{ g}/}{3.879 \times 10^{-17} \text{ g}}$
$= 1.637 \times 10^{12}$ The molar concentration of the ligand which is attached on the surface of nanogel is obtained by absorption intensity and extinction coefficient of pyridothione, which is 0.01925 μmol. Therefore, the number of ligand per one T-NG is estimated like following:

$1.925 \times 10^{-8}$ mol$\times 6.02 \times 10^{23}$ mol$^{-1}$/the number of T-NG in solution=$7.08 \times 10^3$

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

The invention claimed is:
1. A method for delivering a therapeutic, diagnostic or imaging agent to a biological site, comprising:
   providing a nano-assembly, comprising:
      a water-soluble polymer host comprising a crosslinked network of polymer molecules;
      a guest molecule comprising a therapeutic, diagnostic or imaging agent non-covalently associated with the polymer host, wherein the therapeutic, diagnostic or imaging agent is releasable upon partial or complete de-crosslinking of the crosslinked network of polymer molecules at or near the biological site; and
      a targeting moiety, covalently linked to or non-covalently associated with the polymer host, selected from an antibody, an aptamer, a peptide, and a small molecule ligand;
   transporting the nano-assembly to the biological site; and causing at least partial de-crosslinking of the crosslinked network of polymer molecules, thereby releasing the therapeutic, diagnostic or imaging agent at or near the biological site, wherein the polymer host comprises a crosslinked network of a block or random co-polymer having the structural formula:

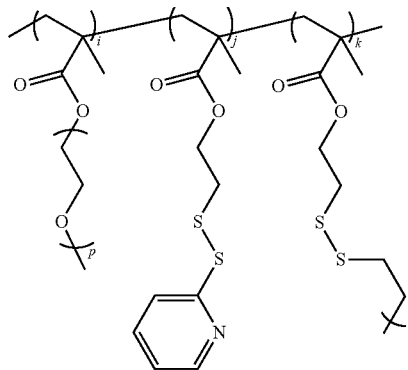

wherein p is an integer from 1 to 20, and
wherein
each of i and j is independently a positive number, k may be zero or a positive number.

2. The method of claim 1, wherein the targeting moiety is a peptide.

3. The method of claim 1, wherein the co-polymer has a molecular weight from about 1,000 to about 100,000 and the ratio of i:j is in the range from about 2:8 to about 8:2.

4. The method of claim 1, wherein the crosslinked network of polymer molecules is crosslinked both inter-molecularly and intra-molecularly.

5. The method of claim 1, wherein the therapeutic agent is an anti-tumor agent.

6. The method of claim 1, wherein the loading weight percentage of the guest molecule is from about 0.5% to about 70%.

7. The method of claim 1, wherein the biological site is within an organ or tissue or a cell.

8. A method for delivering a therapeutic, diagnostic or imaging agent to a biological site, comprising:
providing a nano-assembly, comprising:
a water-soluble polymer host comprising a crosslinked network of polymer molecules;
a guest molecule comprising a therapeutic, diagnostic or imaging agent non-covalently associated with the polymer host, wherein the therapeutic, diagnostic or imaging agent is releasable upon partial or complete de-crosslinking of the crosslinked network of polymer molecules at or near the biological site; and
a targeting moiety, covalently linked to or non-covalently associated with the polymer host, selected from an antibody, an aptamer, a peptide, and a small molecule ligand;
transporting the nano-assembly to the biological site; and
causing at least partial de-crosslinking of the crosslinked network of polymer molecules, thereby releasing the therapeutic, diagnostic or imaging agent at or near the biological site,
wherein the polymer host comprises a crosslinked network of a block or random co-polymer having the structural formula:

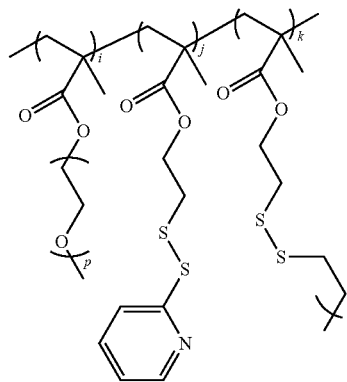

wherein
p is an integer from 1 to 20, and
each of i, j and k is independently a positive number.

* * * * *